United States Patent
Rowe et al.

(10) Patent No.: US 11,774,446 B2
(45) Date of Patent: Oct. 3, 2023

(54) METHODS FOR DIAGNOSIS AND TREATMENT OF AUTOIMMUNE DISEASES

(71) Applicant: Cowper Sciences Inc., Chandler, AZ (US)

(72) Inventors: Michael William Rowe, San Ramon, CA (US); Theodore Michael Tarasow, San Ramon, CA (US); Jonathan Scott Melnick, San Ramon, CA (US)

(73) Assignee: COWPER SCIENCES INC., Chandler, AZ (US)

( * ) Notice: Subject to any disclaimer, the term of this patent is extended or adjusted under 35 U.S.C. 154(b) by 211 days.

(21) Appl. No.: 16/312,168

(22) PCT Filed: Jun. 20, 2017

(86) PCT No.: PCT/US2017/038392
§ 371 (c)(1),
(2) Date: Dec. 20, 2018

(87) PCT Pub. No.: WO2017/223117
PCT Pub. Date: Dec. 28, 2017

(65) Prior Publication Data
US 2019/0234945 A1    Aug. 1, 2019

Related U.S. Application Data

(60) Provisional application No. 62/421,185, filed on Nov. 11, 2016, provisional application No. 62/352,519, filed on Jun. 20, 2016.

(51) Int. Cl.
G01N 33/53        (2006.01)
G01N 33/564       (2006.01)
C07K 14/00        (2006.01)

(52) U.S. Cl.
CPC .......... *G01N 33/564* (2013.01); *C07K 14/00* (2013.01); *G01N 2800/24* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 5,143,854 A | 9/1992 | Pirrung et al. |
| 5,424,186 A | 6/1995 | Fodor et al. |
| 5,449,754 A | 9/1995 | Nishioka |
| 5,571,639 A | 11/1996 | Hubbell et al. |
| 5,593,839 A | 1/1997 | Hubbell et al. |
| 5,595,915 A | 1/1997 | Geysen |
| 5,677,195 A | 10/1997 | Winkler et al. |
| 5,759,774 A | 6/1998 | Hackett et al. |
| 5,919,523 A | 7/1999 | Sundberg et al. |
| 6,083,763 A | 7/2000 | Balch |
| 6,309,831 B1 | 10/2001 | Goldberg et al. |
| 6,329,209 B1 | 12/2001 | Wagner et al. |
| 6,346,413 B1 | 2/2002 | Fodor et al. |
| 6,346,423 B1 | 2/2002 | Schembri |
| 6,359,125 B1 | 3/2002 | Kim et al. |
| 6,365,418 B1 | 4/2002 | Wagner et al. |
| 6,387,631 B1 | 5/2002 | Arnold et al. |
| 6,399,365 B2 | 6/2002 | Besemer et al. |
| 6,465,183 B2 | 10/2002 | Wolber |
| 6,475,808 B1 | 11/2002 | Wagner et al. |
| 6,475,809 B1 | 11/2002 | Wagner et al. |
| 6,489,159 B1 | 12/2002 | Chenchik et al. |
| 6,496,309 B1 | 12/2002 | Bliton et al. |
| 6,511,277 B1 | 1/2003 | Norris et al. |
| 6,545,748 B1 | 4/2003 | Trozera |
| 6,567,163 B1 | 5/2003 | Sandstrom |
| 6,569,671 B1 | 5/2003 | Okamoto et al. |
| 6,573,369 B2 | 6/2003 | Henderson et al. |
| 6,604,902 B2 | 8/2003 | Norris et al. |
| 6,620,584 B1 | 9/2003 | Chee et al. |
| 6,630,358 B1 | 10/2003 | Wagner et al. |
| 6,660,479 B2 | 12/2003 | Kim et al. |
| 6,706,875 B1 | 3/2004 | Goldberg et al. |
| 6,723,517 B1 | 4/2004 | Bamdad |
| 6,733,977 B2 | 5/2004 | Besemer et al. |
| 6,780,582 B1 | 8/2004 | Wagner et al. |
| 6,806,954 B2 | 10/2004 | Sandstrom |
| 6,824,669 B1 | 11/2004 | Li et al. |
| 6,877,665 B2 | 4/2005 | Challa et al. |

(Continued)

FOREIGN PATENT DOCUMENTS

| | | |
|---|---|---|
| CN | 1438324 A | 8/2003 |
| CN | 102099372 A | 6/2011 |

(Continued)

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*

Torzewski et al., Animal Models of C-Reactive Protein, Hindawl Publishing Corporation, Mediators of Inflammation, vol. 2014, 2014, pp. 1-7. (Year: 2014).*

Anic et al., New classification criteria for systemic lupus erythematosus correlate with disease activity, Croat Med J 2014; 55, pp. 514-519. (Year: 2014).*

(Continued)

*Primary Examiner* — Gary Counts
(74) *Attorney, Agent, or Firm* — Wilson Sonsini Goodrich & Rosati

(57) ABSTRACT

Provided herein are methods, assays and devices for the detection and diagnosis of autoimmune diseases, including systemic lupus erythematosus. The methods, assays and devices provided herein analyzes binding patterns of peripheral-blood antibodies on peptide array that correlates well with current systemic lupus erythematosus clinical assessment standards.

15 Claims, 20 Drawing Sheets
Specification includes a Sequence Listing.

(56) References Cited

U.S. PATENT DOCUMENTS

| | | |
|---|---|---|
| 6,890,760 B1 | 5/2005 | Webb |
| 6,897,073 B2 | 5/2005 | Wagner et al. |
| 6,919,181 B2 | 7/2005 | Hargreaves |
| 6,989,267 B2 | 1/2006 | Kim et al. |
| 6,989,276 B2 | 1/2006 | Thompson et al. |
| 7,006,680 B2 | 2/2006 | Gulati |
| 7,081,954 B2 | 7/2006 | Sandstrom |
| 7,108,472 B2 | 9/2006 | Norris et al. |
| 7,130,458 B2 | 10/2006 | Bartell |
| 7,148,058 B2 | 12/2006 | Charych et al. |
| 7,247,469 B2 | 7/2007 | Wagner et al. |
| 7,354,721 B2 | 4/2008 | Tchaga |
| 7,466,851 B2 | 12/2008 | Gulati |
| 7,507,480 B2 | 3/2009 | Sugama |
| 7,522,271 B2 | 4/2009 | Sandstrom |
| 7,534,563 B2 | 5/2009 | Hargreaves |
| 7,569,343 B2 | 8/2009 | Marton et al. |
| 7,588,906 B2 | 9/2009 | Brueggemeier et al. |
| 7,622,295 B2 | 11/2009 | Cabezas |
| 7,682,797 B2 | 3/2010 | Thompson et al. |
| 7,682,798 B2 | 3/2010 | Thompson et al. |
| 7,695,919 B2 | 4/2010 | Apel et al. |
| 7,723,125 B2 | 5/2010 | Tchaga |
| 7,884,183 B2 | 2/2011 | Von et al. |
| 7,909,889 B2 | 3/2011 | Charrier et al. |
| 7,993,583 B2 | 8/2011 | Dugan et al. |
| 8,073,626 B2 | 12/2011 | Troup et al. |
| 8,148,141 B2 | 4/2012 | Nokihara et al. |
| 8,242,058 B2 | 8/2012 | Raines et al. |
| RE44,031 E | 2/2013 | Apel et al. |
| 8,969,255 B2 | 3/2015 | Johnston et al. |
| 9,709,558 B2 | 7/2017 | Johnston et al. |
| 9,970,932 B2 | 5/2018 | Woodbury et al. |
| 2003/0003516 A1 | 1/2003 | Robinson et al. |
| 2003/0082579 A1 | 5/2003 | Felgner et al. |
| 2003/0207467 A1 | 11/2003 | Snyder et al. |
| 2004/0038307 A1 | 2/2004 | Lee et al. |
| 2004/0038556 A1 | 2/2004 | French et al. |
| 2004/0048311 A1 | 3/2004 | Ault-Riche et al. |
| 2004/0063902 A1 | 4/2004 | Miranda |
| 2004/0071705 A1 | 4/2004 | Sato et al. |
| 2004/0253636 A1 | 12/2004 | Soloviev et al. |
| 2005/0009204 A1 | 1/2005 | Fang et al. |
| 2005/0048566 A1 | 3/2005 | Delisi et al. |
| 2005/0064395 A1 | 3/2005 | Israel et al. |
| 2005/0255491 A1 | 11/2005 | Lee et al. |
| 2006/0013971 A1 | 1/2006 | Chen et al. |
| 2006/0024677 A1 | 2/2006 | Morris et al. |
| 2006/0052948 A1 | 3/2006 | Gorlach |
| 2006/0121490 A1 | 6/2006 | He |
| 2007/0003954 A1 | 1/2007 | Kodadek et al. |
| 2007/0015172 A1 | 1/2007 | Zhang et al. |
| 2007/0020678 A1 | 1/2007 | Ault-Riche et al. |
| 2007/0099256 A1 | 5/2007 | Sundararajan et al. |
| 2007/0122841 A1 | 5/2007 | Rajasekaran et al. |
| 2008/0026485 A1 | 1/2008 | Hueber et al. |
| 2008/0124719 A1 | 5/2008 | Chung et al. |
| 2008/0188618 A1 | 8/2008 | Greving et al. |
| 2008/0193965 A1 | 8/2008 | Zeng et al. |
| 2008/0207507 A1 | 8/2008 | Lau et al. |
| 2008/0254482 A1 | 10/2008 | Mattoon et al. |
| 2009/0054251 A1 | 2/2009 | O'Connor et al. |
| 2009/0131278 A1 | 5/2009 | Wagner et al. |
| 2009/0142792 A1 | 6/2009 | Robinson et al. |
| 2009/0176664 A1 | 7/2009 | Chu |
| 2010/0035765 A1 | 2/2010 | Kodadek |
| 2010/0064393 A1 | 3/2010 | Berka et al. |
| 2010/0105086 A1 | 4/2010 | Landolfo et al. |
| 2010/0210478 A1 | 8/2010 | Gao et al. |
| 2010/0261205 A1 | 10/2010 | Kakuta et al. |
| 2011/0046015 A1 | 2/2011 | Honda et al. |
| 2011/0065594 A1 | 3/2011 | Thompson et al. |
| 2011/0105366 A1 | 5/2011 | Lebl et al. |
| 2011/0190149 A1 | 8/2011 | Tainsky et al. |
| 2011/0275537 A1 | 11/2011 | Rychlewski et al. |
| 2011/0301057 A1 | 12/2011 | Propheter et al. |
| 2011/0301058 A1 | 12/2011 | Cheng et al. |
| 2011/0319291 A1 | 12/2011 | Vrijbloed et al. |
| 2012/0004130 A1 | 1/2012 | Mattoon et al. |
| 2012/0134920 A1 | 5/2012 | D'Souza et al. |
| 2012/0189702 A1 | 7/2012 | Gupta |
| 2012/0190574 A1 | 7/2012 | Johnston et al. |
| 2012/0238477 A1 | 9/2012 | Albert et al. |
| 2013/0071860 A1 | 3/2013 | Hale et al. |
| 2013/0079250 A1 | 3/2013 | Johnston et al. |
| 2013/0143756 A1 | 6/2013 | Johnston et al. |
| 2013/0310265 A1 | 11/2013 | Menegatti et al. |
| 2014/0087963 A1* | 3/2014 | Johnston ............ G01N 33/6854 506/9 |
| 2014/0135225 A1* | 5/2014 | Crow ................... C12Q 1/6883 506/9 |
| 2014/0342939 A1 | 11/2014 | Cohen et al. |
| 2014/0349888 A1 | 11/2014 | Rajasekaran et al. |
| 2015/0108344 A1 | 4/2015 | Anderson et al. |
| 2015/0119289 A1 | 4/2015 | Chen et al. |
| 2015/0217258 A1 | 8/2015 | Woodbury et al. |
| 2015/0241420 A1 | 8/2015 | Johnston et al. |
| 2016/0041153 A1 | 2/2016 | Brown et al. |
| 2016/0041158 A1 | 2/2016 | Woodbury et al. |
| 2016/0067667 A1 | 3/2016 | Rajasekaran et al. |
| 2016/0131662 A1 | 5/2016 | Kodadek |
| 2017/0030906 A1 | 2/2017 | Mesa et al. |
| 2017/0106344 A1* | 4/2017 | Woodbury ............... C40B 50/18 |
| 2017/0212101 A1 | 7/2017 | Zhu et al. |
| 2020/0064345 A1 | 2/2020 | Sykes et al. |
| 2020/0116715 A1 | 4/2020 | Gerwien et al. |
| 2020/0209236 A1 | 7/2020 | Gerwien et al. |
| 2020/0309774 A1 | 10/2020 | Gerwien et al. |

FOREIGN PATENT DOCUMENTS

| | | |
|---|---|---|
| CN | 102361646 A | 2/2012 |
| CN | 103025890 A | 4/2013 |
| CN | 103776891 A | 5/2014 |
| CN | 104271746 A | 1/2015 |
| EP | 0476014 B1 | 8/1994 |
| EP | 0728520 A1 | 8/1996 |
| EP | 1785726 A1 | 5/2007 |
| JP | 2002540382 A | 11/2002 |
| JP | 2012508011 A | 4/2012 |
| JP | 2012530906 A | 12/2012 |
| JP | 2013188212 A | 9/2013 |
| JP | 2015528912 A | 10/2015 |
| JP | 2016502095 A | 1/2016 |
| WO | WO-9015070 A1 | 12/1990 |
| WO | WO-9118980 A1 | 12/1991 |
| WO | WO-9306121 A1 | 4/1993 |
| WO | WO-9408051 A1 | 4/1994 |
| WO | WO-9512608 A1 | 5/1995 |
| WO | WO-9530642 A1 | 11/1995 |
| WO | WO-9535503 A1 | 12/1995 |
| WO | WO-9609668 A1 | 3/1996 |
| WO | WO-9727329 A1 | 7/1997 |
| WO | WO-0004382 A1 | 1/2000 |
| WO | WO-0156691 A2 | 8/2001 |
| WO | WO-02097051 A2 | 12/2002 |
| WO | WO-03019192 A1 | 3/2003 |
| WO | WO-2004053068 A2 | 6/2004 |
| WO | WO-2005050224 A2 | 6/2005 |
| WO | WO-2007068240 A2 | 6/2007 |
| WO | WO-2007147141 A2 | 12/2007 |
| WO | WO-2008048970 A2 | 4/2008 |
| WO | WO-2008085185 A2 | 7/2008 |
| WO | WO-2008151146 A2 | 12/2008 |
| WO | WO-2009140039 A2 | 11/2009 |
| WO | WO-2010043668 A1 | 4/2010 |
| WO | WO-2010053587 A2 | 5/2010 |
| WO | WO-2010148365 A2 | 12/2010 |
| WO | WO-2011026200 A2 | 3/2011 |
| WO | WO-2011045745 A1 | 4/2011 |
| WO | WO-2011109440 A1 | 9/2011 |
| WO | WO-2011150168 A1 | 12/2011 |
| WO | WO-2012007622 A1 | 1/2012 |
| WO | WO-2012055069 A1 | 5/2012 |

(56) References Cited

FOREIGN PATENT DOCUMENTS

| WO | WO-2014062981 A  | 4/2014  |
|----|------------------|---------|
| WO | WO-2014036312 A3 | 5/2015  |
| WO | WO-2015095136 A1 | 6/2015  |
| WO | WO-2016005295 A1 | 1/2016  |
| WO | WO-2016040703 A1 | 3/2016  |
| WO | WO-2017223116 A2 | 12/2017 |
| WO | WO-2017223117 A1 | 12/2017 |
| WO | WO-2017223116 A3 | 2/2018  |
| WO | WO-2018089554 A1 | 5/2018  |
| WO | WO-2018089556 A1 | 5/2018  |
| WO | WO-2018156808 A2 | 8/2018  |
| WO | WO-2018236838 A2 | 12/2018 |

OTHER PUBLICATIONS

Bombardier et al., Derivation of the SLEDAI, Arthritis and Rheumatism, vol. 35, No. 6, Jun. 1992. (Year: 1992).*
Williams et al., Diagnosis and early detection of CNS-SLE in MRL/lpr micr using peptide microarrays, BMC Immunology, 2014, 15:23, pp. 1-19. (Year: 2014).*
Stafford et al., Immunosignature system for diagnosing cancer, PNAS, Jul. 14, 2014, pp. E3072-E3080. (Year: 2014).*
Cortes et al. Support-vector networks. Machine Learning. 1995; 20:273-297.
Kukreja et al. Comparative study of classification algorithms for immunosignaturing data. BMC Bioinformatics 13:139 (2012).
Lisnevskaia et al. Systemic lupus erythematosus. Lancet 384(9957):1878-88 (2014).
Oglesby et al. Impact of Early Versus Late Systemic Lupus Erythematosus Diagnosis on Clinical and Economic Outcomes. Applied Health Economics & Health Policy 12(2):179-90 (2014).
PCT/US2017/038392 International Search Report and Written Opinion dated Sep. 8, 2017.
Zou et al. Regularization and Variable Selection via the Elastic Net. J R Statist Soc B 67(Part 2):301-320 (2005).
Agarwal, et al. Disregulated expression of the Th2 cytokine gene in patients with intraoral squamous cell carcinoma. Immunol Invest. Feb. 2003;32(1-2):17-30.
Alpert et al., A clinically meaningful metric of immune age derived from high-dimensional longitudinal monitoring. Nature Medicine. 25(3):487-495 (2019). doi: 10.1038/s41591-019-0381-y. Epub Mar. 6, 2019.
Altschul et al. Local alignment statistics. Meth. Enzymol. 266:460-480 (1996).
Anderson, et al. The human plasma proteome: history, character, and diagnostic prospects. Mol Cell Proteomics. Nov. 2002;1(11):845-67.
Andresen et al., Deciphering The Antibodyome Peptide Arrays For Serum Antibody Biomarker Diagnostics, Current Proteomics, 6;1-12 (2009).
Assayag et al. High Resolution Computed Tomography Scoring Systems for Evaluating Interstitial Lung Disease in Systemic Sclerosis Patients. Rheumatology S1:003 (2012).
Bailey. MEME: discovering and analyzing DNA and protein sequence motifs. (2006) Nucleic Acids Res. 34(suppl 2): W369-W373.
Bauer et al., Identification and Quantification of a New Family of Peptide Endocannabinoids (Pepcans) Showing Negative Allosteric Modulation at CB1 Receptors, Journal of Biological Chemistry (2012) 287(44); 36944-36967.
Benjamini e al. Controlling the false discovery rate: a practical and powerful approach to multiple testing. Journal of the Royal Statistical Society. Series B (Methodological), pp. 289-300 (1995).
Berglund, et al. A Genecentric Human Protein Atlas for Express Profiles Based on antibodies. Oct. 1, 2008, Molecular and Cellular Proteomics, 7, pp. 2019-2027.
Bern, C.: Chagas' Disease. N Engl J Med. 373(19): 1881-1882 (2015).
Bern et al.: An estimate of the burden of Chagas disease in the United States. Clin Infect Dis. 49(5): e52-e54 (2009).

Boltz, et al. Peptide microarrays for carbohydrate recognition. Analyst. Apr. 2009;134(4):650-2. doi: 10.1039/b823156g. Epub Feb. 11, 2009.
Borrebaeck. Antibodies in diagnostics—from immunoassays to protein chips. Immunol Today. Aug. 2000;21(8):379-82.
Breitling F. et al. High-density peptide arrays. Mol. BioSyst., vol. 5, pp. 224-234, 2009.
Brown, et al. Statistical methods for analyzing immunosignatures. BMC Bioinformatics. Aug. 19, 2011;12:349. doi: 10.1186/1471-2105-12-349.
Brown, et al. The preclinical natural history of serous ovarian cancer: defining the target for early detection. PLoS Med. Jul. 2009;6(7):e1000114. doi: 10.1371/journal.pmed.1000114. Epub Jul. 28, 2009.
Brusic, et al. Information technologies for vaccine research. Expert Rev Vaccines. Jun. 2005;4(3):407-17.
Buscaglia et al.: The surface coat of the mammal-dwelling infective trypomastigote stage of Trypanosoma cruzi is formed by highly diverse immunogenic mucins. J Biol Chem. 279(16):15860-15869 (2004).
Busch et al.: Virus and antibody dynamics in acute west nile virus infection. J Infect Dis. 198(7): 984-993 (2008).
Butler, et al. The immunochemistry of sandwich ELISAs—VI. Greater than 90% of monoclonal and 75% of polyclonal anti-fluorescyl capture antibodies (CAbs) are denatured by passive adsorption. Mol Immunol. Sep. 1993;30(13):1165-75.
Butler. Solid supports in enzyme-linked immunosorbent assay and other solid-phase immunoassays. Methods. Sep. 2000;22(1):4-23.
Casey, et al. Phage display of peptides in ligand selection for use in affinity chromatography. Methods Mol Biol. 2008;421:111-24.
Cenci, et al. Managing and exploiting stress in the antibody factory. FEBS Lett. Jul. 31, 2007;581(19):3652-7. Epub Apr. 24, 2007.
Cerecedo, et al. Mapping of the IgE and IgG4 sequential epitopes of milk allergens with a peptide microarray-based immunoassay. J Allergy Clin Immunol. Sep. 2008;122(3):589-94. doi: 10.1016/j.jaci.2008.06.040.
Chase et al,. Evaluation of biological sample preparation for immunosignature-based diagnostics. Clinical Vaccine and Immunology. 19(3):352-358 (2012).
Chatelain, E.: Chagas disease research and development: Is there light at the end of the tunnel? Comput Struct Biotechnol J. 15: 98-103 (2016; eCollection 2017).
Chen, et al. Identification of multiple cancer/testis antigens by allogeneic antibody screening of a melanoma cell line library. Proc Natl Acad Sci U S A. Jun. 9, 1998;95(12):6919-23.
Chene, P., Challenges in Design of Biochemical Assays for the Identification of Small Molecules to Target Multiple Conformations of Protein Kinases. Drug Discovery Today, 13(11/12); 522-529 (2008).
Cheng et al.: Immunoblot assay using recombinant antigens as a supplemental test to confirm the presence of antibodies to Trypanosoma cruzi. Clin Vaccine Immunol. 14(4): 355-361 (2007).
Christian, R.B., et al. (1992) Simplified methods for construction, assessment and rapid screening of peptide libraries in bacteriophage. Journal of Molecular Biology 227, 711-718.
Clayton, J.: Chagas disease 101. Nature. 465(7301): S4-S5 (2010).
Cooperman, et al. Cell division rates of primary human precursor B cells in culture reflect in vivo rates. Stem Cells. 2004;22(6):1111-20.
Cretich, et al. Epitope mapping of human chromogranin A by peptide microarrays. Methods Mol Biol. 2009;570:221-32. doi: 10.1007/978-1-60327-394-7_10.
Cretich. Protein and peptide arrays: Recent trends and new directions. (2006) Biomol. Eng. 23: 77-88 (2006).
Crooks, et al. WebLogo: a sequence logo generator. Genome Res. Jun. 2004;14(6):1188-90.
Daver, et al. The usefulness of prostate-specific antigen and prostatic acid phosphatase in clinical practice. Am J Clin Oncol. 1988;11 Suppl 2:S53-60.
De Pablos et al.: Multigene families in Trypanosoma cruzi and their role in infectivity. Infect Immun. 80(7): 2258-2264 (2012).

(56) References Cited

OTHER PUBLICATIONS

De Paz, J.L. et la. Exploration of the use of an acylsulfonamide safety-catch linker for the polymer-supported synthesis of hyaluronic acid oligosaccharides. Carbohydr Res. Mar. 30, 2010;345(5):565-71. Epub Jan. 4, 2010.

De Rycker et al.: Identification of Trypanocidal Activity for Known Clinical Compounds Using a New Trypanosoma cruzi Hit-Discovery Screening Cascade. PLoS Negl Trop Dis. 10(4):e0004584 (2016).

DeLong et al. Comparing the areas under two or more correlated receiver operating characteristic curves: a nonparametric approach. Biometrics (1988); 44(3): 837-845.

Derda, et al. Diversity of phage-displayed libraries of peptides during panning and amplification. Molecules. Feb. 21, 2011;16(2):1776-803. doi: 10.3390/molecules16021776.

Diehnelt, et al. Discovery of high-affinity protein binding ligands—backwards. PLoS One. May 19, 2010;5(5):e10728. doi: 10.1371/journal.pone.0010728.

Draghici. Statistics and Data Analysis for Microarrays Using R and Bioconductor. Chapman & Hall/CRC. 2012.

Engvall, et al. Enzyme-linked immunosorbent assay (ELISA). Quantitative assay of immunoglobulin G. Immunochemistry. Sep. 1971;8(9):871-4.

EP 10790305.6 Extended European Search Report dated Aug. 20, 2013.

European Patent Application No. 13 833992.4 European Search Report dated Apr. 25, 2016.

Falsey, J.R., et al. Peptide and small molecule microarray for high throughput cell adhesion and functional assays. Bioconjugate Chem. (2001) 12, 346-353.

Favoino et al. Autoantibodies recognizing the amino terminal 1-17 segment of CENP-A display unique specificities in systemic sclerosis. PLoS One 8(4):e61453 (2013).

Fodor. Multiplexed biochemical assays with biological chips. Nature 364:555-556 (1993).

Folgori, A., et al. A general strategy to identify mimotopes of pathological antigens using only random peptide libraries and human sera. (1994) EMBO Journal, vol. 13, No. 9, pp. 2236-2243.

Foong, et al. Current advances in peptide and small molecule microarray technologies. Curr Opin Chem Biol. Apr. 2012;16(1-2):234-42. doi: 10.1016/j.cbpa.2011.12.007. Epub Jan. 3, 2012.

Forster, et al. The bulk of the peripheral B-cell pool in mice is stable and not rapidly renewed from the bone marrow. Proc Natl Acad Sci U S A. Jun. 1990;87(12):4781-4.

Frith. Discovering Sequence Motifs with Arbitrary Insertions and Deletions. (2008) PLOS Comput. Blol. 4: e1000071.

Fu et al., Exploring peptide space for enzyme modulators, J. Am. Chem. Soc., Apr. 2010, 6419-6424, vol. 132, No. 18.

Fu, et al. Peptide-modified surfaces for enzyme immobilization. PLoS One. Apr. 8, 2011;6(4):e18692. doi: 10.1371/journal.pone.0018692.

Gallina, et al. Prediction of pathological stage is inaccurate in men with PSA values above 20 ng/mL. Eur Urol. Nov. 2007;52(5):1374-80. Epub Dec. 11, 2006.

Geysen, et al. Use of peptide synthesis to probe viral antigens for epitopes to a resolution of a single amino acid. Proc Natl Acad Sci U S A. Jul. 1984;81(13):3998-4002.

Gomes et al.: Diagnosis of Chagas disease: what has been achieved? What remains to be done with regard to diagnosis and follow up studies? Mem Inst Oswaldo Cruz. 104 Suppl 1: 115-121 (2009).

Granjon et al.: Development of a Novel Multiplex Immunoassay Multi-cruzi for the Serological Confirmation of Chagas Disease. PLoS Negi Trap Dis. 10(4): e0004596 (2016).

Greving, et al. High-throughput screening in two dimensions: binding intensity and off-rate on a peptide microarray. Anal Biochem. Jul. 1, 2010;402(1):93-5. doi: 10.1016/j.ab.2010.03.002. Epub Mar. 6, 2010.

Greving, et al. Thermodynamic additivity of sequence variations: an algorithm for creating high affinity peptides without large libraries or structural information. PLoS One. Nov. 11, 2010;5(11):e15432. doi: 10.1371/journal.pone.0015432.

Gupta, N., et al. Engineering a synthetic ligand for tumor necrosis factor-alpha.(2011) Bioconjugate Chemistry, vol. 22, pp. 1473-1478.

Haft et al.: Human orthologs of yeast vacuolar protein sorting proteins Vps26, 29, and 35: assembly into multimeric complexes. Mol Biol Cell. 11(12): 4105-4116 (2000).

Halperin et al. Exploring Antidbody Recognition of Sequence Space Through Random-Sequence Peptide Microarrays. Molecular & Cellular Proteomics 10.3:1-10 (2011).

Hanash, S. Disease proteomics. (Mar. 2003) Nature vol. 422, pp. 226-232.

Hao, et al. Homeostasis of peripheral B cells in the absence of B cell influx from the bone marrow. J Exp Med. Oct. 15, 2001;194(8):1151-64.

Hecker et al. Computational analysis of high-density peptide microarray data with application from systemic sclerosis to multiple sclerosis. Autoimmunity Reviews 11:180-190 (2012).

Henikoff et al. Amino acid substitution matrices from protein blocks. PNAS USA 89(22):10915-10919 (1992).

Hori, et al. Mathematical model identifies blood biomarker-based early cancer detection strategies and limitations. Sci Transl Med. Nov. 16, 2011;3(109):109ra116. doi: 10.1126/scitranslmed.3003110.

Huang, et al. MIMOX: a web tool for phage display based epitope mapping. BMC Bioinformatics. Oct. 12, 2006;7:451.

Hughes, et al. Immunosignaturing can detect products from molecular markers in brain cancer. PLoS One. 2012;7(7):e40201. doi: 10.1371/journal.pone.0040201. Epub Jul. 16, 2012.

International Application No. PCT/US2018/019287 International Search Report and Written Opinion dated Aug. 10, 2018.

International search report and written opinion dated Oct. 22, 2012 for PCT/US2012/036631.

International search report and written opinion dated Feb. 3, 2014 for PCT/US2013/057373.

International search report and Written opinion dated Apr. 28, 2015 for PCT/US2013/057373.

International search report dated Dec. 20, 2013 for PCT/US2013/065541.

Issa et al.: Antitrypanosomal agents: treatment or threat? Lancet. 376(9743): 768 (2010).

Janeway, et al. Immunobiology: The Immune System in Health and Disease. Current Biology Limited. 1997.

Jollymore, M. "Virus research aims to prevent or reverse immune-system aging," Nova Scotia Health Authority Research Annual Report 2017, Feb. 21, 2018, pp. 1-2. Retrieved from the Internet:http://www.nshealth.ca/news/virus-research-aims-prevent-or-reverse-immune-system-aging Oct. 15, 2019.

Jonassen. Efficient discovery of conserved patterns using a pattern graph. (1997) Comput. Appl. Biosci. 13: 509-22.

Keating et al.: Inflammatory and cardiac biomarkers are differentially expressed in clinical stages of Chagas disease. Int J Cardiol. 199: 451-459 (2015).

Kroening, et al. Autoreactive antibodies raised by self derived de novo peptides can identify unrelated antigens on protein microarrays. Are autoantibodies really autoantibodies? Exp Mol Pathol. Jun. 2012;92(3):304-11. doi: 10.1016/j.yexmp.2012.03.002. Epub Mar. 8, 2012.

Kukreja, M., et al. Immunosignaturing Microarrays Distinguish Antibody Profiles of Related Pancreatic Diseases. (2012) Journal of Proteomics & Bioinformatics, vol. S6, pp. 001.

Lander et al.: Localization and developmental regulation of a dispersed gene family 1 protein in Trypanosoma cruzi. Infect Immun. 78(1): 231-240 (2010).

Legutki et al., A general method for characterization of humoral immunity induced by a vaccine or infection. Vaccine. 28(28):4529-4537 (2010).

Legutki, J.B., et al. Scalable high-density peptide arrays for comprehensive health monitoring. Nature Communications, vol. 5, p. 4785; (Sep. 3, 2014).

(56) References Cited

OTHER PUBLICATIONS

Lewczuk, et al. Amyloid beta peptides in plasma in early diagnosis of Alzheimer's disease: A multicenter study with multiplexing. Exp Neurol. Jun. 2010;223(2):366-70. doi: 10.1016/j.expneurol.2009.07.024. Epub Aug. 5, 2009.
Lin, et al. Development of a novel peptide microarray for large-scale epitope mapping of food allergens. J Allergy Clin Immunol. Aug. 2009;124(2):315-22, 322.e1-3. doi: 10.1016/j.jaci.2009.05.024. Epub Jul. 3, 2009.
Liu et al. Towards proteome-wide production of monoclonal antibody by phage display. J Mol Biol. 315(5):1063-1073 (2002).
Liu, R., et al. Combinatorial peptide library methods for immunobiology research. (2003) Experimental Hematology vol. 31, pp. 11-30.
Lorenz, P., et al. Probing the epitope signatures ofIgG antibodies in human serum from patients with autoimmune disease. (2009) Methods in Molecular Biology, Epitope Mapping Protocls, vol. 524, pp. 247-258.
Mackey, et al. Getting more from less: algorithms for rapid protein identification with multiple short peptide sequences. Mol Cell Proteomics. Feb. 2002;1(2):139-47.
Manson et al., Systemic Lupus Erythematosus. Orphanet J Rare Dis 1:6 (2006).
McCullough et al.: The nation's changing blood supply system. JAMA. 269(17): 2239-2245 (1993).
McDade, et al. What a Drop Can Do: Dried Blood Spots as a Minimally Invasive Method for Integrating Biomarkers Into Population-Based Research, Demography 44(4):899-925 (2007).
Medsger et al. Assessment of disease severity and prognosis. Clin Exper Rheumatol 21:S42-S46 (2003).
Merbl, et al. A Systems Immunology Approach to the Host-Tumor Interaction: Large-Scale Patterns of Natural Autoantibodies Distinguish Healthy and Tumor-Bearing Mice. PLoS One vol. 4, Issue 6, p. e6053. Jun. 2009.
Mestas, et al., Of Mice and Not Men: Differences Between Mouse and Human Immunology, The Journal of Immunology, 172;2731-2738 (2004).
Min et al. Peptide arrays: towards routine implementation. Current Opinion in Chemical Biology vol. 8, pp. 554-558, 2004.
Miseta, Attila et al. Relationship Between the Occurrence of Cysteine in Proteins and the Complexity of Organisms. (2000) Mol. Biol. Evol., vol. 17, pp. 1232-1239.
Mitra et al., Self-assembly of cyclic metal-DNA nanostructures using ruthenium tris(bipyridine)-branchedoligonucleotides. Agnewandte Chemie. 43(43):5804-5808 (2004).
Mohan, S., et al. Association energetics of cross-reactive and specific antibodies. (Feb. 17, 2009) Biochemistry vol. 48, No. 6, pp. 1390-1398.
Moller, et al. DNA probes on chip surfaces studied by scanning force microscopy using specific binding of colloidal gold. Nucleic Acids Res. Oct. 15, 2000;28(20):E91.
Morales Betanzos, et al. Bacterial glycoprofiling by using random sequence peptide microarrays. Chembiochem. Mar. 23, 2009;10(5):877-88. doi: 10.1002/cbic.200800716.
Moreau, et al. Discontinuous epitope prediction based on mimotope analysis. Bioinformatics. May 1, 2006;22(9):1088-95. Epub Jan. 24, 2006.
Morillo et al.: Randomized Trial of Benznidazole for Chronic Chagas' Cardiomyopathy. N Engl J Med. 373(14): 1295-1306 (2015).
Moudgil et al. Cytokines in autoimmunity: Role in induction, regulation, and treatment, J. Interferon & Cytokine Res, 31(10):695-703 (2011).
Navalkar, K.A. et al. Peptide based diagnostics: Are random-sequence peptides more useful than tiling proteome sequences? Journal of Immunological Methods, vol. 417, pp. 10-21 (2015).
Neufing et al., Exposure and Binding of Selected Immunodominant La/SSB Epitopes on Human Apoptotic Cells. Arthritis Rheum 52(12): 3934-3942 (2005).

Neuman De Vegvar, et al. Microarray profiling of antiviral antibodies for the development of diagnostics, vaccines, and therapeutics. (2004) Clinical Immunology, vol. 111 pp. 196-201.
No Author. AFFYMETRIX, GeneChip Human Genome Arrays Data Sheet, pp. 1-4 (2003).
No Author. NSB9 Amine Slide, NSB POSTECH, 2007, http://www.nsbpostech.com/2007/products/slide.html .
No Author. Pubchem CID 110154. Created: Aug. 8, 2005. Date accessed: Feb. 26, 2018, pp. 1-15.
Nobrega, A., et al. Functional diversity and clonal frequencies of reactivity in the available antibody repertoire. (1998) European Journal of Immunology vol. 28, pp. 1204-1215.
Office action dated Apr. 8, 2013 for U.S. Appl. No. 13/379,080.
Office action dated Sep. 12, 2014 for U.S. Appl. No. 13/379,080.
Office action dated Sep. 20, 2013 for U.S. Appl. No. 13/624,332.
Office action dated Sep. 20, 2013 for U.S. Appl. No. 13/624,386.
Office action dated Oct. 3, 2013 for U.S. Appl. No. 13/379,080.
Oliveira et al.: Perspectives in Chagas disease treatment. Glob Heart. 10(3): 189-192 (2015).
Panicker, R.C., et al. Recent advances in peptide-based microarray technologies. (2004) Combinatorial Chemistry & High Throughput Screening vol. 7, pp. 547-556.
PCT/US2017/038391 International Search Report and Written Opinion dated Dec. 11, 2017.
PCT/US2017/038391 Invitation to Pay Additional Fees dated Oct. 5, 2017.
PCT/US2017/060721 International Search Report and Written Opinion dated Feb. 26, 2018.
PCT/US2017/060724 International Search Report and Written Opinion dated Mar. 13, 2018.
PCT/US2018/019287 International Preliminary Report on Patentability dated Sep. 6, 2019.
PCT/US2018/038240 International Preliminary Report on Patentability dated Dec. 24, 2019.
PCT/US2018/038240 International Search Report and Written Opinion dated Dec. 27, 2018.
PCT/US2019/017326 International Search Report and Written Opinion dated Jun. 3, 2019.
PCT/US2019/017326 Invitation to Pay Additional Fees dated Apr. 12, 2019.
PCT/US2019/028791 International Search Report and Written Opinion dated Oct. 15, 2019.
Pecoul et al.: The BENEFIT Trial: Where Do We Go from Here? PLoS Negl Trop Dis. 10(2): e0004343 (2016).
Perez et al.: Chagas disease: the challenge of polyparasitism? Trends Parasitol. 30(4): 176-182 (2014).
Perez-Gordo, et al. Epitope mapping of Atlantic salmon major allergen by peptide microarray immunoassay. Int Arch Allergy Immunol. 2012;157(1):31-40. doi: 10.1159/000324677. Epub Sep. 5, 2011.
Pinazo et al.: Biological markers for evaluating therapeutic efficacy in Chagas disease, a systematic review. Expert Rev Anti Infect Ther. 12(4): 479-496 (2014).
Pinazo et al.: Immunosuppression and Chagas disease: a management challenge. PLoS Negl Trop Dis. 7(1): e1965 (2013).
Praast et al.: Evaluation of the Abbott Architect Chagas prototype assay. Diagn Microbiol Infect Dis. 69(1): 74-81 (2011).
Price et al., On silico peptide microarrays for high-resolution mapping of antibody epitopes and diverse protein-protein interactions, Nat Med, Sep. 2012, 1434-40, vol. 18, No. 9.
Quackenbush, et al. Computational Analysis of Microarray Data, Nature Reviews, 2;418-427 (2001).
Quintana, et al., Antigen-chip technology for accessing global information about the state of the body. 2006 Lupus vol. 15, pp. 428-430.
Quintana, et al. The Natural autoantibody repertoire and autoimmune disease. Biomedicine & Pharmacotherapy vol. 58 (2004) pp. 276-281.
Rassi et al.: Chagas disease. Lancet. 375(9723): 1388-1402 (2010).
Reddy, et al. Identification of candidate IgG biomarkers for Alzheimer's disease via combinatorial library screening. Cell. Jan. 7, 2011;144(1):132-42. doi: 10.1016/j.cell.2010.11.054.

(56) References Cited

OTHER PUBLICATIONS

Reddy, et al., Protein fingerprinting in complex mixtures with peptoid microarrays. Proc. Of The Nat'l Academy of Sciences, Nat'l Academy of Sciences, US, 102(36):12672-12677 Sep. 2005.
Reineke, et al., Epitope Mapping Protocols, Method in Molecular Biology 524, 2nd Edition, Huma Press. 1-447 (2009).
Reineke, et al. Identification Of Distinct Antibody Epitopes and mimotopes from a peptide array of 5520 randomly generated sequences. Journal of Immunological Methods vol. 267 (2002) pp. 37-51.
Remesar et al.: Bimodal distribution of Trypanosoma cruzi antibody levels in blood donors from a highly endemic area of Argentina: what is the significance of low-reactive samples? Transfusion. 55(10): 2499-2504 (2015).
Restrepo, et al. Application of immunosignatures to the assessment of Alzheimer's disease. Ann Neurol. Aug. 2011;70(2):286-95. doi: 10.1002/ana.22405.
Rigoutsos. In Silico Pattern-Based Analysis of the Human Cytomegalovirus Genome. (1998) Bioinformatics 14: 55-67.
Roobol. Contemporary role of prostate cancer gene 3 in the management of prostate cancer. Curr Opin Urol. May 2011;21(3):225-9. doi: 10.1097/MOU.0b013e328344939c.
Shreffler, W.G., et al. IgE and IgG4 epitope mapping by microarray immunoassay reveals the diversity of immune response to the peanut allergen, Ara h 2. (2005) J Allergy Clin Immunol vol. 116, No. 4, pp. 893-899.
Sodre et al.: Proteomic map of Trypanosoma cruzi CL Brener: the reference strain of the genome project. Arch Microbiol. 191(2): 177-184. Epub Nov. 11, 2008. (2009).
Stafford, et al. Physical characterization of the "immunosignaturing effect". Mol Cell Proteomics. Apr. 2012;11(4):M111.011593. doi: 10.1074/mcp.M111.011593. Epub Jan. 18, 2012.
Stafford P and Johnston,Microarray technology displays the complexities of the humoral immune response. Expert Rev. Mol. Diagn. vol. 11, No. 1, pp. 5-8, Jan. 2011.
Stafford, P., et al Immunosignature system for diagnosis of cancer. PNAS, vol. 111, No. 30; pp. E3072-E3080 (Jul. 14, 2014).
States et al. Improved sensitivity of nucleic acid database searches using application-specific scoring matrices. Methods 3:66-70 (1991).
Steverding, D.: The history of Chagas disease. Parasit Vectors. 7: 317 (2014).
Sulzer, et al. Memory in idiotypic networks due to competition between proliferation and differentiation. Bull Math Biol. Nov. 1993;55(6):1133-82.
Szardenings, M. Phage display of random peptide libraries: applications, limits, and potential. (2003) Journal of Receptors and Signal Transduction, vol. 23, No. 4, pp. 307-349.
Tan et al. Autoantibodies to fibrillin 1 in systemic sclerosis: ethnic differences in antigen recognition and lack of correlation with specific clinical features or HLA alleles. Arthritis Rheum 43(11):2464-71 (2000).
Tang et al., Current Developments in SELDI Affinity Technology, Mass Spectrometry Reviews 23;34-44 (2004).
Tedesco, et al. A new strategy for the early diagnosis of rheumatoid arthritis: a combined approach. Autoimmun Rev. Jan. 2009;8(3):233-7. doi: 10.1016/j.autrev.2008.07.031. Epub Aug. 15, 2008.
Thompson, et al. Prostate-specific antigen in the early detection of prostate cancer. CMAJ. Jun. 19, 2007;176(13):1853-8.
Thorpe, I.F., and Brooks, C.L., Molecular evolution of affinity and flexibility in the immune system. (May 22, 2007) PNAS vol. 104, No. 21, pp. 8821-8826.
Tobler et al.: Evaluation of a new enzyme-linked immunosorbent assay for detection of Chagas antibody in US blood donors. Transfusion. 47(1): 90-96 (2007).
Uhlen, M., et al. Generation and validation of affinity reagents on a proteome-wide level. (2009) Journal of Molecular Recognition, vol. 22, pp. 57-64.
United States Patent and Trademark Office, Subject Matter Eligibility Examples: Life Sciences, Subject Matter Eligibility Update, 2016, 1-31.

U.S. Appl. No. 13/379,080 Final Office Action dated Jul. 21, 2015.
U.S. Appl. No. 13/379,080 Final Office action dated Apr. 8, 2013.
U.S. Appl. No. 13/379,080 Final Office action dated Oct. 3, 2013.
U.S. Appl. No. 13/379,080 Final Office action dated Sep. 12, 2014.
U.S. Appl. No. 13/379,080 Office Action dated Aug. 4, 2016.
U.S. Appl. No. 13/379,080 Office action dated Oct. 11, 2012.
U.S. Appl. No. 13/624,332 Final action dated Sep. 20, 2013.
U.S. Appl. No. 13/624,332 Final Office Action dated Feb. 28, 2018.
U.S. Appl. No. 13/624,332 Non-Final Office Action dated Oct. 3, 2017.
U.S. Appl. No. 13/624,332 Office Action dated Feb. 8, 2016.
U.S. Appl. No. 13/624,332 Office action dated Jan. 22, 2013.
U.S. Appl. No. 13/624,332 Office Action dated Jul. 18, 2016.
U.S. Appl. No. 13/624,386 Final action dated Sep. 20, 2013.
U.S. Appl. No. 13/624,386 Notice of Allowance dated Mar. 13, 2017.
U.S. Appl. No. 13/624,386 Office action dated Jan. 23, 2013.
U.S. Appl. No. 13/624,386 Office Action dated Jan. 7, 2016.
U.S. Appl. No. 13/624,386 Office Action dated Jul. 25, 2016.
U.S. Appl. No. 13/683,778 Notice of Allowance dated Nov. 24, 2014.
U.S. Appl. No. 13/683,778 Office Action dated Oct. 1, 2013.
U.S. Appl. No. 14/014,168 Final Office Action dated Sep. 18, 2017.
U.S. Appl. No. 14/014,168 Office Action dated Feb. 21, 2017.
U.S. Appl. No. 14/014,168 Office Action dated Jan. 6, 2016.
U.S. Appl. No. 14/424,022 Final Office Action dated Sep. 7, 2018.
U.S. Appl. No. 15/621,877 Non-Final Office Action dated Sep. 13, 2018.
U.S. Appl. No. 13/624,386 Office Action dated Nov. 28, 2016.
U.S. Appl. No. 14/014,168 Final Office Action dated Sep. 1, 2016.
Usami, et al. The effect of pH, hydrogen peroxide and temperature on the stability of human monoclonal antibody. J Pharm Biomed Anal. Jun. 1996;14(8-10):1133-40.
Viotti et al.: Long-term cardiac outcomes of treating chronic Chagas disease with benznidazole versus no treatment: a nonrandomized trial. Ann Intern Med. 144(10): 724-734 (2006).
Viotti et al.: Side effects of benznidazole as treatment in chronic Chagas disease: fears and realities. Expert Rev Anti Infect Ther. 7(2): 157-163 (2009).
Volk, et al. The accuracy of primary care patients' self-reports of prostate-specific antigen testing. Am J Prev Med. Jan. 2002;22(1):56-8.
Wang et al., Plasma Autoantibodies Associated With Basal-like Breast Cancers. Cancer Epidemiol Biomarkers Prev 24:(9): 1332-1340 (2015).
Wang, Y., et al. Detection of Mammary Tumor Virus ENV Gene-like Sequences in Human Breast Cancer. (Nov. 15, 1995) Cancer Research vol. 55, pp. 5173-5179.
Waterboer et al., Dried Blood Spot Samples For Seroepidemiology of Infections With Human Papillomaviruses, Helicobacter pylori, Hepatitis C Virus, and JC Virus, Cancer, Epidemiology, Biomarkers and Prevention, 2011, 21 (2), 288-293.
Yang, et al. Segmentation and intensity estimation for microarray images with saturated pixels. BMC Bioinformatics. Nov. 30, 2011;12:462. doi: 10.1186/1471-2105-12-462.
Zhou, Z.H., et al. Properties and function of polyreactive antibodies and polyreactive antigen-binding B cells. (Dec. 2007) J. Autoimmun. vol. 29, No. 4, pp. 219-228.
Zundel, et al. Development and evaluation of an enzyme-linked immunoassay for the prostate: specific antigen utilizing two monoclonal antibodies. Urol Res. 1990;18(5):327-30.
Carmona et al., Towards High-throughput Immunomics for Infectious Diseases: Use of Next-generation Peptide Microarrays for Rapid Discovery and Mapping of Antigenic Determinants. Mol Cell Proteomics 14(7):1871-1884 (2015).
Choung et al., Determination of B-Cell Epitopes in Patients with Celiac Disease: Peptide Microarrays. Plos One 11(1): e014777 (2016).

(56) References Cited

OTHER PUBLICATIONS

Cooley et al., High throuphut selection of effective serodiagnostics for Trypanosoma cruzi infection. PLoS Negl Trop Dis 2(10):e316 (2008).

European Application No. 17816082.6 Extended European Search Report dated Apr. 9, 2020.

European Application No. 18821115 Search Report dated Apr. 9, 2021.

European Patent Application No. 18757099 Search Report dated Jan. 18, 2021.

Jeong JS, Jiang L, Albino E, et al., Rapid identification of monospecific monoclonal antibodies using a human proteome microarray, Mol Cell Proteomics, 2012;11(6):O111.016253. doi:10.1074/mcp.O111.016253.

Sokolove et al., Development and deployment of antigen arrays for investigation of B-cell specificity in autoimmune disease. Frontiers in Bioscience E4: 320-330 (2012).

Tarasow et al., Immunosignature Autoantibody Profiles Provide Mechansistic Insight into Systemic Lupus Erythematosus and Differentiation from Symptomatically Overlapping Diseases. Retrieved from http://www.healthtell.com/wp-content/uploads/2018/06/5-HealthTell_ACR2017_poster_SLE (2017).

U.S. Appl. No. 16/312,131 Non-Final Office Action dated May 12, 2021.

Van Bon et al.: Proteome-wide analysis and CXCL4 as a biomarker in systemic sclerosis. N Engl J Med. 370(5):433-443 (2014).

Xiang et al.: Comprehensive investigation of disease-specific short peptides in sera from patients with systemic sclerosis: complement C3f-des-arginine, detected predominantly in systemic sclerosis sera, enhances proliferation of vascular endothelial cells. Arthritis Rheum. 56(6):2018-2030 (2007).

U.S. Appl. No. 16/312,131 Final Office Action dated Jan. 5, 2022.

Zingaretti et al.: Identification of new autoantigens by protein array indicates a role for IL4 neutralization in autoimmune hepatitis. Mol Cell Proteomics. 11(12):1885-1897 doi:10.1074/mcp.M112.018713 (2012).

Fielden et al.: GP3: GenePix post-processing program for automated analysis of raw microarray data. Bioinformatics May 2002;18(5):771-773 doi:10.1093/bioinformatics/18.5.771 (2002).

Fiorentiono et al.: PUF60: a prominent new target of the autoimmune response in dermatomyositis and Sjögren's syndrome. Ann Rheum Dis. 75(6):1145-1151 (2016).

Ohyama et al.: Proteomic profiling of antigens in circulating immune complexes associated with each of seven autoimmune diseases. Clin Biochem. 48(3):181-185 doi:10.1016/j.clinbiochem.2014.11.008 (2015).

U.S. Appl. No. 16/312,131 Non-Final Office Action dated Sep. 23, 2022.

U.S. Appl. No. 16/488,078 Non-Final Office Action dated Apr. 20, 2023.

\* cited by examiner

FIG. 1A

Physicians Global Assessment

| 0 | 1 | 2 | 3 |
|---|---|---|---|
| None | Mild | Med | Severe |

SLEDAI SCORE

Check box: If descriptor is present at the time of visit or in the proceeding 10 days

| Wt | Present | Descriptor | Definition |
|---|---|---|---|
| 8 | ☐ | Seizure | Recent onset. Exclude metabolic, infectious or drug cause |
| 8 | ☐ | Psychosis | Altered ability to function in normal activity due to severe disturbance in the perception of reality. Include hallucinations, incoherence, marked loose associations, impoverished thought content, marked illogical thinking, bizarre, disorganized, or catatonic behavior. Excluded uremia and drug causes. |
| 8 | ☐ | Organic Brain Syndrome | Altered mental function with impaired orientation memory or other intelligent function, with rapid onset fluctuating clinical features. Include clouding of consciousness with reduced capacity to focus, and inability to sustain attention to environment, plus at least two of the following: perceptual disturbance, incoherent speech, insomnia or daytime drowsiness, or increased or decreased psychomotor activity. Exclude metabolic, infectious or drug causes. |
| 8 | ☐ | Visual Disturbance | Retinal changes of SLE. Include cytoid bodies, retinal hemorrhages, serious exodate or hemorrhages in the choroids, or optic neuritis. Exclude hypertension, infection, or drug causes. |
| 8 | ☐ | Cranial Nerve Disorder | New onset of sensory or motor neuropathy involving cranial nerves. |
| 8 | ☐ | Lupus Headache | Severe persistent headache: may be migrainous, but must be non-responsive to narcotic analgesia. |
| 8 | ☐ | CVA | New onset of cerebrovascular accident(s). Exclude arteriosclerosis |
| 8 | ☐ | Vasculitis | Ulceration, gangrene, tender finger nodules. periungual, infarction, splinter hemorrhages, or biopsy or angiogram proof of vasculitis |
| 4 | ☐ | Arthritis | More than 2 joints with pain and signs of inflammation (i.e. tenderness, swelling. or effusion). |
| 4 | ☐ | Myositis | Proximal muscle aching/weakness, associated with elevated creatine phosphokinase/adolase or electromyogram changes or a biopsy showing myositis. |
| 4 | ☐ | Urinary Casts | Heme-granular or red blood cell casts |
| 4 | ☐ | Hematuria | >5 red blood cells/high power field. Exclude stone, infection or other cause. |
| 4 | ☐ | Proteinuria | >0.5 gm/24 hours. New onset or recent increase of more than 0.5 gm/24 hours |
| 4 | ☐ | Pyuria | >5 white blood cells/high power field. Exclude infection. |
| 2 | ☐ | New Rash | New onset or recurrence of inflammatory type rash. |
| 2 | ☐ | Alopecia | New onset or recurrence of abnormal, patchy or diffuse loss of hair. |
| 2 | ☐ | Mucosal Ulcers | New onset or recurrence of oral or nasal ulcerations |

FIG. 1B

| 2 | ☐ | Pleurisy | Pleuritic chest pain with pleural rub or effusion, or pleural thickening. |
|---|---|---|---|
| 2 | ☐ | Pericarditis | Pericardial pain with at least 1 of the following: rub, effusion, or electrocardiogram confirmation. |
| 2 | ☐ | Low Complement | Decrease in CH50, C3, or C4 below the lower limit of normal for testing laboratory. |
| 2 | ☐ | Increased DNA binding | >25% binding by Farr assay or above normal range for testing laboratory. |
| 1 | ☐ | Fever | >38°C. Exclude infectious cause |
| 1 | ☐ | Thrombocytopenia | <100,000 platelets/mm3 |
| 1 | ☐ | Leukopenia | <3,000 White blood cell/mm3. Exclude drug causes. |

_____ TOTAL SCORE (Sum of weights next to descriptors marked present)

| Mild or Moderate Flare ☐ | Severe Flare ☐ |
|---|---|
| ☐ Change in SLEDAI > 3 points | ☐ Change in SLEDAI > 12 |
| ☐ New/worse discoid, photosensitive, profundus, cutaneous vasculitis, bullous lupus<br>Nasopharyngeal ulcers<br>Pleuritis<br>Pericarditis<br>Arthritis<br>Fever (SLE) | ☐ New/worse CNS-SLE<br>Vasculius<br>Nephritis<br>Myositis<br>Pk < 60,000<br>Home anemia: Hb <7% or decrease in Hb > 3%<br>Requiring: double prednisone<br>Prednisone >0.5 mg/kg/day hospitalization |
| ☐ Increase in Prednisone, but not to >0.5 mg/kg/day | ☐ Prednisone >0.5 mg/kg/day |
| ☐ Added NSAID or Plaquenil | ☐ New Cytoxan, Azathioprine, Methotrexate, Hospitalization (SLE) |
| ☐ >1.0 Increase in PGA, but not to more than 2.5 | ☐ Increase in PGA to > 2.5 |

| SLEDAI | 0 | 1-3 | 4-5 | 6-7 | 8-9 | 10-11 | 12-15 | 15-27 |
|---|---|---|---|---|---|---|---|---|
| first | 49 | 23 | 14 | 20 | 19 | 15 | 25 | 18 |
| later | 53 | 13 | 17 | 20 | 32 | 13 | 14 | 11 |

FIG. 13A

| motif | n | n.lib | enrich | p | fdr | padj.holm | Pr_seqs.motif | PLR |
|---|---|---|---|---|---|---|---|---|
| K | 850 | 62082 | 2.52962046 | 1.41E-145 | 5.63E-145 | 5.63E-145 | 0.01369157 | 2.47787105 |
| R | 795 | 63785 | 2.30277077 | 6.62E-115 | 1.32E-114 | 1.99E-114 | 0.01246375 | 2.2528576 |
| H.K | 84 | 2524 | 6.10780767 | 1.55E-38 | 1.41E-36 | 1.41E-36 | 0.03328051 | 6.14508197 |
| R.K | 87 | 2758 | 5.81149826 | 2.52E-38 | 2.37E-36 | 2.37E-36 | 0.0315446 | 5.81411456 |
| RR | 81 | 2464 | 6.03308901 | 7.65E-37 | 3.29E-35 | 6.89E-35 | 0.03287338 | 6.06735208 |
| RK | 79 | 2345 | 6.18272118 | 1.08E-36 | 3.29E-35 | 9.65E-35 | 0.0336887 | 6.22308032 |
| KR | 123 | 5930 | 3.80667531 | 2.43E-35 | 5.53E-34 | 2.14E-33 | 0.02074199 | 3.78086792 |
| HR | 77 | 2470 | 5.72122713 | 1.37E-33 | 2.49E-32 | 1.19E-31 | 0.03117409 | 5.74362725 |
| RH | 172 | 6470 | 3.46059653 | 2.54E-31 | 3.86E-30 | 2.19E-29 | 0.01885626 | 3.4305293 |
| H | 563 | 65939 | 1.57749568 | 3.36E-31 | 4.47E-31 | 6.71E-31 | 0.00853819 | 1.53719255 |
| K..K | 73 | 2501 | 5.47277836 | 1.55E-30 | 1.43E-28 | 1.43E-28 | 0.02918832 | 5.36676277 |
| RG | 98 | 4727 | 3.80483555 | 2.05E-28 | 2.66E-27 | 1.74E-26 | 0.02073197 | 3.77900194 |
| R.R | 73 | 2789 | 4.82211393 | 1.74E-27 | 8.20E-26 | 1.62E-25 | 0.02617426 | 4.79768041 |
| K.K | 71 | 2686 | 4.86984863 | 5.09E-27 | 1.47E-25 | 4.68E-25 | 0.02643336 | 4.84646272 |
| K.R | 73 | 2850 | 4.71890378 | 6.26E-27 | 1.47E-25 | 5.70E-25 | 0.02561404 | 4.69229384 |
| H.K | 71 | 2779 | 4.7068778 | 3.60E-26 | 6.77E-25 | 3.24E-24 | 0.02554876 | 4.68002216 |
| K..G | 99 | 5512 | 3.36763238 | 1.27E-24 | 4.50E-23 | 1.15E-22 | 0.01796081 | 3.26464068 |
| R..K | 64 | 2434 | 4.93012683 | 1.47E-24 | 4.50E-23 | 1.32E-22 | 0.02629417 | 4.82025316 |
| R..R | 57 | 1942 | 5.52507679 | 1.66E-24 | 1.41E-22 | 1.41E-22 | 0.02935118 | 5.39761273 |
| K....G | 78 | 3846 | 3.78255433 | 3.62E-24 | 3.08E-22 | 3.08E-22 | 0.02028081 | 3.69506369 |
| H.R | 68 | 2810 | 4.45826331 | 7.61E-24 | 1.19E-22 | 6.77E-22 | 0.02419929 | 4.42669584 |
| KG | 85 | 4297 | 3.63035412 | 1.53E-23 | 1.74E-22 | 1.29E-21 | 0.01978124 | 3.60220798 |
| KH | 98 | 5687 | 3.1625563 | 1.10E-22 | 1.04E-21 | 9.15E-21 | 0.01723228 | 3.12989801 |
| KK | 68 | 2534 | 4.56277818 | 1.14E-22 | 1.04E-21 | 9.37E-21 | 0.02486188 | 4.5509915 |
| K...K | 47 | 1441 | 6.11926437 | 1.43E-22 | 1.32E-20 | 1.32E-20 | 0.03261624 | 6.01829268 |
| K.G | 107 | 6718 | 2.93431612 | 2.48E-22 | 3.33E-21 | 2.18E-20 | 0.01592736 | 2.88904856 |
| R.H | 65 | 2863 | 4.18268472 | 1.92E-21 | 2.26E-20 | 1.67E-19 | 0.02270346 | 4.14671194 |
| K..G | 88 | 5075 | 3.26406887 | 2.14E-21 | 9.08E-20 | 1.79E-19 | 0.0173399 | 3.14978945 |
| R.R | 60 | 2521 | 4.46248836 | 4.94E-21 | 1.14E-19 | 4.40E-19 | 0.02380008 | 4.35188948 |
| K..R | 60 | 2593 | 4.33857815 | 1.88E-20 | 3.45E-19 | 1.65E-18 | 0.02313922 | 4.22818792 |
| H..K | 57 | 2392 | 4.46799185 | 4.43E-20 | 6.79E-19 | 3.85E-18 | 0.02382943 | 4.35738758 |
| K....G | 75 | 4409 | 3.19143868 | 2.18E-18 | 1.00E-16 | 1.98E-16 | 0.01701066 | 3.08894785 |
| R....G | 75 | 4448 | 3.16345619 | 3.48E-18 | 1.07E-16 | 3.13E-16 | 0.01686151 | 3.0613995 |
| K..R | 49 | 1997 | 4.61881645 | 3.79E-18 | 1.07E-16 | 3.14E-16 | 0.02453681 | 4.48998973 |
| R.....G | 89 | 3967 | 3.24404405 | 4.38E-18 | 1.86E-16 | 3.68E-16 | 0.0173935 | 3.15969728 |
| R...K | 47 | 1862 | 4.75150149 | 6.19E-18 | 1.32E-16 | 5.08E-16 | 0.02524168 | 4.62231405 |
| R.G | 99 | 7019 | 2.59850211 | 2.49E-17 | 2.60E-16 | 2.14E-15 | 0.01410457 | 2.55368497 |

FIG. 13B

| motif | n | n.lib | enrich | p | fdr | padj.holm | Pr_seqs.motif | PLR |
|---|---|---|---|---|---|---|---|---|
| R..G | 81 | 5272 | 2.88076816 | 1.40E-16 | 1.84E-15 | 1.21E-14 | 0.01536419 | 2.78530148 |
| R..H | 54 | 2660 | 3.80636836 | 3.40E-16 | 3.91E-15 | 2.89E-14 | 0.02030075 | 3.69877206 |
| H...R | 46 | 2001 | 4.32736404 | 4.29E-16 | 7.29E-15 | 3.48E-14 | 0.02298851 | 4.2 |
| R....K | 39 | 1480 | 4.94388353 | 6.07E-16 | 1.40E-14 | 5.40E-14 | 0.02635135 | 4.83102012 |
| H.....G | 64 | 3962 | 3.01276588 | 2.13E-15 | 6.03E-14 | 1.77E-13 | 0.01615346 | 2.93073371 |
| K..K | 43 | 1839 | 4.40148691 | 2.16E-15 | 3.05E-14 | 1.72E-13 | 0.02338227 | 4.2736637 |
| H...R | 38 | 1485 | 4.80089804 | 3.55E-15 | 6.53E-14 | 3.12E-13 | 0.02558923 | 4.68782958 |
| H..R | 50 | 2513 | 3.73057871 | 8.88E-15 | 9.08E-14 | 7.46E-13 | 0.01989654 | 3.62362972 |
| HKR | 18 | 264 | 7.33710384 | 1.27E-14 | 9.47E-12 | 9.47E-12 | 0.06818182 | 13.0609756 |
| R...G | 74 | 5064 | 2.7507474 | 1.91E-14 | 2.32E-13 | 1.51E-12 | 0.01461295 | 2.64709419 |
| H.....K | 28 | 878 | 5.94789602 | 4.62E-14 | 9.82E-13 | 3.79E-12 | 0.03189066 | 5.88 |
| G | 723 | 111145 | 1.20185066 | 6.07E-14 | 6.07E-14 | 6.07E-14 | 0.00650502 | 1.16874808 |
| R.....K | 28 | 910 | 5.73873924 | 1.09E-13 | 1.86E-12 | 8.85E-12 | 0.03076923 | 5.66666667 |
| KRG | 22 | 504 | 4.69729864 | 1.44E-13 | 4.30E-11 | 1.08E-10 | 0.04365079 | 8.1473029 |
| RHK | 15 | 186 | 8.67829368 | 1.73E-13 | 4.30E-11 | 1.29E-10 | 0.08064516 | 15.6578947 |
| K....R | 36 | 1536 | 4.3972041 | 2.38E-13 | 3.66E-12 | 2.07E-11 | 0.0234375 | 4.284 |
| RRH | 17 | 278 | 6.58051909 | 3.98E-13 | 7.43E-11 | 2.96E-10 | 0.06115108 | 11.6264368 |
| K.H | 53 | 3076 | 3.17433429 | 4.85E-13 | 4.57E-12 | 4.13E-11 | 0.01723017 | 3.12950711 |
| K.....K | 27 | 909 | 5.53987204 | 6.72E-13 | 9.52E-12 | 5.38E-11 | 0.02970297 | 5.46428571 |
| KHK | 14 | 168 | 8.96757013 | 7.00E-13 | 1.03E-10 | 5.20E-10 | 0.08333333 | 16.2272727 |
| RHR | 14 | 170 | 8.86206931 | 8.23E-13 | 1.03E-10 | 6.11E-10 | 0.08235294 | 16.0192308 |
| K..H | 48 | 2694 | 3.34073739 | 1.47E-12 | 1.35E-11 | 1.22E-10 | 0.01781737 | 3.23809524 |
| R.....R | 28 | 1035 | 5.04565479 | 2.29E-12 | 2.78E-11 | 1.81E-10 | 0.02705314 | 4.9632572 |
| H...K | 38 | 1855 | 3.85613626 | 4.41E-12 | 4.69E-11 | 3.44E-10 | 0.02048518 | 3.7330765 |
| KA | 45 | 2500 | 3.30345141 | 7.87E-12 | 6.51E-11 | 6.38E-10 | 0.018 | 3.27189409 |
| R...R | 34 | 1610 | 3.96203566 | 1.76E-11 | 2.31E-10 | 1.51E-09 | 0.02111801 | 3.85088832 |
| RRG | 13 | 175 | 7.99394823 | 1.98E-11 | 2.11E-09 | 1.46E-08 | 0.07428571 | 14.3240741 |
| RY | 46 | 2725 | 3.09803802 | 3.76E-11 | 2.85E-10 | 3.01E-09 | 0.01688073 | 3.06494961 |
| K....S | 43 | 2579 | 3.12811314 | 7.22E-11 | 8.30E-10 | 6.13E-09 | 0.01667313 | 3.02661672 |
| K...W | 34 | 1684 | 3.80057685 | 8.37E-11 | 7.90E-10 | 6.44E-09 | 0.02019002 | 3.67818182 |
| H....K | 31 | 1447 | 4.01937477 | 9.51E-11 | 9.72E-10 | 7.98E-09 | 0.02142364 | 3.90783898 |
| K.S | 63 | 4726 | 2.4558959 | 1.52E-10 | 1.29E-09 | 1.27E-08 | 0.01333051 | 2.41164486 |
| R..Y | 36 | 1963 | 3.43859393 | 4.06E-10 | 3.39E-09 | 3.33E-08 | 0.01833928 | 3.33471718 |
| KS | 59 | 4482 | 2.41588122 | 1.08E-09 | 7.55E-09 | 8.52E-08 | 0.01316377 | 2.38107619 |
| HRG | 11 | 159 | 7.4447752 | 1.47E-09 | 1.37E-07 | 1.09E-06 | 0.06918239 | 13.2668919 |
| RW | 41 | 2540 | 2.96241268 | 1.50E-09 | 9.74E-09 | 1.17E-07 | 0.01614173 | 2.92857143 |
| R.S | 61 | 4818 | 2.33252421 | 2.01E-09 | 1.58E-08 | 1.67E-07 | 0.01266086 | 2.28894261 |

FIG. 13C

| motif | n | n.lib | enrich | p | fdr | padj.holm | Pr_seqs.motif | PLR |
|---|---|---|---|---|---|---|---|---|
| K..N | 37 | 2204 | 3.14766732 | 2.43E-09 | 1.86E-08 | 1.97E-07 | 0.01678766 | 3.04776188 |
| RKK | 9 | 94 | 10.3031657 | 2.59E-09 | 2.15E-07 | 1.91E-06 | 0.09574468 | 18.9 |
| K..F | 42 | 2764 | 2.86038137 | 2.76E-09 | 2.35E-08 | 2.10E-07 | 0.01519537 | 2.75422483 |
| YK | 53 | 3988 | 2.43902436 | 5.75E-09 | 3.49E-08 | 4.43E-07 | 0.01328987 | 2.40419314 |
| H....G | 61 | 5083 | 2.25903216 | 7.24E-09 | 5.60E-08 | 5.43E-07 | 0.01200079 | 2.1681601 |
| K.W | 40 | 2598 | 2.8365077 | 7.34E-09 | 5.31E-08 | 6.02E-07 | 0.01539646 | 2.79124316 |
| R...H | 35 | 2155 | 3.05726763 | 1.13E-08 | 8.04E-08 | 8.40E-07 | 0.0162413 | 2.94693396 |
| KGG | 9 | 114 | 8.49559276 | 1.43E-08 | 1.07E-06 | 1.06E-05 | 0.07894737 | 15.3 |
| R....H | 29 | 1618 | 3.36267442 | 1.87E-08 | 1.73E-07 | 1.55E-06 | 0.01793336 | 3.25770925 |
| AK | 54 | 4281 | 2.31498244 | 2.31E-08 | 1.32E-07 | 1.76E-06 | 0.01261388 | 2.28034067 |
| RYH | 10 | 164 | 6.56163668 | 2.72E-08 | 1.85E-06 | 2.00E-05 | 0.06097561 | 11.5909091 |
| G...K | 32 | 1931 | 3.11946698 | 3.01E-08 | 1.97E-07 | 2.19E-06 | 0.01657172 | 3.00789889 |
| K..S | 48 | 3660 | 2.45900178 | 3.06E-08 | 2.17E-07 | 2.45E-06 | 0.01311475 | 2.37209302 |
| KV | 63 | 5427 | 2.13047354 | 3.60E-08 | 1.93E-07 | 2.70E-06 | 0.01160862 | 2.09647651 |
| KF | 57 | 4754 | 2.20044793 | 6.94E-08 | 3.51E-07 | 5.13E-06 | 0.0119899 | 2.1661699 |
| KAA | 8 | 92 | 8.69582558 | 7.59E-08 | 4.49E-06 | 5.59E-05 | 0.08080808 | 15.6923077 |
| L....K | 26 | 1431 | 3.40878063 | 7.68E-08 | 6.42E-07 | 6.30E-06 | 0.01816911 | 3.30320285 |
| RHF | 18 | 696 | 2.78303901 | 7.82E-08 | 4.49E-06 | 5.75E-05 | 0.02586207 | 4.73893805 |
| KRH | 17 | 627 | 2.91767832 | 9.16E-08 | 4.89E-06 | 6.72E-05 | 0.02711324 | 4.97459016 |
| K.....R | 21 | 1005 | 3.89720351 | 9.81E-08 | 1.04E-06 | 7.65E-06 | 0.02089552 | 3.80945122 |
| WK | 56 | 4685 | 2.1936829 | 9.88E-08 | 4.73E-07 | 7.21E-06 | 0.01195304 | 2.15942968 |
| K.F | 52 | 4274 | 2.24146493 | 1.27E-07 | 8.51E-07 | 1.03E-05 | 0.01216659 | 2.19848413 |
| KQ | 35 | 2401 | 2.67529268 | 2.48E-07 | 1.13E-06 | 1.78E-05 | 0.01457726 | 2.64053254 |
| KHR | 9 | 159 | 6.09117971 | 2.53E-07 | 1.26E-05 | 0.00018535 | 0.05660377 | 10.71 |
| K.Y | 37 | 2649 | 2.57325537 | 2.79E-07 | 1.75E-06 | 2.23E-05 | 0.01396753 | 2.52852221 |
| HRK | 7 | 80 | 9.41594864 | 2.88E-07 | 1.34E-05 | 0.00021086 | 0.0875 | 17.1164384 |
| GK | 41 | 3075 | 2.44700104 | 3.10E-07 | 1.34E-06 | 2.20E-05 | 0.01333333 | 2.41216216 |
| R.F | 51 | 4316 | 2.17696708 | 3.22E-07 | 1.89E-06 | 2.54E-05 | 0.0118165 | 2.13446659 |
| HKN | 7 | 82 | 9.18629136 | 3.42E-07 | 1.50E-05 | 0.00024965 | 0.08536585 | 16.66 |
| H.....R | 20 | 994 | 3.75269669 | 3.53E-07 | 3.33E-06 | 2.71E-05 | 0.02012072 | 3.66529774 |
| K.L | 47 | 3853 | 2.24730475 | 3.82E-07 | 2.11E-06 | 2.98E-05 | 0.01219829 | 2.20428271 |
| G..K | 34 | 2370 | 2.68985743 | 3.94E-07 | 2.59E-06 | 3.12E-05 | 0.01434599 | 2.59803082 |
| NK | 58 | 5166 | 2.06048287 | 4.30E-07 | 1.78E-06 | 3.01E-05 | 0.01122726 | 2.02682067 |
| GR | 39 | 2888 | 2.47835112 | 5.22E-07 | 2.07E-06 | 3.60E-05 | 0.01350416 | 2.44348894 |
| KRR | 9 | 174 | 5.56607801 | 5.40E-07 | 2.24E-05 | 0.00039453 | 0.05172414 | 9.73636364 |
| RKA | 7 | 82 | 8.18778143 | 7.51E-07 | 2.95E-05 | 0.00054749 | 0.07608696 | 14.7 |
| H....G | 50 | 4443 | 2.11134416 | 7.88E-07 | 6.04E-06 | 6.38E-05 | 0.01125366 | 2.03164125 |

FIG. 13D

| motif | n | n.lib | enrich | p | fdr | padj.holm | Pr_seqs.motif | PLR |
|---|---|---|---|---|---|---|---|---|
| HKK | 7 | 97 | 7.76573084 | 1.08E-06 | 4.02E-05 | 0.00078319 | 0.07216495 | 13.8833333 |
| F..K | 29 | 1950 | 2.79947166 | 1.13E-06 | 6.84E-06 | 6.11E-05 | 0.01487179 | 2.69469027 |
| K.V | 43 | 3538 | 2.23910133 | 1.32E-06 | 6.92E-06 | 0.000102 | 0.01215376 | 2.19613734 |
| HKF | 9 | 194 | 4.99225554 | 1.34E-06 | 4.75E-05 | 0.00097149 | 0.04639175 | 8.68378378 |
| R...N | 22 | 1259 | 3.27840264 | 1.40E-06 | 9.89E-06 | 0.0001118 | 0.01747419 | 3.17461601 |
| RHG | 15 | 605 | 2.66803739 | 1.54E-06 | 5.22E-05 | 0.00111556 | 0.02479339 | 4.53813559 |
| K...Q | 27 | 1793 | 2.83462859 | 2.07E-06 | 1.13E-05 | 0.00014691 | 0.01505856 | 2.7290487 |
| R..F | 40 | 3228 | 2.32340627 | 2.10E-06 | 1.22E-05 | 0.00016378 | 0.01239157 | 2.23964868 |
| Y..K | 33 | 2446 | 2.5296252 | 2.12E-06 | 1.22E-05 | 0.00016378 | 0.01349141 | 2.44115209 |
| K...Y | 25 | 1582 | 2.97472085 | 2.13E-06 | 1.13E-05 | 0.00014899 | 0.01580278 | 2.86608863 |
| GRG | 9 | 208 | 4.65623834 | 2.37E-06 | 7.70E-05 | 0.00171804 | 0.04326923 | 8.07286432 |
| KKH | 10 | 368 | 4.01532991 | 2.49E-06 | 7.75E-05 | 0.00180267 | 0.03731343 | 6.91860465 |
| QRKK | 3 | 6 | 8.36593216 | 3.00E-06 | 0.00034723 | 0.00079684 | 0.5 | 178.5 |
| RRGS | 3 | 6 | 8.36593216 | 3.00E-06 | 0.00034723 | 0.00079684 | 0.5 | 178.5 |
| K..A | 35 | 2677 | 2.40870046 | 3.02E-06 | 1.45E-05 | 0.00022955 | 0.01307434 | 2.36468584 |
| K.N | 35 | 2681 | 2.40510672 | 3.09E-06 | 1.45E-05 | 0.00023163 | 0.01305483 | 2.36111111 |
| RKV | 9 | 219 | 4.42236335 | 3.61E-06 | 0.00010777 | 0.0026077 | 0.04109589 | 7.65 |
| H...H | 29 | 2080 | 2.62450468 | 3.86E-06 | 1.93E-05 | 0.00026629 | 0.01394231 | 2.52389078 |
| H..N | 30 | 2175 | 2.58619153 | 3.95E-06 | 2.14E-05 | 0.00030035 | 0.0137931 | 2.4965035 |
| KKR | 10 | 283 | 3.80250324 | 4.03E-06 | 0.00011248 | 0.00290873 | 0.03533569 | 6.53846154 |
| A.K | 38 | 3043 | 2.30061934 | 4.06E-06 | 1.74E-05 | 0.00030017 | 0.01248768 | 2.25723794 |
| RKF | 8 | 167 | 5.15501038 | 4.07E-06 | 0.00011248 | 0.0029312 | 0.04790419 | 8.98113208 |
| K..P | 34 | 2593 | 2.41568066 | 4.08E-06 | 1.74E-05 | 0.00030017 | 0.01311223 | 2.37162954 |
| R.N | 33 | 2474 | 2.44799013 | 5.05E-06 | 1.91E-05 | 0.00034311 | 0.01333872 | 2.41315035 |
| Y.K | 38 | 3099 | 2.25904635 | 5.07E-06 | 2.07E-05 | 0.00036486 | 0.01226202 | 2.2159425 |
| S...R | 23 | 1473 | 2.92947927 | 5.11E-06 | 3.28E-05 | 0.0004038 | 0.01561439 | 2.83137931 |
| HKRR | 3 | 7 | 7.170799 | 5.22E-06 | 0.00034723 | 0.00137846 | 0.42857143 | 133.875 |
| HRLN | 3 | 7 | 7.170799 | 5.22E-06 | 0.00034723 | 0.00137846 | 0.42857143 | 133.875 |
| K...L | 28 | 2033 | 2.58396123 | 5.35E-06 | 3.28E-05 | 0.00041698 | 0.01377275 | 2.49276808 |
| K..V | 30 | 2249 | 2.51098714 | 6.18E-06 | 2.92E-05 | 0.00042033 | 0.01333926 | 2.41324921 |
| KHG | 13 | 515 | 2.71639018 | 6.18E-06 | 0.00016492 | 0.00445095 | 0.02524272 | 4.62250996 |
| K...H | 29 | 2141 | 2.54972897 | 6.61E-06 | 2.96E-05 | 0.00044266 | 0.01354507 | 2.45099432 |
| RRL | 9 | 238 | 4.06931754 | 7.05E-06 | 0.0001818 | 0.00507456 | 0.03781513 | 7.01528384 |
| R...S | 37 | 3095 | 2.25036912 | 7.71E-06 | 3.21E-05 | 0.00050873 | 0.01195477 | 2.15974493 |
| S...K | 27 | 1933 | 2.62932699 | 7.92E-06 | 3.21E-05 | 0.00051502 | 0.01396793 | 2.52859391 |
| KRW | 8 | 185 | 4.6534418 | 8.61E-06 | 0.00021442 | 0.0061828 | 0.04324324 | 8.06779661 |
| R..S | 41 | 3596 | 2.13777929 | 8.90E-06 | 4.55E-05 | 0.00066731 | 0.01140156 | 2.05864979 |

FIG. 13E

| motif | n | n.lib | enrich | p | fdr | padj.holm | Pr_seqs.motif | PLR |
|---|---|---|---|---|---|---|---|---|
| R...N | 25 | 1726 | 2.7265402 | 9.30E-06 | 3.59E-05 | 0.00059491 | 0.01448436 | 2.62345679 |
| R....L | 27 | 2003 | 2.52899607 | 1.13E-05 | 6.53E-05 | 0.00087383 | 0.01347978 | 2.43901822 |
| KKW | 6 | 92 | 7.01809836 | 1.14E-05 | 0.00026726 | 0.00820872 | 0.06521739 | 12.4534884 |
| VHR | 6 | 93 | 7.01809836 | 1.14E-05 | 0.00026726 | 0.00820872 | 0.06521739 | 12.4534884 |
| KVHR | 3 | 9 | 5.57728811 | 1.24E-05 | 0.00066135 | 0.00325705 | 0.33333333 | 89.25 |
| K....S | 28 | 2183 | 2.3922367 | 1.25E-05 | 0.00010588 | 0.00094671 | 0.01282639 | 2.31925754 |
| QK | 56 | 5559 | 1.84873654 | 1.38E-05 | 4.66E-05 | 0.00085698 | 0.01007375 | 1.81646375 |
| RRK | 6 | 97 | 6.65634072 | 1.55E-05 | 0.00035103 | 0.01108761 | 0.06185567 | 11.7692308 |
| K..F | 38 | 3306 | 2.15515961 | 1.79E-05 | 8.68E-05 | 0.00132605 | 0.01149425 | 2.0755814 |
| RRF | 8 | 206 | 4.17906181 | 1.87E-05 | 0.00041053 | 0.01336937 | 0.03883495 | 7.21212121 |
| AKA | 7 | 150 | 5.02183927 | 1.92E-05 | 0.00041053 | 0.01371472 | 0.04666667 | 8.73776224 |
| R....F | 24 | 1758 | 2.5461983 | 1.93E-05 | 0.00014948 | 0.00145085 | 0.01365188 | 2.47058824 |
| RKS | 7 | 155 | 4.85984446 | 2.38E-05 | 0.00049285 | 0.01691121 | 0.04516129 | 8.44256757 |
| Y...K | 26 | 1945 | 2.51632325 | 2.40E-05 | 8.88E-05 | 0.00151425 | 0.01336761 | 2.41844711 |
| KKWR | 3 | 11 | 4.56323572 | 2.42E-05 | 0.00080546 | 0.00632254 | 0.27272727 | 66.9375 |
| RHRG | 3 | 11 | 4.56323572 | 2.42E-05 | 0.00080546 | 0.00632254 | 0.27272727 | 66.9375 |
| RRHY | 3 | 11 | 4.56323572 | 2.42E-05 | 0.00080546 | 0.00632254 | 0.27272727 | 66.9375 |
| HRH | 9 | 279 | 3.47131747 | 2.48E-05 | 0.00050101 | 0.0176439 | 0.03225806 | 5.95 |
| R...V | 29 | 2283 | 2.39113874 | 2.68E-05 | 9.49E-05 | 0.00166196 | 0.01370258 | 2.29658385 |
| KRWHF | 2 | 2 | 1.567276 | 2.79E-05 | 3.72E-05 | 0.00011173 | 1 | Inf |
| LWKHG | 2 | 2 | 1.567276 | 2.79E-05 | 3.72E-05 | 0.00011173 | 1 | Inf |
| WKHRG | 2 | 2 | 1.567276 | 2.79E-05 | 3.72E-05 | 0.00011173 | 1 | Inf |
| KRK | 7 | 160 | 4.70797432 | 2.91E-05 | 0.00055752 | 0.02066625 | 0.04375 | 8.16666667 |
| YYK | 7 | 160 | 4.70797432 | 2.91E-05 | 0.00055752 | 0.02066625 | 0.04375 | 8.16666667 |
| K....H | 23 | 1666 | 2.59010982 | 3.44E-05 | 0.0001836 | 0.00261139 | 0.01380552 | 2.49878271 |
| Y.R | 37 | 3279 | 2.07885132 | 3.48E-05 | 0.00013629 | 0.00247053 | 0.01128393 | 2.03716841 |
| G....K | 20 | 1334 | 2.81280422 | 3.59E-05 | 0.0001836 | 0.00269413 | 0.0149925 | 2.71689498 |
| SR | 33 | 2763 | 2.19193904 | 3.61E-05 | 0.00012186 | 0.00238184 | 0.01194354 | 2.15769231 |
| KY | 32 | 2610 | 2.2501159 | 3.62E-05 | 0.00012186 | 0.00238184 | 0.01226054 | 2.21567106 |
| RWK | 8 | 227 | 3.79245257 | 3.73E-05 | 0.00068678 | 0.02644117 | 0.03524229 | 6.52054795 |
| KVS | 13 | 613 | 2.28212225 | 3.77E-05 | 0.00068678 | 0.0266501 | 0.02120718 | 3.8675 |
| KN | 30 | 2422 | 2.27322557 | 3.84E-05 | 0.00012467 | 0.00245496 | 0.01238646 | 2.23871237 |
| F..K | 29 | 2332 | 2.33167568 | 4.05E-05 | 0.00017814 | 0.00295286 | 0.01343568 | 2.24772036 |
| HG | 52 | 5251 | 1.81742603 | 4.06E-05 | 0.00012734 | 0.00255654 | 0.00990288 | 1.78534334 |
| K..V | 33 | 2821 | 2.19335811 | 4.07E-05 | 0.00017814 | 0.00295286 | 0.01169798 | 2.11380488 |
| R....A | 18 | 1132 | 2.98326215 | 4.14E-05 | 0.00020027 | 0.00306066 | 0.01590106 | 2.88420108 |
| AKAK | 3 | 13 | 3.86119946 | 4.17E-05 | 0.00123111 | 0.01074679 | 0.23076923 | 53.55 |

FIG. 13F

| motif | n | n.lib | enrich | p | fdr | padj.holm | Pr_seqs.motif | PLR |
|---|---|---|---|---|---|---|---|---|
| RNK | 8 | 231 | 3.72678239 | 4.22E-05 | 0.00075122 | 0.02981958 | 0.03463203 | 6.40358744 |
| KL | 50 | 5031 | 1.82394234 | 6.00E-05 | 0.00018191 | 0.00371816 | 0.00993838 | 1.79180887 |
| R.....H | 18 | 1200 | 2.79763538 | 6.45E-05 | 0.00045723 | 0.00477667 | 0.015 | 2.71827411 |
| RHKL | 3 | 15 | 3.34637286 | 6.57E-05 | 0.00150751 | 0.01689528 | 0.2 | 44.625 |
| HKS | 7 | 182 | 4.13887852 | 6.58E-05 | 0.0011434 | 0.04640172 | 0.03846154 | 7.14 |
| RQR | 8 | 247 | 3.48537139 | 6.75E-05 | 0.00114551 | 0.04750127 | 0.03238866 | 5.9748954 |
| R...P | 22 | 1607 | 2.57703011 | 7.03E-05 | 0.00023789 | 0.00426797 | 0.01369011 | 2.47760252 |
| NKK | 7 | 184 | 4.09389071 | 7.05E-05 | 0.00117005 | 0.04955097 | 0.03804348 | 7.05932203 |
| R..L | 34 | 3036 | 2.09978989 | 7.74E-05 | 0.00032378 | 0.00549729 | 0.01119895 | 2.02165223 |
| W...K | 24 | 1853 | 2.43808314 | 7.81E-05 | 0.00025522 | 0.00468403 | 0.01295197 | 2.34226353 |
| NKYK | 3 | 18 | 3.13722456 | 8.06E-05 | 0.00150751 | 0.02063067 | 0.1875 | 41.1923077 |
| K.....N | 14 | 798 | 3.27208816 | 8.30E-05 | 0.00054278 | 0.00605972 | 0.01754386 | 3.1875 |
| R...Y | 22 | 1627 | 2.5453518 | 8.33E-05 | 0.00026237 | 0.0049172 | 0.01352182 | 2.44672897 |
| KFSG | 5 | 82 | 1.02023563 | 8.35E-05 | 0.00150751 | 0.02128916 | 0.06097561 | 11.5909091 |
| RWHFD | 2 | 3 | 1.04485066 | 8.35E-05 | 8.35E-05 | 0.00011173 | 0.66666667 | 357 |
| FHHK | 2 | 3 | 11.1545762 | 8.50E-05 | 0.00150751 | 0.02159252 | 0.66666667 | 357 |
| KKPH | 2 | 3 | 11.1545762 | 8.50E-05 | 0.00150751 | 0.02159252 | 0.66666667 | 357 |
| LHHN | 2 | 3 | 11.1545762 | 8.50E-05 | 0.00150751 | 0.02159252 | 0.66666667 | 357 |
| R....D | 37 | 3539 | 1.96149182 | 8.54E-05 | 0.00039299 | 0.00623652 | 0.01045493 | 1.88592233 |
| SK | 31 | 2652 | 2.14527806 | 8.63E-05 | 0.00024739 | 0.00526705 | 0.01168929 | 2.11121709 |
| HY | 33 | 2865 | 2.13390142 | 8.70E-05 | 0.00024739 | 0.00526705 | 0.01151832 | 2.07997881 |
| K..P | 25 | 1958 | 2.39401029 | 0.00011801 | 0.00042928 | 0.00770084 | 0.01276813 | 2.30858769 |
| K..Y | 25 | 1962 | 2.38912953 | 0.00011199 | 0.00042928 | 0.00772709 | 0.0127421 | 2.30382034 |
| G.....R | 16 | 1034 | 2.88601973 | 0.0001136 | 0.00068971 | 0.00817917 | 0.01547389 | 2.80550098 |
| KRBH | 3 | 18 | 2.78864405 | 0.00011649 | 0.00167972 | 0.02924016 | 0.16666667 | 35.7 |
| NKKH | 3 | 18 | 2.78864405 | 0.00011649 | 0.00167972 | 0.02924016 | 0.16666667 | 35.7 |
| SPNL | 3 | 18 | 2.78864405 | 0.00011649 | 0.00167972 | 0.02924016 | 0.16666667 | 35.7 |
| HREG | 4 | 47 | 1.42398845 | 0.00011998 | 0.00167972 | 0.02975509 | 0.08510638 | 16.6046512 |
| LK | 32 | 2804 | 2.10249558 | 0.00012088 | 0.00045451 | 0.00846153 | 0.01141227 | 2.06060606 |
| K...P | 21 | 1567 | 2.52268478 | 0.00013467 | 0.00040882 | 0.0078109 | 0.0134014 | 2.42464424 |
| K..L | 33 | 3014 | 2.05290751 | 0.00013706 | 0.0005044 | 0.00932035 | 0.01094891 | 1.97601476 |
| S..K | 28 | 2351 | 2.23307903 | 0.00014897 | 0.00052712 | 0.00998092 | 0.01190983 | 2.1515282 |
| Q.K | 31 | 2711 | 2.10666412 | 0.00016098 | 0.00056606 | 0.01118793 | 0.01143489 | 2.06473881 |
| RHKR | 3 | 20 | 2.50977965 | 0.00016146 | 0.00173325 | 0.03987954 | 0.15 | 31.5 |
| RWKG | 3 | 20 | 2.50977965 | 0.00016146 | 0.00173325 | 0.03987954 | 0.15 | 31.5 |
| H.N | 31 | 2715 | 2.10356038 | 0.00016259 | 0.00056606 | 0.01118793 | 0.01141805 | 2.0616617 |
| K.....H | 17 | 1180 | 2.68699443 | 0.00016309 | 0.0009242 | 0.0115797 | 0.01440678 | 2.60920034 |

FIG. 13G

| motif | n | n.lib | enrich | p | fdr | padj.holm | Pr_seqs.motif | PLR |
|---|---|---|---|---|---|---|---|---|
| L...K | 24 | 1914 | 2.36038038 | 0.000166 | 0.00048656 | 0.00946217 | 0.01253918 | 2.26666667 |
| H...G | 49 | 5204 | 1.76545838 | 0.00016666 | 0.00056789 | 0.01099977 | 0.00941583 | 1.69670223 |
| HFRN | 2 | 4 | 8.36593216 | 0.00016942 | 0.00173325 | 0.04150678 | 0.5 | 178.5 |
| KAAY | 2 | 4 | 8.36593216 | 0.00016942 | 0.00173325 | 0.04150678 | 0.5 | 178.5 |
| KGGQ | 2 | 4 | 8.36593216 | 0.00016942 | 0.00173325 | 0.04150678 | 0.5 | 178.5 |
| KHYP | 2 | 4 | 8.36593216 | 0.00016942 | 0.00173325 | 0.04150678 | 0.5 | 178.5 |
| KPHP | 2 | 4 | 8.36593216 | 0.00016942 | 0.00173325 | 0.04150678 | 0.5 | 178.5 |
| P.K | 34 | 3122 | 2.00636129 | 0.00017185 | 0.00057692 | 0.01151389 | 0.01089045 | 1.96534974 |
| A..K | 28 | 2397 | 2.19022478 | 0.00017644 | 0.00057973 | 0.01146851 | 0.01168127 | 2.10975095 |
| HKRG | 3 | 21 | 2.39026633 | 0.00018761 | 0.00178234 | 0.04502753 | 0.14285714 | 29.75 |
| RWHF | 3 | 21 | 2.39026633 | 0.00018761 | 0.00178234 | 0.04502753 | 0.14285714 | 29.75 |
| S.R | 32 | 2918 | 2.02035558 | 0.00019043 | 0.00061724 | 0.01256812 | 0.01096642 | 1.97920998 |
| RS | 48 | 5032 | 1.75063667 | 0.00020761 | 0.00057251 | 0.01224919 | 0.00953895 | 1.71910112 |
| S..R | 28 | 2436 | 2.15515961 | 0.00021043 | 0.00066759 | 0.01346781 | 0.01149425 | 2.0755814 |
| R.Y | 30 | 2632 | 2.09989941 | 0.00022308 | 0.00069899 | 0.01450029 | 0.01139818 | 2.05803228 |
| K...S | 33 | 3089 | 2.01098449 | 0.00022919 | 0.00064938 | 0.01283485 | 0.01068307 | 1.92751963 |
| K..Q | 27 | 2322 | 2.1802196 | 0.00024867 | 0.00076259 | 0.01566625 | 0.01162791 | 2.1 |
| A..R | 29 | 2575 | 2.11163794 | 0.0003112 | 0.00092355 | 0.01929421 | 0.01126214 | 2.03318932 |
| H....S | 29 | 2649 | 2.05390996 | 0.00031487 | 0.00137942 | 0.0236704 | 0.01094753 | 1.97576336 |
| RF | 50 | 5413 | 1.69522518 | 0.00034688 | 0.00092841 | 0.02011885 | 0.00923702 | 1.6641805 |
| H...Q | 22 | 1773 | 2.33575149 | 0.00035564 | 0.00097354 | 0.01955993 | 0.01240835 | 2.24371845 |
| K.....V | 18 | 1384 | 2.42569542 | 0.00035911 | 0.00190775 | 0.0251374 | 0.01300578 | 2.35212299 |
| H...S | 32 | 3062 | 1.96724061 | 0.00036651 | 0.00097354 | 0.01979141 | 0.01045069 | 1.88514851 |
| K....N | 17 | 1244 | 2.56385748 | 0.00038496 | 0.00160982 | 0.02733191 | 0.01366559 | 2.47310513 |
| R.N | 29 | 2636 | 2.02682249 | 0.00039706 | 0.00120398 | 0.0254116 | 0.01100152 | 1.98561565 |
| S.K | 31 | 2871 | 1.98926033 | 0.00042443 | 0.00124677 | 0.02673933 | 0.01079763 | 1.94841549 |
| R...W | 21 | 1655 | 2.38854807 | 0.00043382 | 0.00111741 | 0.02299237 | 0.01268882 | 2.29406365 |
| R.W | 29 | 2681 | 1.99280271 | 0.00047751 | 0.00136017 | 0.02960535 | 0.01081686 | 1.95192308 |
| Y....K | 18 | 1399 | 2.41390475 | 0.00052926 | 0.00211352 | 0.03704793 | 0.01286633 | 2.32657495 |
| Y..R | 28 | 2577 | 2.03724051 | 0.00054628 | 0.00157055 | 0.03332306 | 0.01086535 | 1.96076893 |
| Y....R | 19 | 1525 | 2.33748642 | 0.00055135 | 0.00211352 | 0.03804342 | 0.01245902 | 2.25199203 |
| R.....S | 24 | 2150 | 2.08196121 | 0.00058965 | 0.00294823 | 0.0406856 | 0.01116279 | 2.01505174 |
| N.R | 32 | 3078 | 1.91533385 | 0.0006851 | 0.0018941 | 0.04179103 | 0.01039636 | 1.87524623 |
| A...K | 22 | 1896 | 2.1842233 | 0.00069761 | 0.00174403 | 0.03627576 | 0.01160338 | 2.09551761 |
| F.K | 30 | 2875 | 1.92241226 | 0.00073275 | 0.00198795 | 0.04396477 | 0.01043478 | 1.88224956 |

METHODS FOR DIAGNOSIS AND TREATMENT OF AUTOIMMUNE DISEASES

CROSS-REFERENCE

This patent application is a U.S. National Phase of International Application No. PCT/US17/38392, which claims the benefit of U.S. Application Ser. No. 62/352,519, filed Jun. 20, 2016; and U.S. Application Ser. No. 62/421,185, filed Nov. 11, 2016; each of which is incorporated herein by reference in their entirety.

SEQUENCE LISTING

The instant application contains a Sequence Listing which has been submitted electronically in ASCII format and is hereby incorporated by reference in its entirety. Said ASCII copy, created on May 11, 2021, is named 59582-704_831_SL.txt and is 10,940 bytes in size.

BACKGROUND OF THE INVENTION

Autoimmune disease patients can experience chronically active disease, fluctuating rounds of remission and flare, or long quiescence. Accurately detecting and determining the status of a patient is central to prescribing appropriate drug regimens, evaluating treatment outcomes, defining patient subgroups, and early detection of flare onsets in order to improve therapeutic outcomes of patients afflicted with an autoimmune disease.

SUMMARY OF THE INVENTION

Provided herein are methods, assays and devices for determining or diagnosing immune-mediated disease activity in a subject. Immune mediated disease activity includes but is not limited to autoimmune disease activity, infectious disease activity, cancer activity and diabetes disease activity.

Accordingly, disclosed herein are methods, assays and devices for determining autoimmune disease activity in a subject, said method comprising: contacting a sample from the subject to a peptide array comprising a plurality of different peptides on distinct features of the array; detecting the binding of antibodies present in the sample to a set of peptides on the peptide array to obtain a pattern of binding signals, wherein the set of peptides are indicative of autoimmune disease activity; and comparing said binding signal to reference binding signals obtained from a plurality of subjects in a reference group having a range of disease activities to determine the presence and/or severity of autoimmune disease activity in said subject.

In some embodiments, the peptide array comprises at least 10,000 different peptides, at least 50,000 different peptides or at least 100,000 different peptides. In other embodiments, the different peptides on the array are deposited. In still other embodiments, the different peptides on the array are synthesized in situ. In yet other embodiments, the synthesis of peptides in situ comprises less than 20 different amino acids. In some embodiments, cysteine, methionine, isoleucine and threonine are excluded during synthesis of the peptide array.

In one embodiment, the autoimmune disease comprises systemic lupus erythematosus (SLE), rheumatoid arthritis, Sjogren's disease, multiple sclerosis, ulcerative colitis, psoriatic arthritis, scleroderma and/or type I diabetes. In other embodiments, the autoimmune disease is systemic lupus erythematosus (SLE). In other embodiments, the binding signal of a set of peptides indicative of SLE in the reference samples are higher in subjects from the reference group having a score of at least 12 when using SLEDAI or SLEDAI-SELENA scoring system. In still other embodiments, the binding signal of a set of peptides indicative of SLE in the reference samples are lower in subjects from the reference having a score of less than 2 when using SLEDAI or SLEDAI-SELENA scoring system. In one embodiment, the binding signal of a set of peptides indicative of SLE in the reference samples are lower in subjects from the reference group having a score of at least 12 when using SLEDAI or SLEDAI-SELENA scoring system. In another embodiment, the binding signal of a set of peptides indicative of SLE in the reference samples are lower in subjects from the reference group having a score of less than 2 when using SLEDAI or SLEDAI-SELENA scoring system. In another embodiment, the set of peptides indicative of SLE in the reference samples are enriched by greater than 100% in one or more sequence motifs or amino acids listed in FIGS. 13A-13G. In still other embodiments, the average binding signal of the set of peptides indicative of an autoimmune disorder in the reference samples is lower in subjects from said reference group having high disease activity than the average binding signal of said peptides from subjects in said reference group having higher disease activity.

In still other embodiments, the set of peptides indicative of SLE are enriched by at least 150% in at least one or more amino acids as compared to the remaining peptides in the peptide array. In yet other embodiments, the set of peptides comprises at least 10 peptides, at least 20 peptides, at least 30 peptides, at least 40 peptides, at least 50 peptides, at least 60 peptides, at least 70 peptides, at least 80 peptides, at least 90 peptides or at least 100 peptides are indicative of autoimmune disease activity. In one embodiment, the pattern of binding signals obtained classifies said autoimmune disease activity selected from low disease activity, moderate disease activity, and severe disease activity. In another embodiment, a calculated area under the receiver operator characteristic (ROC) curve (AUC) ranging from 0.60 to 0.70, 0.70 to 0.79, 0.80 to 0.89, or 0.90 to 1.0 determines the presence and/or severity of autoimmune disease activity in said subject.

In yet other embodiments, a range of disease activities is determined by the presence of one or more clinical conditions comprising high anti-dsDNA antibodies, low complement protein C3, low complement protein C4, high antinuclear antibody (ANA), high proteinuria, malar rash, CNS manifestation, arthritis, cytopenia, discoid rash, oral ulcers, renal manifestation, immunologic, photosensitivity, and serositis. In some embodiments, a range of disease activities is further determined by the presence of one or more clinical conditions comprising high anti-dsDNA antibodies, low complement protein C3, low complement protein C4, high antinuclear antibody (ANA), high proteinuria, malar rash, CNS manifestation, arthritis, cytopenia, discoid rash, oral ulcers, renal manifestation, immunologic, photosensitivity, and serositis. In still other embodiments, a range of disease activities is further determined by the presence of a known biomarker of one or more clinical conditions.

In one embodiment, the subject is human. In another embodiment, the sample is a blood sample. In other embodiments, the blood sample is selected from whole blood, plasma, or serum. In one embodiment, the sample is a serum sample. In still other embodiments, the sample is a plasma sample. In yet other embodiments, the sample is a dried blood sample. In still other embodiments, the at least 10,000 different peptides on the peptide array are at least 5 amino acids in length. In other embodiments, the at least 10,000 different peptides on the peptide array are at least between 5 and 15 amino acids in length. In another embodiment, the at least 10,000 different peptides are synthesized from less than 20 amino acids. In other embodiments, the at least 10,000 different peptides on the peptide array are synthesized by excluding one or more of cysteine, methionine, isoleucine and threonine.

Also disclosed herein are immunosignatures of a subject indicative of an autoimmune disorder obtained from a sample, wherein the immunosignature comprises a binding pattern from a set of peptides on a peptide array comprising at least 10,000 peptides. In some embodiments, the immunosignature comprises an enrichment of at least one amino acid in the set of peptides by at least 150%, as compared to remaining peptides on the peptide array. In other embodiments, the peptide array comprises at least 5,000 different peptides, at least 50,000 different peptides, at least 100,000 different peptides, at least 250,000 peptides, at least 330,000 peptides. In other embodiments, the at least 10,000 different peptides on the peptide array is between 5 and 15 amino acids in length.

Also disclosed herein are systems for determining autoimmune disease activity in a subject, the system comprising: (a) an array of peptides comprising at least 10,000 different peptides synthesized in situ, wherein a sample from a subject is contacted to the array; (b) a detector for detecting the binding of antibodies present in said sample to a set of peptides on said array to obtain a combination of binding signals; and (c) a digital processing device for analyzing and comparing said combination of binding signals to one or more groups of combinations of reference binding signals, wherein each of said groups of combinations of reference binding signals comprises a combination of binding signals obtained from a plurality of healthy subjects, thereby determining whether the subject has an autoimmune disease. In some embodiments, the autoimmune disease is SLE.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings in the following.

FIG. 1A shows a SLEDAI Score Sheet of clinical and laboratory manifestations used to assess systemic lupus erythematosus diagnosis and assessment.

FIG. 1B shows a continuation of a SLEDAI Score Sheet of clinical and laboratory manifestations used to assess systemic lupus erythematosus diagnosis and assessment.

FIG. 7 discloses SEQ ID NOS 1, 2, 12-14, 3-8, 15, 9-11, respectively, in order of appearance.

FIG. 13A-13G shows the peptide motifs and amino acids that are enriched in the peptides that correlate to a diagnosis from a SLEDAI score. FIG. 13D discloses SEQ ID NOS 16-19, respectively, in order of appearance. FIG. 13E discloses SEQ ID NOS 20-27, respectively, in order of appearance. FIG. 13F discloses SEQ ID NOS 28-40, respectively, in order of appearance. FIG. 13G discloses SEQ ID NOS 41-47, respectively, in order of appearance.

DETAILED DESCRIPTION OF THE INVENTION

Figure 2:
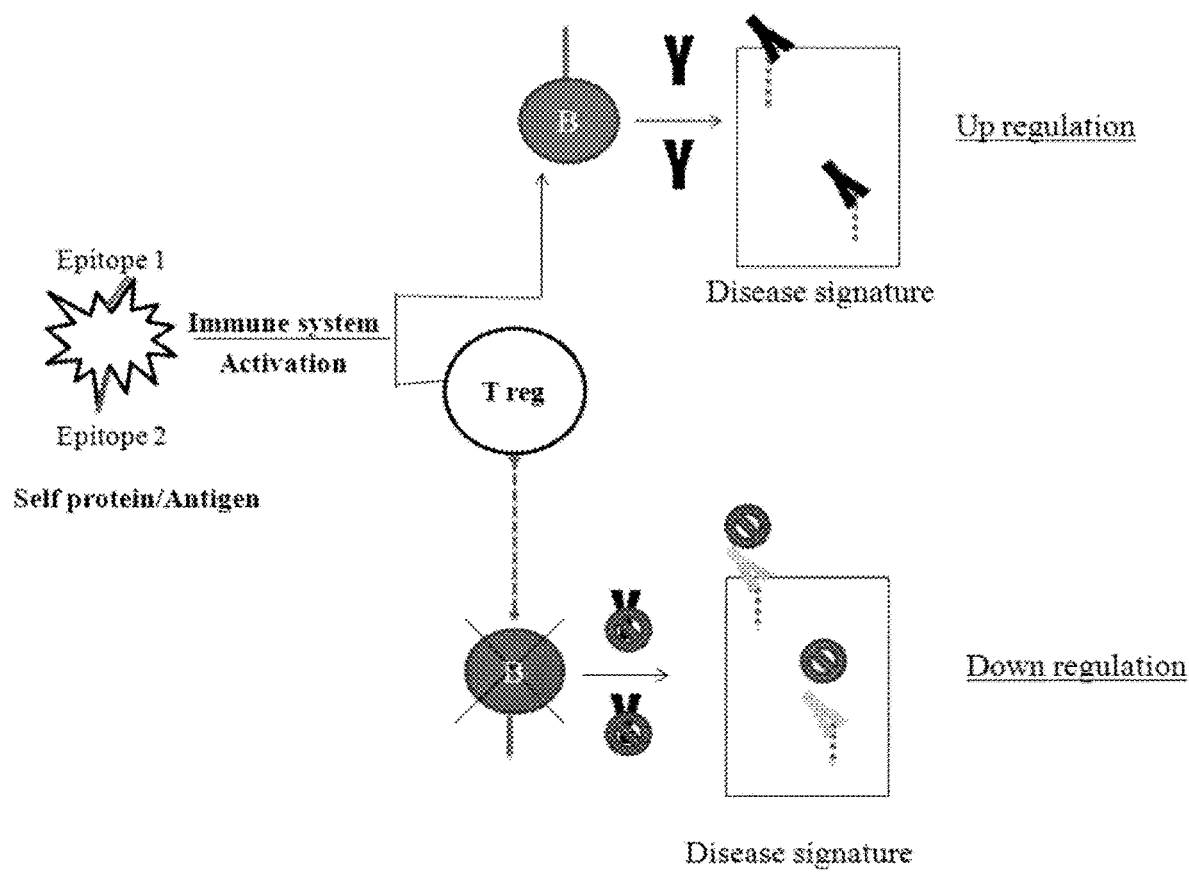
FIG. 2 shows a summary of the SLE patients in the study.

Detecting and diagnosing immune-mediated disorders, such as autoimmune disorders, is challenging, with patients having a difficult time receiving an accurate or correct diagnosis. Autoimmune diseases remains a major cause of morbidity and mortality. In many instances, patients are often misdiagnosed with other autoimmune conditions because of the closely related nature of these diseases. There are currently no reliable bio-markers available for the detection and assessment of autoimmune diseases or disorders. Prompt treatment, for example of flares related to systemic lupus erytrematosus, not results in better immediate outcomes, but will prevent cumulative chronic organ damage. Accordingly, sensitive and specific diagnosis of disease activity remains an important unmet clinical need. See Oglesby et al, Impact of early versus late systemic lupus erythematosus diagnosis on clinical and economic outcomes. Applied Health Economics & Health Policy. 12(2):

179-90, 2014; Lisnevskaia et al, Systemic lupus erythematosus. Lancet. 384(9957):1878-88, 2014.

A common approach instead for clinical studies is the use of scoring systems to evaluate physiological and biochemical manifestations of the autoimmune condition in subjects. For example, the most commonly used study of lupus activity for clinical subjects is the Systemic Lupus Erythematosus Disease Activity Index (SLEDAI). SLEDAI is a list of 24 clinical manifestations and laboratory tests, such as seizure, psychosis, organic brain syndrome, visual disturbance, other neurological problems, hair loss, new rash, muscle weakness, arthritis, blood vessel inflammation, mouth sores, chest pain worsening with deep breathing and manifestations of pleurisy and/or pericarditis and fever. The laboratory results analyzed include urinalysis testing, blood complement levels, increased anti-DNA antibody levels, low platelets and low white blood cell count. Each item is scored based on whether these manifestations have been present or absent in the patient in the previous 10 days. See FIG. TA and FIG. 1B.

The SLEDAI index requires weighting of the different clinical and laboratory test categories, including organ involvement. For example, joint pain and kidney disease are each multiplied by four, but central nervous system neurological manifestations are multiplied by eight. The assigned weighted assessment is then summed up into a final score, which ranges from zero to 105, with scores greater than 20 being unusual or rare. However, while there is no consensus on how to classify these scores, a SLEDAI score of 6 or more has been shown to be consistent with active disease requiring therapy, while a score below 3 is generally considered to be inactive. Scores of 4 to 15 are indicative of mild or moderate disease, and those greater than 15 are considered to be severe. A clinically meaningful difference has been reported to be an improvement of 6 points or worsening of 8 points.

The SLEDAI assessment was modified in the Safety of Estrogens in Lupus Erythematosus National Assessment (SELENA) trial, also known as the SELENA-SLEDAI flare index. While the SELENA-SLEDAI offers some clarification with regards to the definitions of clinical activity in each item, the basic premise and scoring system developed and characterized in the SLEDAI analysis has not changed significantly.

Yet other clinical assessment instruments for assessing systemic lupus erythematosus includes the BILAG (British Isles Lupus Activity Group), which is an 86 question physician's assessment of specific organ function, including a compilation of multiple manifestations and laboratory tests combined into a single score for a given organ system. In addition, other diseases or disorders have similar correlative assays which can also be used to establish or grade disease activity, including DAS28 (Disease Activity Score) for rheumatoid arthritis, TNM (Tumor, Node, Metastasis) staging system for cancer disorders, the Nottingham grading system (also known as the Elston-Ellis modification of the Scarff-Bloom-Richardson grading system), the Gleason scoring system for the prognosis and diagnosis of prostate cancer, amongst others.

Because of its complexity, disease scoring systems, such as SLEDAI, BILAG, and other correlative tests, are most commonly applied in research or clinical trials to evaluate the effectiveness of new drugs. It is, however, impractical for routine use by clinicians (for example, Rheumatologists). A simple, accurate, molecular test is needed to improve patient care.

Disclosed herein are methods, assays and devices that identify differential patterns of peripheral-blood antibody binding to a peptide array. Differential binding of patient samples to the array results in specific binding patterns or signatures indicative of the disease state of the patient. These binding signatures can accurately determine or diagnose a disease activity, including but not limited to autoimmune disease activity, infectious disease activity, cancer activity, and diabetes disease activity. For example, the methods and devices disclosed herein can identify or determine an SLE patient's disease status, correlating with clinical assessment outcomes, such as SLEDAI or BILAG.

The differential binding activity or signatures, also referred to as "immunosignatures", obtained by the methods, devices and assays disclosed herein also correlate with known disease scoring systems. For example, the immunosignature binding patterns obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to patients analyzed and diagnosed with an immune-mediated disorder when compared to a known immune-mediated disease scoring system, including, for example, SLEDAI, SELENA-SLEDAI, BILAG, DAS28, TNM, the Nottingham grading system and/or the Gleason scoring system. In preferred embodiments, the known immune-mediated disease scoring system is SLEDAI or SELENA-SLEDAI. The immunosignature binding pattern identified may include, but is not limited to, a peptide sequence, a peptide motif, amino acid content or other distinguishing feature of the immunosignature binding patterns detected.

As disclosed herein, the AUC may be interpreted as the probability that a patient with active disease according to the known scoring system would have a higher value associated with the immunosignatures binding pattern than a patient with inactive disease according to the known scoring system.

In other embodiments, the immunosignature binding patterns for SLE patients obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to patients analyzed and diagnosed with an autoimmune disorder when compared to a known autoimmune disease scoring system, including, for example, SLEDAI, SELENA-SLEDAI, BILAG, DAS28 or other clinical autoimmune disease scoring systems.

In further embodiments, the immunosignature binding patterns for SLE patients obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to patients scoring lower than 2 using the SLEDAI or SELENA-SLEDAI scoring system.

In further embodiments, the immunosignature binding patterns for SLE patients obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to patients scoring between 2 and 8 using the SLEDAI or SELENA-SLEDAI scoring system.

In further embodiments, the immunosignature binding patterns for SLE patients obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to patients scoring at least 12 using the SLEDAI or SELENA-SLEDAI scoring system.

In yet further embodiments, at least 0.00005%, at least 0.0001%, at least 0.0005%, at least 0.0001%, at least 0.005%, at least 0.01%, at least 0.05%, at least 0.1%, at least 0.5%, at least 1.0%, at least 1.5%, at least 2%, at least 3%, at least 4%, at least 5% or at least 10% of the peptides comprising the immunosignature binding patterns obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to patients analyzed and diagnosed with an immune-mediated disorder using a known immune-mediated disease scoring system, including, for example, SLEDAI, SELENA-SLEDAI, BILAG, DAS28, TNM, the Nottingham grading system and/or the Gleason scoring system. In preferred embodiments, the known immune-mediated disease scoring system is SLEDAI or SELENA-SLEDAI.

In yet further embodiments, at least 0.00005%, at least 0.0001%, at least 0.0005%, at least 0.0001%, at least 0.005%, at least 0.01%, at least 0.05%, at least 0.1%, at least 0.5%, at least 1.0%, at least 1.5%, at least 2%, at least 3%, at least 4%, at least 5% or at least 10% of the peptides comprising the immunosignature binding patterns obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to SLE patients analyzed and diagnosed with a scoring lower than 2 using the SLEDAI or SELENA-SLEDAI scoring system.

In yet further embodiments, at least 0.00005%, at least 0.0001%, at least 0.0005%, at least 0.0001%, at least 0.005%, at least 0.01%, at least 0.05%, at least 0.1%, at least 0.5%, at least 1.0%, at least 1.5%, at least 2%, at least 3%, at least 4%, at least 5% or at least 10% of the peptides comprising the immunosignature binding patterns obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to SLE patients analyzed and diagnosed with a scoring between 2 and 8 using the SLEDAI or SELENA-SLEDAI scoring system.

In yet further embodiments, at least 0.00005%, at least 0.0001%, at least 0.0005%, at least 0.0001%, at least 0.005%, at least 0.01%, at least 0.05%, at least 0.1%, at least 0.5%, at least 1.0%, at least 1.5%, at least 2%, at least 3%, at least 4%, at least 5% or at least 10% of the peptides comprising the immunosignature binding patterns obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to SLE patients analyzed and diagnosed with a scoring of at least 12 using the SLEDAI or SELENA-SLEDAI scoring system.

In yet further embodiments, at least 1 peptide, at least 2 peptides, at least 3 peptides, at least 4 peptides, at least 5 peptides, at least 6 peptides, at least 7 peptides, at least 8 peptides, at least 9 peptides, at least 10 peptides, at least 15 peptides, at least 20 peptides, at least 25 peptides, at least 30 peptides, at least 35 peptides, at least 40 peptides, at least 45 peptides, at least 50 peptides, at least 55 peptides, at least 60 peptides, at least 65 peptides, at least 70 peptides, at least 75 peptides, at least 80 peptides, at least 85 peptides, at least 90 peptides, at least 95 peptides or at least 100 peptides of the immunosignature binding patterns obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to patients analyzed and diagnosed with an immune-mediated disorder using a known immune-mediated disease scoring system, including, for example, SLEDAI, SELENA-SLEDAI, BILAG, DAS28, TNM, the Nottingham grading system and/or the Gleason scoring system. In preferred embodiments, the known immune-mediated disease scoring system is SLEDAI or SELENA-SLEDAI.

In yet further embodiments, at least 1 peptide, at least 2 peptides, at least 3 peptides, at least 4 peptides, at least 5 peptides, at least 6 peptides, at least 7 peptides, at least 8 peptides, at least 9 peptides, at least 10 peptides, at least 15 peptides, at least 20 peptides, at least 25 peptides, at least 30 peptides, at least 35 peptides, at least 40 peptides, at least 45 peptides, at least 50 peptides, at least 55 peptides, at least 60 peptides, at least 65 peptides, at least 70 peptides, at least 75 peptides, at least 80 peptides, at least 85 peptides, at least 90 peptides, at least 95 peptides or at least 100 peptides of the immunosignature binding patterns obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to SLE patients analyzed and diagnosed with a scoring lower than 2 using the SLEDAI or SELENA-SLEDAI scoring system.

In yet further embodiments, at least 1 peptide, at least 2 peptides, at least 3 peptides, at least 4 peptides, at least 5 peptides, at least 6 peptides, at least 7 peptides, at least 8 peptides, at least 9 peptides, at least 10 peptides, at least 15 peptides, at least 20 peptides, at least 25 peptides, at least 30 peptides, at least 35 peptides, at least 40 peptides, at least 45 peptides, at least 50 peptides, at least 55 peptides, at least 60 peptides, at least 65 peptides, at least 70 peptides, at least 75 peptides, at least 80 peptides, at least 85 peptides, at least 90 peptides, at least 95 peptides or at least 100 peptides of the immunosignature binding patterns obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to SLE patients analyzed and diagnosed with a scoring between 2 and 8 using the SLEDAI or SELENA-SLEDAI scoring system.

In yet further embodiments, at least 1 peptide, at least 2 peptides, at least 3 peptides, at least 4 peptides, at least 5 peptides, at least 6 peptides, at least 7 peptides, at least 8 peptides, at least 9 peptides, at least 10 peptides, at least 15 peptides, at least 20 peptides, at least 25 peptides, at least 30 peptides, at least 35 peptides, at least 40 peptides, at least 45 peptides, at least 50 peptides, at least 55 peptides, at least 60 peptides, at least 65 peptides, at least 70 peptides, at least 75 peptides, at least 80 peptides, at least 85 peptides, at least 90 peptides, at least 95 peptides or at least 100 peptides of the immunosignature binding patterns obtained with the methods and arrays disclosed have an area under the receiver operator characteristic (ROC) curve (AUC) of at least 0.6, at least 0.65, at least 0.7, at least 0.75, at least 0.8, at least 0.85, at least 0.9, at least 0.95, at least 0.97, at least 0.99 or at least 1.0 when compared to SLE patients analyzed and diagnosed with a scoring of at least 12 using the SLEDAI or SELENA-SLEDAI scoring system.

In some embodiments, the immunosignature binding patterns obtained with the methods and arrays disclosed herein correlate with at least 50%, at least 55%, at least 60%, at least 65%, at least 70%, at least 75%, at least 80%, at least 85%, at least 90%, at least 95%, at least 96%, at least 97%, at least 98% or at least 99% of patients analyzed and diagnosed with an immune-mediated disorder when compared to patients analyzed using a known immune-mediated disease scoring system, including, for example, SLEDAI, SELENA-SLEDAI, BILAG, DAS28, TNM, the Nottingham grading system and/or the Gleason scoring system. In preferred embodiments, the known immune-mediated disease scoring system is SLEDAI or SELENA-SLEDAI.

In other embodiments, the immunosignature binding patterns for diagnosing or detecting autoimmune disorder in a patient obtained with the methods and arrays disclosed herein correlate with at least 50%, at least 55%, at least 60%, at least 65%, at least 70%, at least 75%, at least 80%, at least 85%, at least 90%, at least 95%, at least 96%, at least 97%, at least 98% or at least 99% of patients analyzed and diagnosed with an autoimmune disorder using an autoimmune disorder scoring system, such as the SLEDAI, SELENA-SLEDAI, DAS28 or BILAG scoring system.

In other embodiments, the immunosignature binding patterns for diagnosing or detecting SLE in a patient obtained with the methods and arrays disclosed herein correlate with at least 50%, at least 55%, at least 60%, at least 65%, at least 70%, at least 75%, at least 80%, at least 85%, at least 90%, at least 95%, at least 96%, at least 97%, at least 98% or at least 99% of patients analyzed and diagnosed with SLE when compared to patients scoring lower than 2 using the SLEDAI or SELENA-SLEDAI scoring system.

In other embodiments, the immunosignature binding patterns for diagnosing or detecting SLE in a patient obtained with the methods and arrays disclosed herein correlate with at least 50%, at least 55%, at least 60%, at least 65%, at least 70%, at least 75%, at least 80%, at least 85%, at least 90%, at least 95%, at least 96%, at least 97%, at least 98% or at least 99% of patients analyzed and diagnosed with SLE when compared to patients scoring between 2 and 12 using the SLEDAI or SELENA-SLEDAI scoring system.

In other embodiments, the immunosignature binding patterns for diagnosing or detecting SLE in a patient obtained with the methods and arrays disclosed herein correlate with at least 50%, at least 55%, at least 60%, at least 65%, at least 70%, at least 75%, at least 80%, at least 85%, at least 90%, at least 95%, at least 96%, at least 97%, at least 98% or at least 99% of patients analyzed and diagnosed with SLE when compared to patients scoring at least 12 using the SLEDAI or SELENA-SLEDAI scoring system.

In yet other embodiments, the immunosignature binding signals for diagnosing or detecting SLE in a patient obtained with the methods and arrays disclosed herein are higher when compared to patients scoring less than 2 using the SLEDAI or SELENA-SLEDAI scoring system. In yet other embodiments, the immunosignature binding signals for diagnosing or detecting SLE in a patient obtained with the methods and arrays disclosed herein are lower when compared to patients scoring less than 2 using the SLEDAI or SELENA-SLEDAI scoring system.

In yet other embodiments, the immunosignature binding signals for diagnosing or detecting SLE in a patient obtained with the methods and arrays disclosed herein are higher when compared to patients scoring between 2 and 8 using the SLEDAI or SELENA-SLEDAI scoring system. In yet other embodiments, the immunosignature binding signals for diagnosing or detecting SLE in a patient obtained with the methods and arrays disclosed herein are lower when compared to patients scoring between 2 and 8 using the SLEDAI or SELENA-SLEDAI scoring system.

In yet other embodiments, the immunosignature binding signals for diagnosing or detecting SLE in a patient obtained with the methods and arrays disclosed herein are higher when compared to patients scoring at least 12 using the SLEDAI or SELENA-SLEDAI scoring system. In yet other embodiments, the immunosignature binding signals for diagnosing or detecting SLE in a patient obtained with the methods and arrays disclosed herein are lower when compared to patients scoring at least 12 using the SLEDAI or SELENA-SLEDAI scoring system.

In still other embodiments, the immunosignature binding patterns for diagnosing or detecting an immune-mediated disease in a patient obtained with the methods and arrays disclosed herein are enriched by at least 100%, at least 125%, at least 150%, at least 175%, at least 200%, at least 225%, at least 250%, at least 275%, at least 300%, at least 350%, at least 400%, at least 450% or at least 500% in at least one amino acid for the peptides comprising the immunosignature for the immune-mediated disease.

Enriched motifs were identified from the list of significant peptides unless that list was less than 100 peptides long, in which case the top 500 peptides based on the p-value associated with a Welch's t-test were used. The different n-mers in this list of peptides was compared to the same sized n-mers in the total library to determine if any were enriched. Fold enrichment is calculated by determining the number of times a motif (e.g. ABCD) occurs in the list divided by the number of times the motif (ABCD) occurs in the library. This value is further divided by the relative number of times the motif type (e.g., tetramers) appears in the library (i.e., total number of all tetramers in the list divided by the total number of tetramers in the library). The Enrichment (E) calculation can be represented by:

$$E=(m/M)/(t/T)$$

where m is the number of times the motif occurs as part of the discriminating peptide list; M is the total number of times the motif occurs in the library; t is the number of times the motif type appears in the list; and T is the number of times the motif occurs in the library. Fold enrichment can also be reported as Percent enrichment, i.e., "Enrichment value" multiplied by 100.

In yet other embodiments, the immunosignature binding patterns for diagnosing or detecting an autoimmune disease in a patient obtained with the methods and arrays disclosed herein are enriched by at least 100%, at least 125%, at least 150%, at least 175%, at least 200%, at least 225%, at least 250%, at least 275%, at least 300%, at least 350%, at least 400%, at least 450% or at least 500% in at least one amino acid for the peptides comprising the immunosignature for the autoimmune disease or disorder. In preferred embodiments, the autoimmune disorder is SLE.

In yet other embodiments, the immunosignature binding patterns for diagnosing or detecting SLE in a patient obtained with the methods and arrays disclosed herein are enriched by at least 100%, at least 125%, at least 150%, at least 175%, at least 200%, at least 225%, at least 250%, at least 275%, at least 300%, at least 350%, at least 400%, at least 450% or at least 500% in at least one amino acid for the peptides comprising the immunosignature for detecting or diagnosing SLE.

In some embodiments, the immunosignature binding patterns for diagnosing or detecting an autoimmune disease in a patient obtained with the methods and arrays disclosed herein comprises at least 1, at least 2, at least 3, at least 4, at least 5, at least 6, at least 7, at least 8, at least 9 or at least 10 peptide motifs. In some embodiments, the motifs are at least 25% identical, at least 30% identical, at least 40% identical, at least 50% identical, at least 60% identical, at least 70% identical, at least 80% identical, at least 90% identical, at least 95% identical or at least 99% identical to peptides on the peptide array. In other embodiments, the motifs are at least 25% similar, at least 30% similar, at least 40% similar, at least 50% similar, at least 60% similar, at least 70% similar, at least 80% similar, at least 90% similar, at least 95% similar or at least 99% similar to peptides on the peptide array. In still other embodiments, the motifs for diagnosing or detecting in an autoimmune disease in a patient is at least one of the motifs or amino acids listed in FIGS. 13A-13G.

Treatments and Conditions

The methods and arrays of the invention provide methods, assays and devices for the detection and diagnosis of an autoimmune disorder. The methods and arrays of the embodiments disclosed herein can be used, for example, for screening of an immune disorder in a subject. A subject can be a human, a guinea pig, a dog, a cat, a horse, a mouse, a rabbit, and various other animals. A subject can be of any age, for example, a subject can be an infant, a toddler, a child, a pre-adolescent, an adolescent, an adult, or an elderly individual.

A condition of a subject can correspond to a disease or a healthy condition. In some embodiments, a condition of a subject is a healthy condition, and a method of the invention monitors the healthy condition. In some embodiments, a condition of a subject is a disease condition, and a method of the invention is used to diagnose/monitor a state and/or the progression of the condition. A method of the invention can also be used in the prevention of a condition. In some embodiments, a method of the invention is used in conjunction with a prophylactic treatment.

In some embodiments, a method of the invention is a method of diagnosing or determining the presence or absence of an autoimmune disorder in a subject, the method comprising: a. contacting a peptide array with a first biological sample from an individual patient or subject; b. detecting binding of antibodies in the first biological sample with the peptide array to obtain a first immunosignature profile; c. contacting a peptide array with a control sample derived from an individual with a known autoimmune disorder; d. detecting binding of antibody in the control sample with the peptide array to obtain a second immunosignature profile; e. comparing the first immunosignature profile to the second immunosignature profile to determine if a patient or subject has an autoimmune disease or disorder.

In yet other embodiments, a method of the invention is a method of determining the disease state or progression of an autoimmune disorder in a subject, the method comprising: a. contacting a peptide array with a first biological sample from an individual patient or subject with a known autoimmune disorder; b. detecting binding of antibodies in the first biological sample with the peptide array to obtain a first immunosignature profile; c. contacting a peptide array with a control sample derived from an individual with a known stage of an autoimmune disorder; d. detecting binding of antibody in the control sample with the peptide array to obtain a second immunosignature profile; e. comparing the first immunosignature profile to the second immunosignature profile to determine a disease stage or progression of a patient or subject with the autoimmune disease or disorder.

In some embodiments, the immunosignature may be used to augment or improve known biomarker analysis. For example, in systemic lupus erythrematosus (SLE), the biomarker may be anti-dsDNA antibodies, complement protein C3, complement protein C4, antinuclear antibody (ANA), proteinuria, malar rash, CNS manifestation, arthritis, cytopenia, discoid rash, oral ulcers, renal manifestation, immunologic, photosensitivity, serositis or combinations thereof. In some instances, the immunosignature may improve sensitivity and specificity of biomarker diagnoses or analyses. In other instances, the immunosignature may improve the accuracy of biomarker diagnoses or analyses. In yet other instances, the immunosignature may improve the assay performance by at least 10%, 20%, 30%, 40%, 50%, 60%, 70%, 80%, 90% or 99% of at assay or diagnostic kit using at least one biomarker.

An array and a method of the invention can be used to, for example, diagnose or detect if a patient or subject is afflicted with an autoimmune disease or disorder. Non-limiting examples of autoimmune diseases or disorders that can be diagnosed, monitored, prevented, and/or treated with an array and a method of the invention can include: systemic lupus erythematosus (SLE), rheumatoid arthritis, Sjogren's disease, multiple sclerosis, ulcerative colitis, psoriatic arthritis, scleroderma and/or type I diabetes.

In some embodiments, a method of the invention is a method for diagnosing or detecting an autoimmune disorder, the method comprising: a) contacting a peptide array with a first biological sample from a patient or subject; b) detecting binding of antibodies in the first biological sample with the peptide array to obtain a first immunosignature profile; c) contacting a peptide array with a control sample derived from an individual with a known autoimmune disease or disorder; d) detecting binding of antibody in the control sample with the peptide array to obtain a second immunosignature profile; e) comparing the first immunosignature profile to the second immunosignature profile and identifying differentially bound peptides that either bind less or more antibody in the first immunosignature profile as compared to the second immunosignature profile; and f) determining if the patient or subject has an autoimmune disease or disorder.

In some embodiments, a method of the invention is a method for determining the disease state or progression of an autoimmune disorder, the method comprising: a) contacting a peptide array with a first biological sample from a patient or subject with an autoimmune disease or disorder; b) detecting binding of antibodies in the first biological sample with the peptide array to obtain a first immunosignature profile; c) contacting a peptide array with a control sample derived from an individual with a known stage or state of an autoimmune disease or disorder; d) detecting binding of antibody in the control sample with the peptide array to obtain a second immunosignature profile; e) comparing the first immunosignature profile to the second immunosignature profile and identifying differentially bound peptides that either bind less or more antibody in the first immunosignature profile as compared to the second immunosignature profile; and f) determining the disease state or progression of the patient or subject with the autoimmune disease or disorder.

Non-limiting examples of disorders associated with the immune system can include: auto-immune disorders, inflammatory diseases, HIV, rheumatoid arthritis, diabetes mellitus type 1, systemic lupus erythematosus, scleroderma, multiple sclerosis, severe combined immunodeficiency (SCID), DiGeorge syndrome, ataxia-telangiectasia, seasonal allergies, perennial allergies, food allergies, anaphylaxis, mastocytosis, allergic rhinitis, atopic dermatitis, Parkinson's, Alzheimer's, hypersplenism, leukocyte adhesion deficiency, X-linked lymphoproliferative disease, X-linked agammaglobulinemia, selective immunoglobulin A deficiency, hyper IgM syndrome, autoimmune lymphoproliferative syndrome, Wiskott-Aldrich syndrome, chronic granulomatous disease, common variable immunodeficiency (CVID), hyperimmunoglobulin E syndrome, and Hashimoto's thyroiditis.

In preferred embodiments, the immune disorder is an auto-immune disorder. In some embodiments the autoimmune disorder is chosen from the group consisting of Type I diabetes, rheumatoid arthritis, multiple sclerosis, inflammatory bowel disease, systemic lupus erythematosus, psoriasis, and scleroderma.

In further embodiments, the methods, devices and assays disclosed herein measure binding of the samples used herein to generate an immunosignature. Binding activity measured in some instances relates to the binding of mimotope or non-epitope binding interactions. In some instances, the mimotope binding interactions may have higher binding affinity than the cognate epitope. In other instances, the mimotope binding interactions may have lower binding affinity than the cognate epitope. While the corresponding solution-phase binding of the measured binding interactions may be low, the microarrays used and disclosed herein are constructed to enhance the detection of a range of binding interactions that may not be detected in solution phase-based assays.

Accordingly, in some instances, the microarrays used in conjunction with the methods, devices and assays provided herein are constructed to enhance the interaction and detection of binding activities between the samples used herein and the peptides on the array. In some instances, identical or the same peptides are spaced within an assigned feature of the microarray at high density, in some instances between about 0.1 nm to 20 nm, between about 0.5 nm to 15 nm, between about 0.5 nm to 10 nm, between about 0.5 nm to about 7 nm apart, between about 1 nm to about 6 nm apart, between about 1 nm to about 5 nm apart, between about 1 nm to about 4 nm apart, between about 1 nm to about 3 nm apart, between about 1 nm to about 2 nm apart, between about 1 to about 1.5 nm apart, between about 10 nm to 20 nm, between about 15 nm to 20 nm, between about 10 nm to 15 nm, between about 12 nm to 17 nm, between about 16 nm to 20 nm or between about 14 nm to 18 nm. In some instances, identical or the same peptides are spaced within an assigned feature of the microarray at less than about 7 nm, less than about 6 nm, less than about 5 nm, less than about 4 nm, less than about 3 nm, less than about 2 nm or less than about 1 nm apart from each other. In other instances, identical or the same peptides are spaced within an assigned feature of the microarray at more than about 5 nm, more than about 6 nm, more than about 7 nm, more than about 8 nm, more than about 9 nm, more than about 10 nm, more than about 11 nm, more than about 12 nm, more than about 13 nm, more than about 14 nm, more than about 15 nm, more than about 16 nm, more than about 17 nm, more than about 18 nm, more than about 19 nm, more than about 20 nm. In yet other instances, identical or the same peptides are spaced within an assigned feature on the microarray at about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, or about 20 nm.

In some embodiments, the peptides on the microarrays used herein are synthesized in situ on the surface of the array, or are deposited and bound to the surface of the array. In some instances, the peptides are synthesized in either manner using less than 20 different amino acids. In other instances, at least the amino acids methionine, cysteine, isoleucine and threonine are excluded during synthesis of the peptides.

The invention can provide a method of preventing a condition, the method comprising: a) providing a complex biological sample from a subject; b) contacting the complex biological sample to a peptide array, wherein the peptide array comprises different peptides capable of binding of at least one antibody in the complex biological sample; c) measuring an binding of the complex biological sample to a plurality of the different peptides to form an immunosignature; d) associating the immunosignature with a condition; and e) receiving a treatment for the condition. In some embodiments, a method of the invention can be used in conjunction with a prophylactic treatment.

In some embodiments, the patient or subject suffers from an infection of, for example, a pathogen. A pathogen can be a pathogenic virus or a pathogenic bacteria. An infection with a pathogenic viruses and/or a pathogenic bacteria can cause a condition, for example, an inflammation. Non-limiting examples of pathogenic bacteria can be found in the: a) *Bordetella* genus, such as *Bordetella pertussis* species; b) *Borrelia* genus, such *Borrelia burgdorferi* species; c) *Brucelia* genus, such as *Brucella abortus, Brucella canis, Brucela meliterisis*, and/or *Brucella suis* species; d) *Campylobacter* genus, such as *Campylobacter jejuni* species; e) *Chlamydia* and *Chlamydophila* genuses, such as *Chlamydia pneumonia, Chlamydia trachomatis*, and/or *Chlamydophila psittaci* species; f) *Clostridium* genus, such as *Clostridium botulinum, Clostridium difficile, Clostridium perfringens, Clostridium tetani* species; g) *Corynebacterium* genus, such as *Corynebacterium diphtheria* species; h) *Enterococcus* genus, such as *Enterococcus faecalis*, and/or *Enterococcus faecium* species; i) *Escherichia* genus, such as *Escherichia coli* species; j) *Francisella* genus, such as *Francisella tularensis* species; k) *Haemophilus* genus, such as *Haemophilus influenza* species; l) *Helicobacter* genus, such as *Helicobacter pylori* species; m) *Legionella* genus, such as *Legionella pneumophila* species; n) Leptospira genus, such as Leptospira interrogans species; o) *Listeria* genus, such as *Listeria monocytogenes* species; p) *Mycobacterium* genus, such as *Mycobacterium leprae, Mycobacterium tuberculosis*, and/or *mycobacterium ulcerans* species; q) *Mycoplasma* genus, such as *Mycoplasma* pneumonia species; r) *Neisseria* genus, such as *Neisseria gonorrhoeae* and/or *Neisseria meningitidia* species; s) *Pseudomonas* genus, such as *Pseudomonas aeruginosa* species; t) *Rickettsia* genus, such as *Rickettsia rickettsii* species; u) *Salmonella* genus, such as *Salmonella typhi* and/or *Salmonella typhimurium* species; v) *Shigella* genus, such as *Shigella sonnei* species; w) *Staphylococcus* genus, such as *Staphylococcus aureus, Staphylococcus epidermidis*, and/or *Staphylococcus saprophyticus* species; x) *Streptococcus* genus, such as *Streptococcus aga-*

*lactiae, Streptococcus pneumonia*, and/or *Streptococcus pyogenes* species; y) *Treponema* genus, such as *Treponema pallidum* species; z) *Vibrio* genus, such as *Vibrio cholera*; and/or aa) *Yersinia* genus, such as *Yersinia pestis* species.

Non-limiting examples of viruses can be found in the following families of viruses and are illustrated with exemplary species: a) Adenoviridae family, such as Adenovirus species; b) Herpesviridae family, such as Herpes simplex type 1, Herpes simplex type 2, Varicella-zoster virus, Epstein-barr virus, Human cytomegalovirus, Human herpesvirus type 8 species; c) Papillomaviridae family, such as Human papillomavirus species; d) Polyomaviridae family, such as BK virus, JC virus species; e) Poxviridae family, such as Smallpox species; f) Hepadnaviridae family, such as Hepatitis B virus species; g) Parvoviridae family, such as Human bocavirus, Parvovirus B19 species; h) Astroviridae family, such as Human astrovirus species; i) Caliciviridae family, such as Norwalk virus species; j) Flaviviridae family, such as Hepatitis C virus, yellow fever virus, dengue virus, West Nile virus species; k) Togaviridae family, such as Rubella virus species; l) Hepeviridae family, such as Hepatitis E virus species; m) Retroviridae family, such as Human immunodeficiency virus (HIV) species; n) Orthomyxoviridaw family, such as Influenza virus species; o) Arenaviridae family, such as Guanarito virus, Junin virus, Lassa virus, Machupo virus, and/or Sabiá virus species; p) Bunyaviridae family, such as Crimean-Congo hemorrhagic fever virus species; q) Filoviridae family, such as Ebola virus and/or Marburg virus species; Paramyxoviridae family, such as Measles virus, Mumps virus, Parainfluenza virus, Respiratory syncytial virus, Human metapneumovirus, Hendra virus and/or Nipah virus species; r) Rhabdoviridae genus, such as Rabies virus species; s) Reoviridae family, such as Rotavirus, Orbivirus, Coltivirus and/or Banna virus species. In some embodiments, a virus is unassigned to a viral family, such as Hepatitis D.

In some embodiments, the invention provides a method of providing a treatment, the method comprising: a) receiving a complex biological sample from a subject; b) contacting the complex biological sample to a peptide array, wherein the peptide array comprises different peptides capable of binding of at least one antibody in the biological sample; c) measuring the binding of the antibody to a plurality of the different peptides to form an immunosignature; d) associating the immunosignature with a condition; and e) providing the treatment for the condition.

In some embodiments, the invention can provide a method of diagnosis or detection of an autoimmune disorder, the method comprising: a) receiving a complex biological sample from a subject; b) contacting the complex biological sample to a peptide array, wherein the peptide array comprises different peptides capable of binding of at least one antibody in the biological sample; c) measuring the binding of the antibody to a group of different peptides in the peptide array to form an immunosignature; and d) detecting or diagnosing an autoimmune condition based on the immunosignature.

In some embodiments, a method of the invention can be used as a method of diagnosing, monitoring, and treating a condition. A method of treating a condition can require the prescription of a therapeutic agent targeted to treat the subject's condition or disease. In some embodiments, a therapeutic agent can be prescribed in a range of from about 1 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg. A user would also adjust the dosage requirements of the therapeutic agent depending upon, for example, severity of the disease, physical parameters of the subject (weight, height and other characteristics) as well as frequency of administration of the prescribed therapeutic agent.

In some embodiments, at least 1 mg, at least 5 mg, at least 15 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 80 mg, at least 85 mg, at least 90 mg, at least 100 mg, at least 150 mg, at least 200 mg, at least 250 mg, at least 300 mg, at least 350 mg, at least 400 mg, at least 450 mg, at least 500 mg, at least 550 mg, at least 600 mg, at least 650 mg, at least 700 mg, at least 750 mg, at least 800 mg, at least 850 mg, at least 900 mg, at least 950 mg, or at least 1000 mg of the therapeutic agent is prescribed.

The arrays and methods of the invention can be used by a user to determine the health state or condition of a subject or patient. A plurality of users can use a method of the invention to identify and/or provide a treatment of a condition. A user can be, for example, a human who wishes to monitor one's own health. A user can be, for example, a health care provider. A health care provider can be, for example, a physician. In some embodiments, the user is a health care provider attending the subject. Non-limiting examples of physicians and health care providers that can be users of the invention can include, an anesthesiologist, a bariatric surgery specialist, a blood banking transfusion medicine specialist, a cardiac electrophysiologist, a cardiac surgeon, a cardiologist, a certified nursing assistant, a clinical cardiac electrophysiology specialist, a clinical neurophysiology specialist, a clinical nurse specialist, a colorectal surgeon, a critical care medicine specialist, a critical care surgery specialist, a dental hygienist, a dentist, a dermatologist, an emergency medical technician, an emergency medicine physician, a gastrointestinal surgeon, a hematologist, a hospice care and palliative medicine specialist, a homeopathic specialist, an infectious disease specialist, an internist, a maxillofacial surgeon, a medical assistant, a medical examiner, a medical geneticist, a medical oncologist, a midwife, a neonatal-perinatal specialist, a nephrologist, a neurologist, a neurosurgeon, a nuclear medicine specialist, a nurse, a nurse practioner, an obstetrician, an oncologist, an oral surgeon, an orthodontist, an orthopedic specialist, a pain management specialist, a pathologist, a pediatrician, a perfusionist, a periodontist, a plastic surgeon, a podiatrist, a proctologist, a prosthetic specialist, a psychiatrist, a pulmonologist, a radiologist, a surgeon, a thoracic specialist, a transplant specialist, a vascular specialist, a vascular surgeon, and a veterinarian. A diagnosis identified with an array and a method of the invention can be incorporated into a subject's medical record. The immunosignature obtained can then be used for identifying therapeutic targets and developing treatments for the individual against the identified autoimmune disorder according to the methods and devices disclosed herein.

Accordingly, the methods, systems and array devices disclosed herein are capable of screening, identifying therapeutic targets, identifying vaccine targets, and/or treating a disease and/or condition at an early stage of the disease and/or condition. For example, the methods, systems and array devices disclosed herein are capable of detecting, diagnosing and monitoring a disease and/or condition days or weeks before traditional biomarker-based assays. Moreover, only one array, i.e., one immunosignature assay, is needed to detect, diagnose and monitor a side spectra of diseases and conditions, including inflammatory conditions, cancer and pathogenic infections.

Classification Algorithms

A plurality of algorithms and classifiers can be used to classify and/or analyze data obtained in an Immunosignaturing array. The Naïve Bayes' algorithm can accommodate the complex patterns hidden within multilayered immunosignaturing microarray data due to its fundamental mathematical properties. A basic classification algorithm, Linear Discriminant Analysis (LDA) is widely used in analyzing biomedical data in order to classify two or more disease classes. LDA can be, for example, a classification algorithm. A more complex classification method, Support Vector Machines (SVM), uses mathematical kernels to separate classes by a hyperplane, projecting the original predictors to higher-dimensional spaces. Some common kernels include linear, polynomial, sigmoid or radial basis functions. A comparative study of common classifiers described in the art is described in (Kukreja et al, BMC Bioinformatics. 2012; 13: 139).

Array Platform

In some embodiments, disclosed herein are methods and process that provide for array platforms that allow for increased diversity and fidelity of chemical library synthesis, The array platforms comprises a plurality of individual features on the surface of the array. Each feature typically comprises a plurality of individual molecules synthesized in situ on the surface of the array, wherein the molecules are identical within a feature, but the sequence or identity of the molecules differ between features. The array molecules include, but are not limited to nucleic acids (including DNA, RNA, nucleosides, nucleotides, structure analogs or combinations thereof), peptides, peptide-mimetics, and combinations thereof and the like, wherein the array molecules may comprise natural or non-natural monomers within the molecules. Such array molecules include the synthesis of large synthetic peptide arrays. In some embodiments, a molecule in an array is a mimotope, a molecule that mimics the structure of an epitope and is able to bind an epitope-elicited antibody. In some embodiments, a molecule in the array is a paratope or a paratope mimetic, comprising a site in the variable region of an antibody (or T cell receptor) that binds to an epitope an antigen. In some embodiments, an array of the invention is a peptide array comprising random, pseudo-random or maximally diverse peptide sequences.

The technologies disclosed herein include a photolithographic array synthesis platform that merges semiconductor manufacturing processes and combinatorial chemical synthesis to produce array-based libraries on silicon wafers. By utilizing the tremendous advancements in photolithographic feature patterning, the array synthesis platform is highly-scalable and capable of producing combinatorial chemical libraries with 40 million features on an 8-inch wafer. Photolithographic array synthesis is performed using semiconductor wafer production equipment in a class 10,000 cleanroom to achieve high reproducibility. When the wafer is diced into standard microscope slide dimensions, each slide contains more than 3 million distinct chemical entities.

In some embodiments, arrays with chemical libraries produced by photolithographic technologies disclosed herein are used for immune-based diagnostic assays, for example called immunosignature assays. Using a patient's antibody repertoire from a drop of blood bound to the arrays, a fluorescence binding profile image of the bound array provides sufficient information to classify disease vs. healthy.

In some embodiments, immunosignature assays are being developed for clinical application to diagnose/monitor autoimmune diseases and to assess response to autoimmune treatments. Exemplary embodiments of immunosignature assays is described in detail in US Pre-Grant Publication No. 2012/0190574, entitled "Compound Arrays for Sample Profiling" and US Pre-Grant Publication No. 2014/0087963, entitled "Immunosignaturing: A Path to Early Diagnosis and Health Monitoring", both of which are incorporated by reference herein for such disclosure. The arrays developed herein incorporate analytical measurement capability within each synthesized array using orthogonal analytical methods including ellipsometry, mass spectrometry and fluorescence. These measurements enable longitudinal qualitative and quantitative assessment of array synthesis performance.

In some embodiments, detection of antibody binding on a peptide array poses some challenges that can be addressed by the technologies disclosed herein. Accordingly, in some embodiments, the arrays and methods disclosed herein utilize specific coatings and functional group densities on the surface of the array that can tune the desired properties necessary for performing immunosignature assays. For example, non-specific antibody binding on a peptide array may be minimized by coating the silicon surface with a moderately hydrophilic monolayer polyethylene glycol (PEG), polyvinyl alcohol, carboxymethyl dextran, and combinations thereof. In some embodiments, the hydrophilic monolayer is homogeneous. Second, synthesized peptides are linked to the silicon surface using a spacer that moves the peptide away from the surface so that the peptide is presented to the antibody in an unhindered orientation.

Detector Device

In some embodiments, the systems, platforms and methods disclosed herein include a detector device for detecting binding on the array formats disclosed herein, including antibody binding on the peptide arrays disclosed herein. In some embodiments, used in conjunction with optical detection methods (ccd, pmt, other optical detector, optical filters and other optical detection devices), detection of antibody binding is reported via optical detection in real-time or on a timed interval. In certain instances, quantification of final binding activity is reported via optical detection converted to AFU (arbitrary fluorescence units) or translated to electrical signal via impedance measurement or other electrochemical sensing. In other instances, antibody binding is detected by an emission or absorption of light or electromagnetic energy, either in the visible range or otherwise from an optically-detectable label on a probe applied to the peptide device. Optically detectable labels include, without limitation, fluorescent, chemiluminescent, electrochemiluminescent, luminescent, phosphorescent, fluorescence polarization, and charge labels. In some instances, a fluorescently labeled probe is active only in the presence of a specific target or antibody so that a fluorescent response from a sample signifies the presence of the target or antibody.

In some instances, light delivery schemes are utilized to provide the optical excitation and/or emission and/or detection of antibody binding. In certain embodiments, this includes using the flow cell materials (thermal polymers like acrylic (PMMA) cyclic olefin polymer (COP), cyclic olefin co-polymer, (COC), etc.) as optical wave guides to remove the need to use external components. In addition, in some instances light sources—light emitting diodes—LEDs, vertical-cavity surface-emitting lasers—VCSELs, and other lighting schemes are integrated directly inside the cartridge or detection device or built directly onto the peptide array surface to have internally controlled and powered light sources. PMTs, CCDs, or CMOS detectors can also be built into the detection device or cartridge.

Digital Processing Device

In some embodiments, the systems, platforms, software, networks, and methods described herein include a digital processing device, or use of the same. In further embodiments, the digital processing device includes one or more hardware central processing units (CPUs), i.e., processors that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, a digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, a digital processing device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, a digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, a digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, a digital processing device includes a digital camera. In some embodiments, a digital camera captures digital images. In some embodiments, the digital camera is an autofocus camera. In some embodiments, a digital camera is a charge-coupled device (CCD) camera. In further embodiments, a digital camera is a CCD video camera. In other embodiments, a digital camera is a complementary metal-oxide-semiconductor (CMOS) camera. In some embodiments, a digital camera captures still images. In other embodiments, a digital camera captures video images. In various embodiments, suitable digital cameras include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and higher megapixel cameras, including increments therein. In some embodiments, a digital camera is a standard definition camera. In other embodiments, a digital camera is an HD video camera. In further embodiments, an HD video camera captures images with at least about 1280× about 720 pixels or at least about 1920×about 1080 pixels. In some embodiments, a digital camera captures color digital images. In other embodiments, a digital camera captures grayscale digital images. In various embodiments, digital images are stored in any suitable digital image format. Suitable digital image formats include, by way of non-limiting examples, Joint Photographic Experts Group (JPEG), JPEG 2000, Exchangeable image file format (Exif), Tagged Image File Format (TIFF), RAW, Portable Network Graphics (PNG), Graphics Interchange Format (GIF), Windows® bitmap (BMP), portable pixmap (PPM), portable graymap (PGM), portable bitmap file format (PBM), and WebP. In various embodiments, digital images are stored in any suitable digital video format. Suitable digital video formats include, by way of non-limiting examples, AVI, MPEG, Apple® QuickTime®, MP4, AVCHD®, Windows Media®, DivX™, Flash Video, Ogg Theora, WebM, and RealMedia.

Non-Transitory Computer Readable Storage Medium

In some embodiments, the systems, platforms, software, networks, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the systems, platforms, software, networks, and methods disclosed herein include at least one computer program. A computer program includes a sequence of instructions, executable in the digital processing device's CPU, written to perform a specified task. In light of the disclosure provided herein, those of skill in the art will recognize that a computer program may be written in various versions of various languages. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. A web application for providing a career development network for artists that allows artists to upload information and media files, in some embodiments, includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

The systems, platforms, software, networks, and methods disclosed herein include, in various embodiments, software, server, and database modules. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

EXAMPLES

Example 1—Testing of SLE Patient Samples

Background/Methods: The study design consisted of 356 samples from 183 patients who met ACR criteria for SLE at the time of diagnosis. The samples were selected to cover a wide range of SLEDAI scores correlated with the collected samples, which ranged from remission (SLEDAI score=0), mild (SLEDAI score=1-4), moderate (SLEDAI score=5-10) and severe (SLEDAI score greater than 11).

The patients were screened according to criteria developed by the American College of Rheumatology (ACR) to diagnose and identify patients with SLE. 90% of the subjects in the study were female, age range between 1 and 69 years of age (median of 39 years), with 52% of the subjects of Hispanic origin, 31% of African-American origin, 12% of Afro-Caribbean origin and 5% other or of mixed origin.

Patient sample were collected for up to 10 time points with the number of blood draws per patient ranging from 1 to 10 blood draws. A median of 6 months (range of 1 week to 4 years) were measured between blood draws. The samples were incubated on peptide arrays containing 126,000 unique peptides, washed, incubated with a secondary antibody to visualize peptide:antibody interactions on the array, washed again and imaged.

The data was processed by measuring the intensities of each data point, which was then logarithmically transformed, and normalized by subtracting its median intensity. Peptides associated with active disease were identified by t-test; peptides that correlate with SLEDAI scores were identified by Pearson correlation. Support Vector Machine (SVM) classifiers were employed to train and distinguish remission from increasing levels of SLE activity in each sample. See Cortes, C.; Vapnik, V. (1995). "Support-vector networks". Machine Learning. 20 (3): 273-297. SVMs find the optimal hyperplane that separates classes of peptides, the instant case based on immunosignature peptide signals. In "feature space" each peptide's signal is a dimension that characterizes each sample. "Support Vectors" are training samples that define the boundary between the classes, i.e., those data points hardest to classify)

Figure 3:
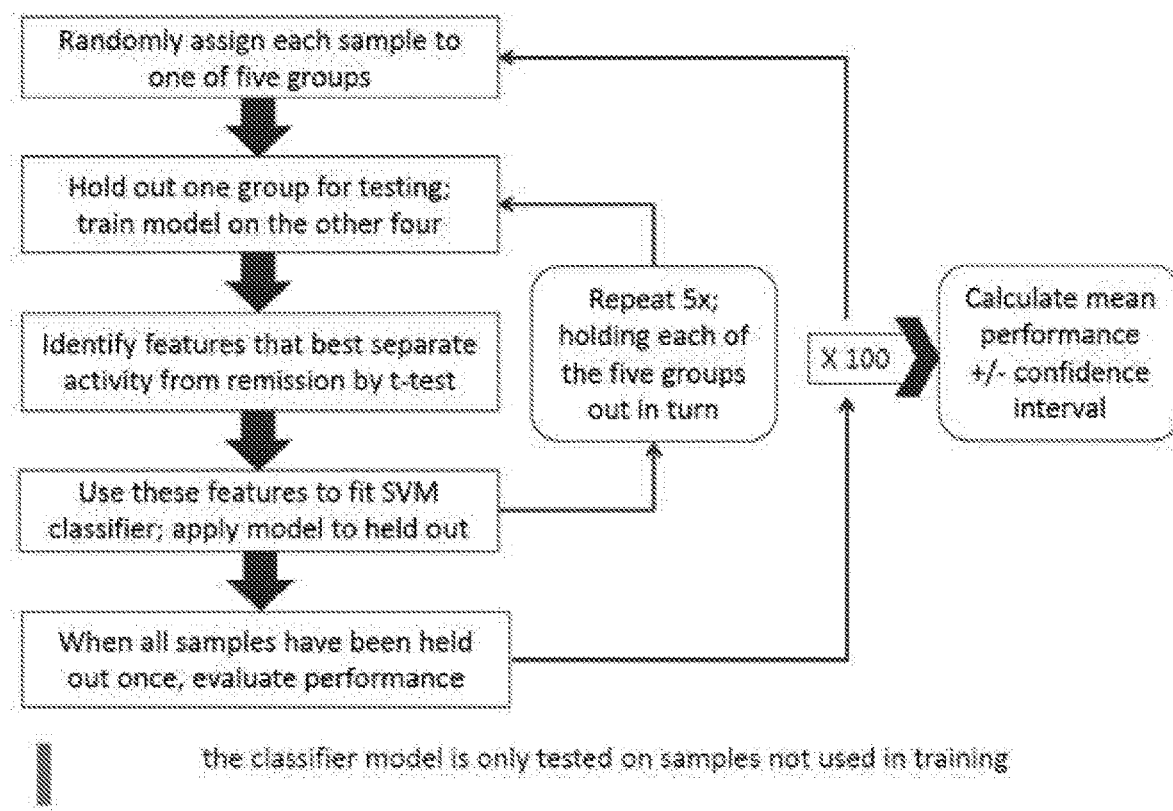
FIG. 3 is a pathway showing how a self protein/antigen can lead to up-regulation and down-regulation of an immunosignature in peptide microarrays.

Regression models of SLEDAI were also employed and trained using the Elastic Net Feature selection (see, e.g., Zou, Hui; Hastie, Trevor (2005). "Regularization and Variable Selection via the Elastic Net". Journal of the Royal Statistical Society, Series B: 301-320; Hastie, Tibshirani and Friedman, *The Elements of Statistical Learning*, $2^{nd}$ ed. (2008)) procedure to constrain model complexity. The Elastic Net approach applies Ridge Regression and LASSO penalties, where correlated features tend to be removed as groups. Briefly, Ridge Regression constrains the sum of coefficients to reduce overfit while reducing magnitude of coefficients, but does not eliminate features. The LASSO approach adds a quadratic term that leads to feature selection, but feature selection is unstable when features are correlated. Five-fold cross validation was used to correct for overfit. See FIG. 3; see also Frank. E Harrell, Jr., *Regression Modelling Strategies*, Springer Science+Business Media Inc. (2001).

Figure 4:
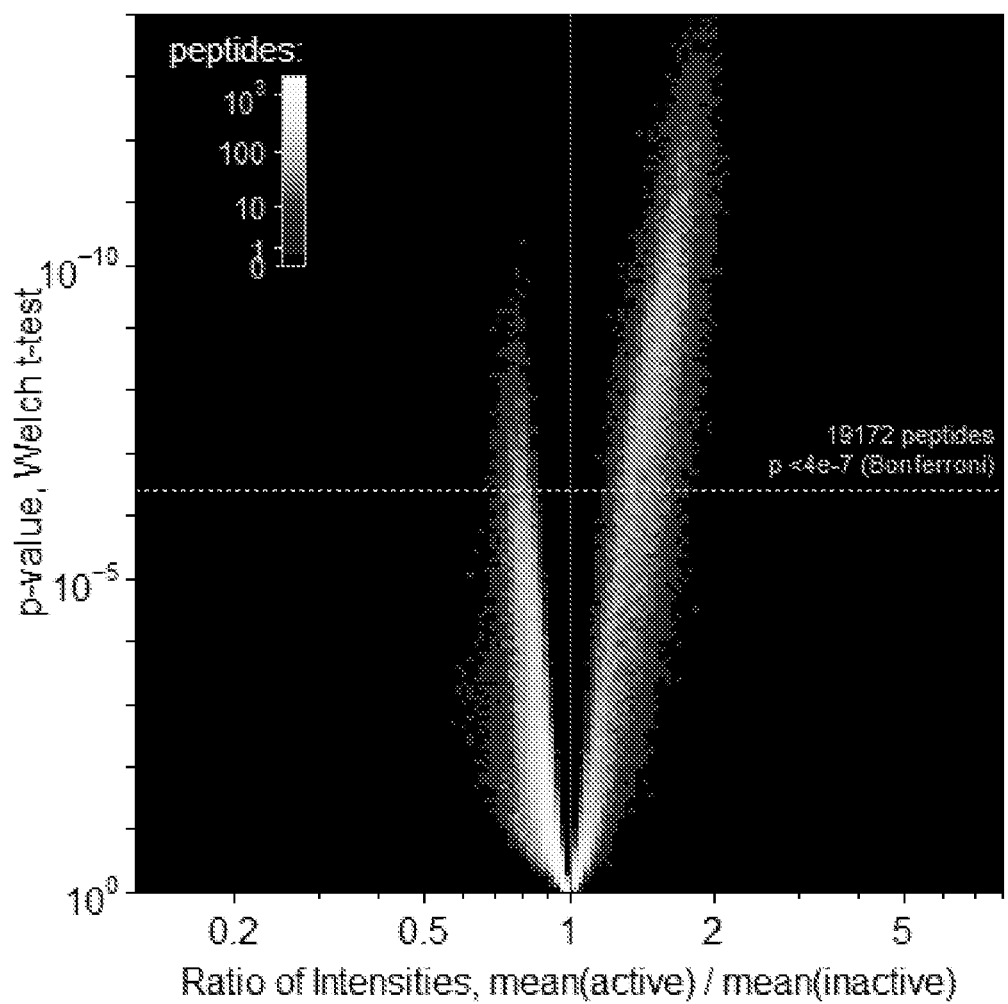
FIG. 4 is a volcano plot of peptides distinguishing active SLE disease versus inactive SLE disease.
Figure 5:
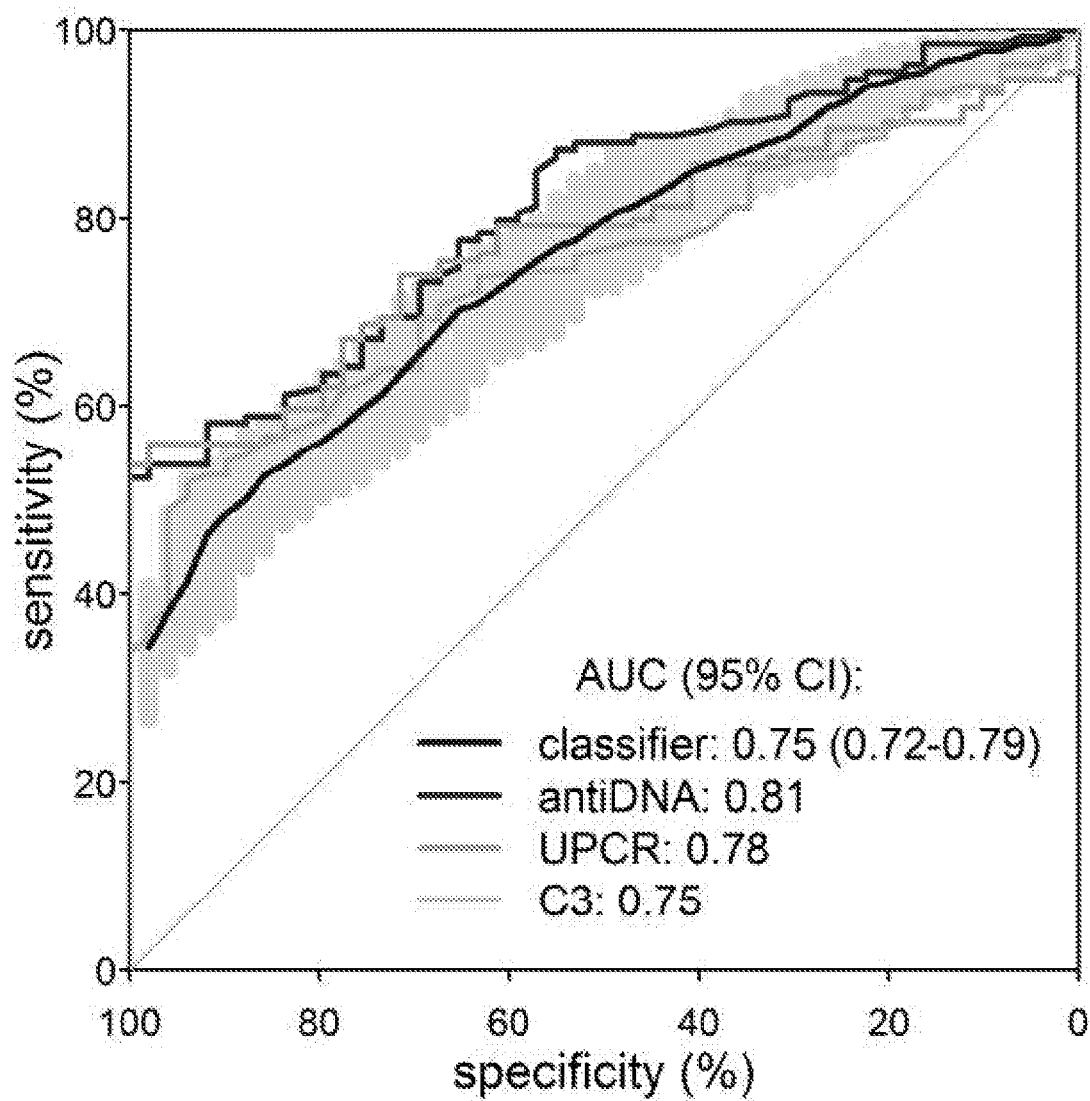
FIG. 5 are Receiver-Operator Characteristic (ROC) curves for an immunosignature (IMS) model of disease activity as compared to variety of biomarkers as (anti-dsDNA, UPCR (urine protein/creatinine ratio) and C3 protein) set forth in the SLEDAI index.
Figure 6:
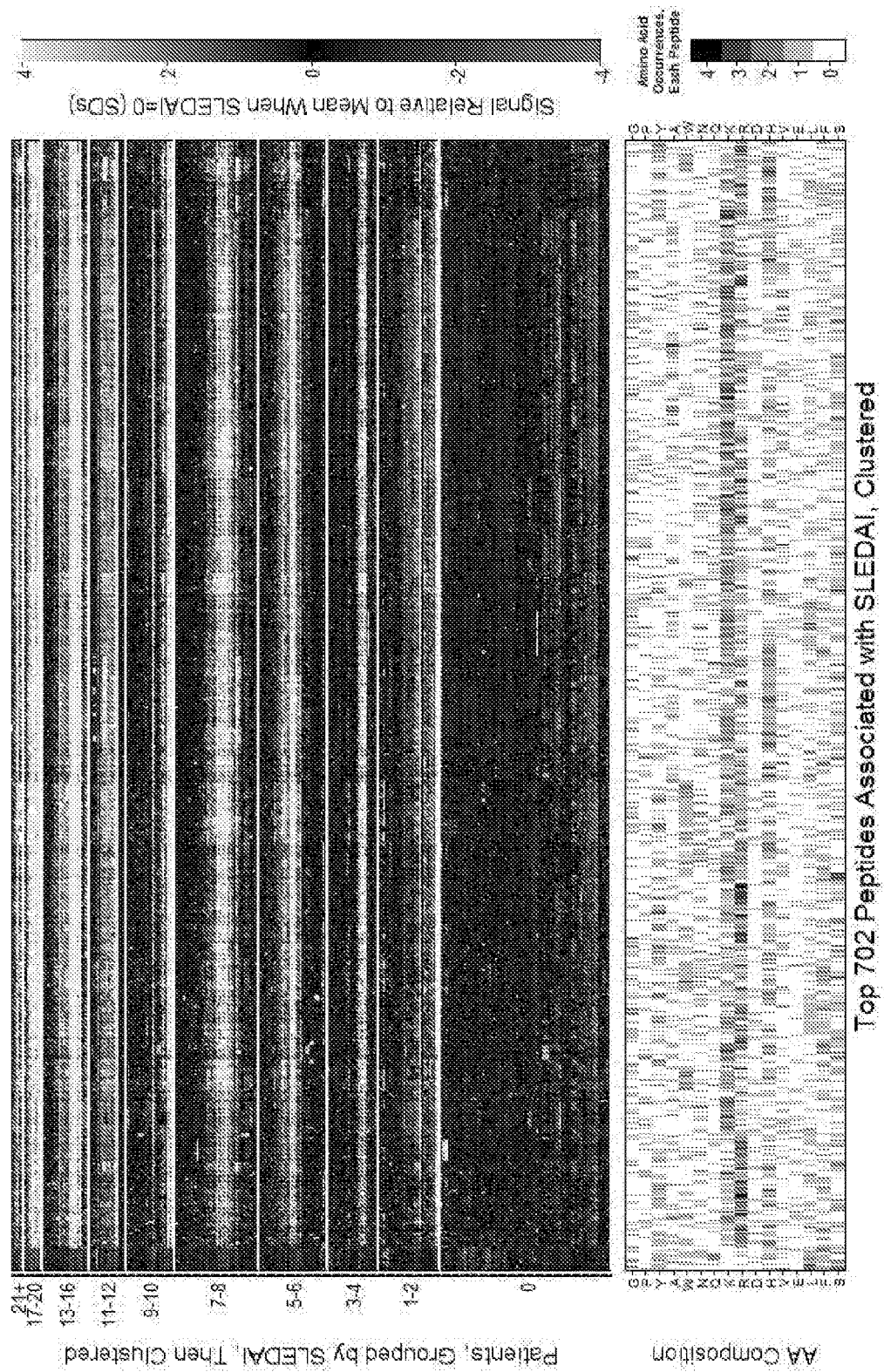
FIG. 6 illustrates a heat map of the top 702 peptides based on t-test p-values between SLE subjects.
Figure 7:
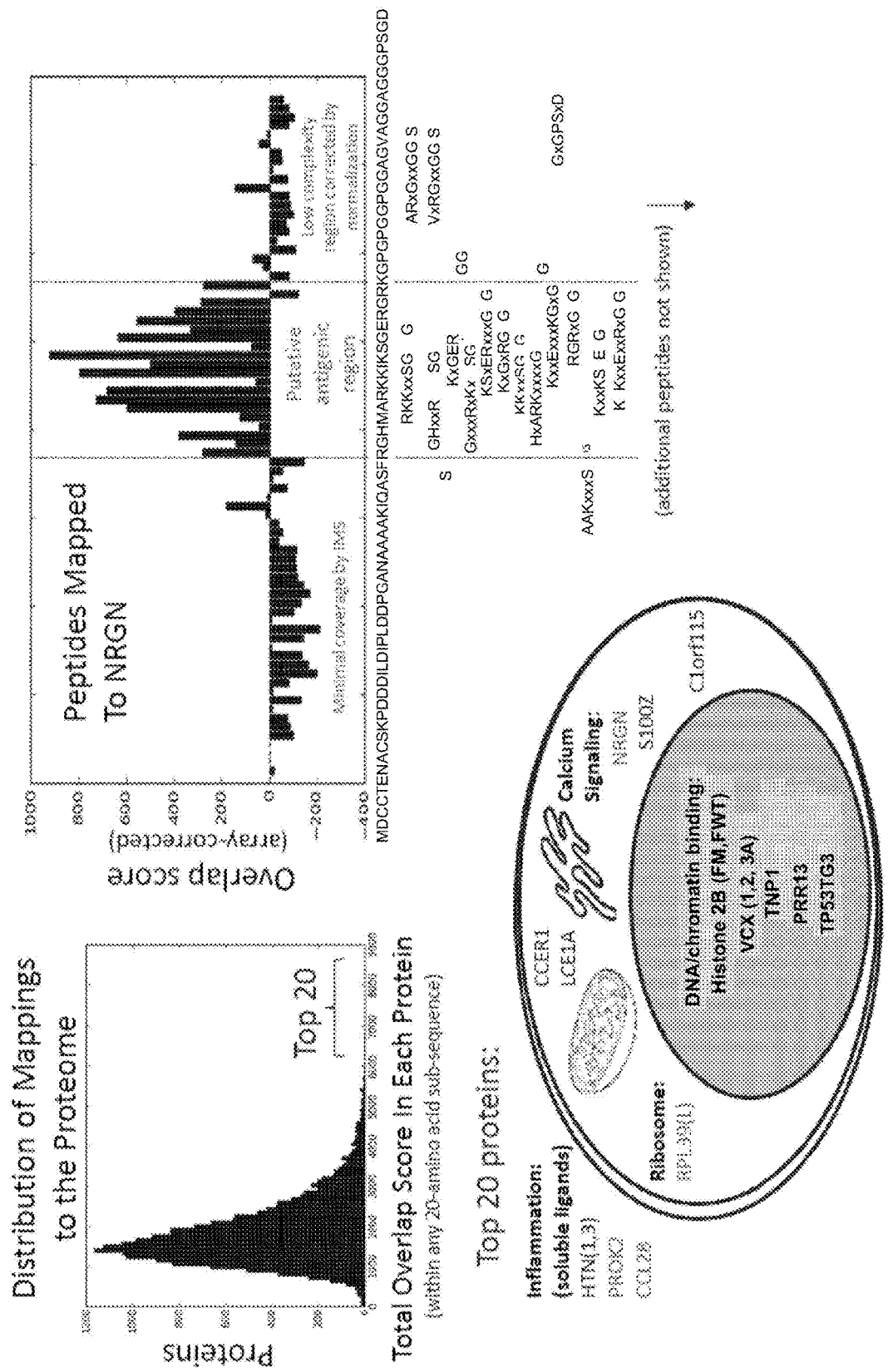
FIG. 7 shows the immunosignature (IMS) peptides that map to known and putative SLE antigens.

Results: FIG. 4 illustrates a volcano plot of peptides that distinguish active SLE from inactive (remission) SLE patients. The x-axis is the p-value obtained (Welch t-test) for the ratio of mean active disease (mean(active)) vs. mean inactive disease (mean (inactive)). The discriminating peptides obtained with immunosignature peptide arrays (IMS) was additionally plotted against sensitivity and specificity performance for anti-ds DNA, UPCR (urine protein/creatinine ratio) and C3 protein biomarker measurements. FIG. 5 shows Receiver-Operator Characteristic curves for an Immunosignature (IS) model of disease activity compared to biomarkers ds-DNA, C3, and proteinuria, for identifying patients with active disease (SLEDAI>0). The gray region indicates the 95% confidence interval of the IS Model, assessed using 5-fold cross validation. Discrimination was improved by training on extreme scores (SLEDAI>8 vs. 0), and performance was greater when applied to extreme contrasts. For example, a classifier of SLEDAI>15 vs. 0 had an AUC of 0.90 (95% CI 0.88-0.92). Preliminary analysis indicates that samples may be binned by IS into low, medium, and high disease activity. Correlations of a linear IS model ($r^2$=0.23), C3 ($r^2$=0.17) and anti-dsDNA ($r^2$=0.13) to SLEDAI were also determined FIG. 6 illustrates the top 702 peptides in the assay that were associated with SLEDAI results. The patients were first grouped by SLEDAI test scores, then clustered according to the peptides identified. The amino acid composition of each top associated peptide was also identified. The top peptides were used to search a human proteome database to determine peptides that aligned with known human proteins. See FIG. 7. Total overlap scores were first obtained to map the distribution of the discrimination peptides to the proteome. The top 20 overlap scores were further analyzed, and found to correspond with known proteins involved in inflammation, including HTN (1,3), PROK2 and CCL28, as well as calcium signaling (for example, NRGN and S100Z), ribosomal proteins (RPL39(L)), and proteins associated with DNA and chromatin regulation, including Histone 2B (FM, FWT), VCX (1, 2, 3A), TNP1, PRR13 and TP53TC3. Moreover, alignment was also found with uncharacterized proteins, including CCER1, LCE1A and C1orf115. An alignment of exemplary peptides to NRGN is also shown, with characteristics common to the discriminating peptides obtained.

Figure 8:
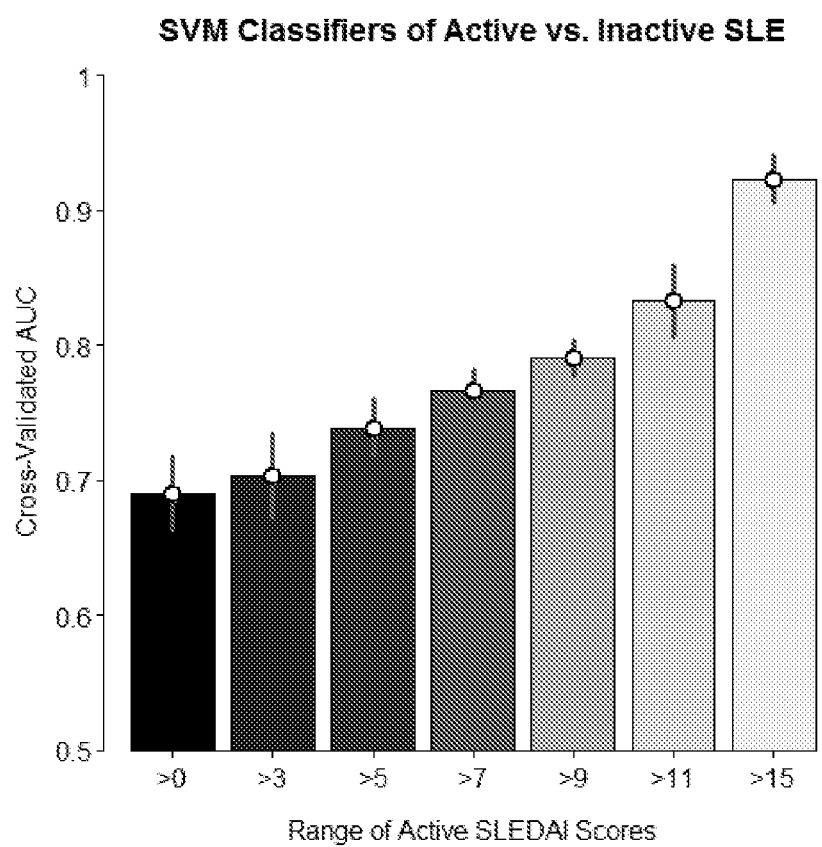
FIG. 8 shows the cross-validated SVM classifier predictions of a subject, demonstrating that higher SLE activity is easily distinguished from remission.

FIG. 8 shows a range of SVM classifiers of active vs. inactive SLE. The graph demonstrates that the higher activity of SLE is easily distinguished from SLE subjects in remission.

Figure 9:
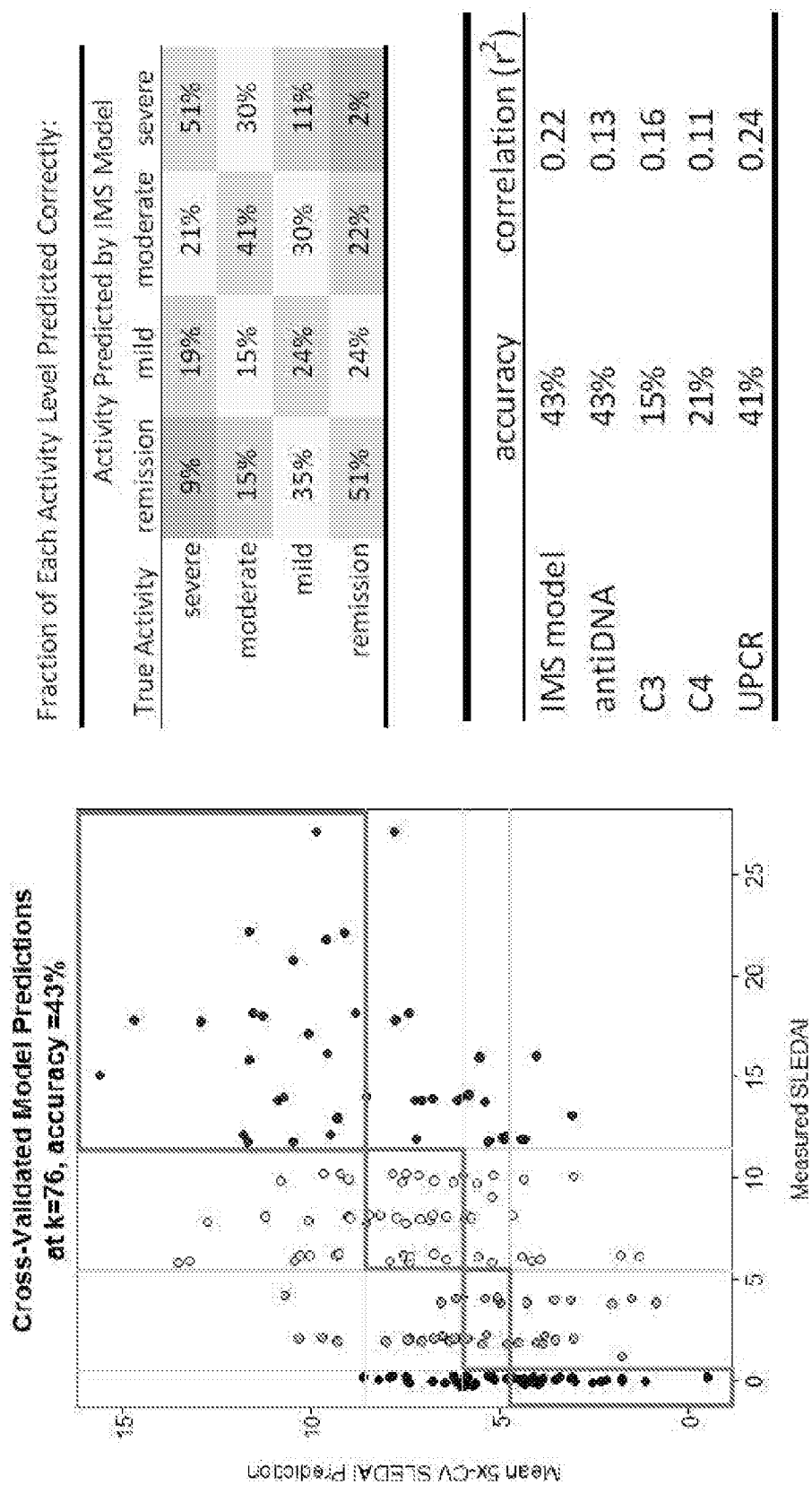
FIG. 9 shows a comparison of predictive capacity of IMS models against known biomarkers anti-dsDNA, C3, C4 and UPCR. The data exemplifies that immunosignature models can estimate SLEDAI scores as well or better than these standard biomarkers.
Figure 10:
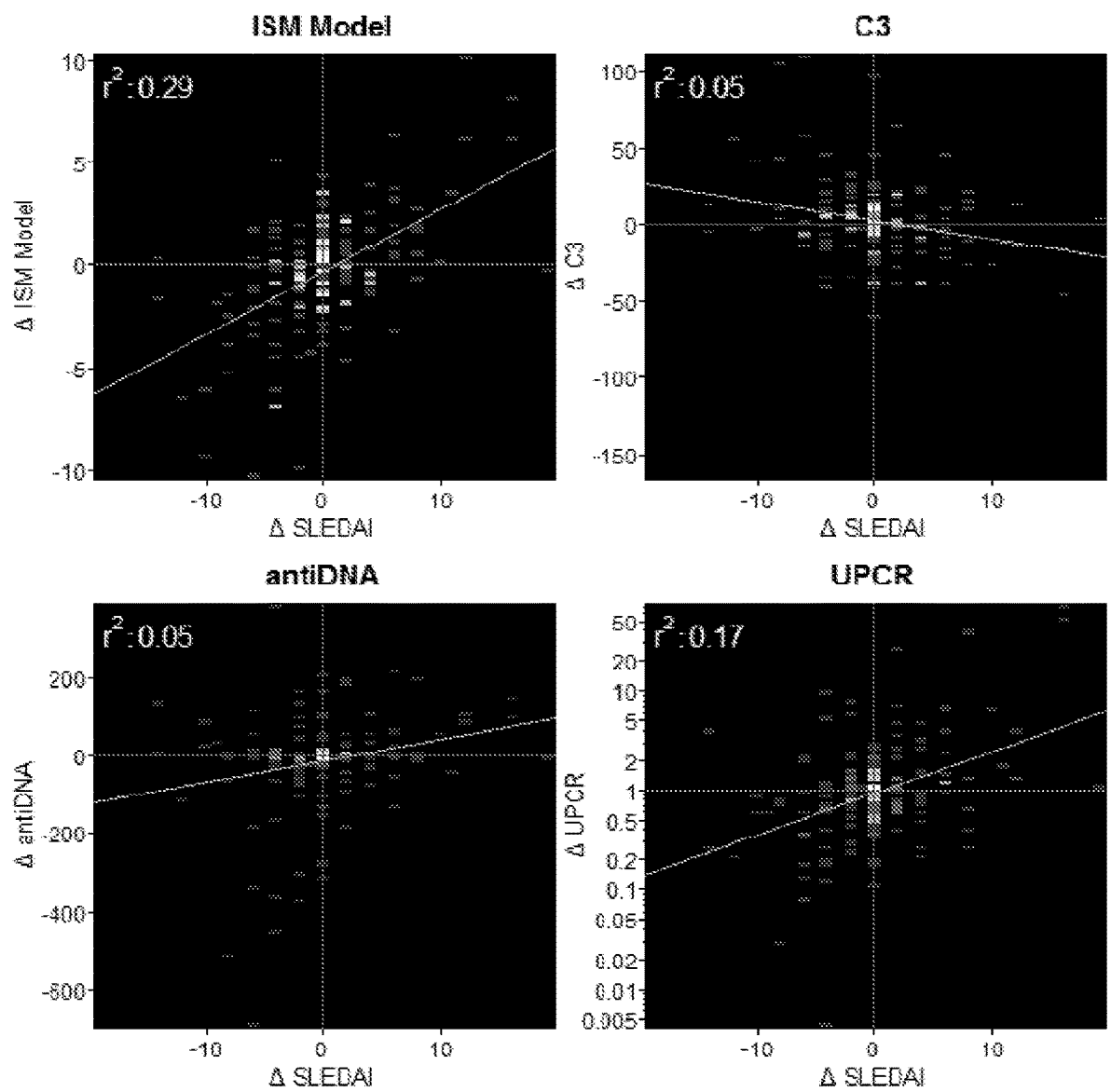
FIG. 10 shows a plot of measured changes in binding in order to monitor a patient's disease state and level of activity. This was done by fitting an elastic net model of changes in SLEDAI score against the peptide intensities obtained in the discriminating peptides. The data support that changes in antibody binding are more closely related to changes in SLEDAI than changes in other biomarkers.

The results also support that immunosignature models can correlate with SLEDAI scores either as well or better than standard biomarkers. Additionally, FIG. 9 shows cross-validated model predictions. Correlations of the immunosignature classifications, complement, and anti-dsDNA, C3, C4 and UPCR biomarkers to the SLEDAI scores were determined. The data demonstrates the accuracy of immunosignature models (IMS model) against several biomarkers, including antiDNA, C3, C4 and UPCR biomarkers. Longitudinal results in FIG. 10 supports that antibody binding in immunosignature models (ISM Model) are more closely related to changes in SLEDAI than changes in other biomarkers, including C3, antiDNA and UPCR.

Figure 11:
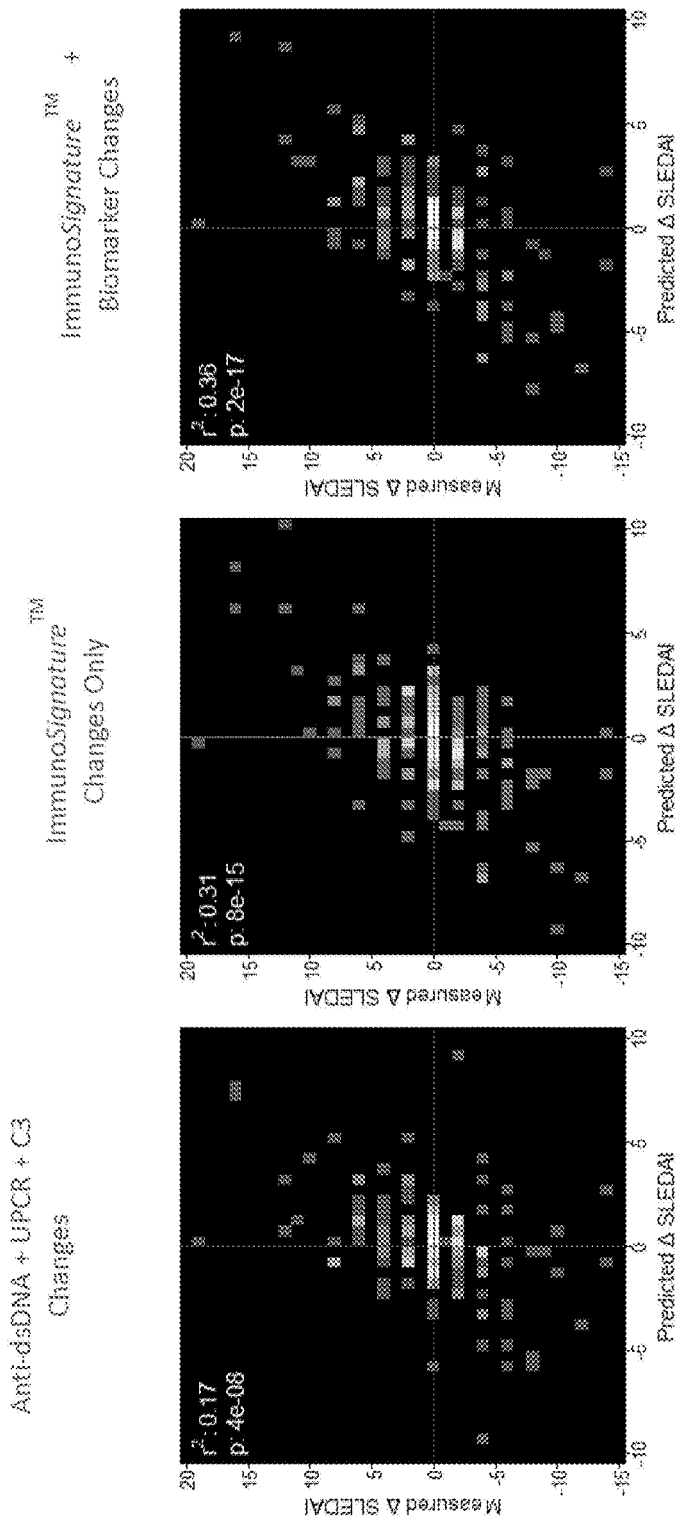
FIG. 11 shows the improvement in predicting lupus and correlating to SLEDAI changes when immunosignature is combined with a biomarker assay.

FIG. 11 further demonstrates the improvement that an immunosignature adds to biomarker predictive capacity, and vice versa. Changes in biomarkers between physician visits are often used to monitor a patient's disease activity. Elastic net models of changes in SLEDAI scores were fit using changes in peptide intensities, and/or changes in anti-dsDNA, UPCR and C3 biomarkers, between successive blood draws (n=167). While as above, changes in antibody binding as seen in immunosignatures (see FIG. 11, middle figure) provided a better substitute for changes in SLEDAI state than changes in biomarkers, either individually or combined (i.e., anti-dsDNA+UPCR+C3 (FIG. 11, left figure), immunosignature assay also benefited in improved predictability when combined with biomarker changes. See FIG. 11, right figure.

Figure 12:
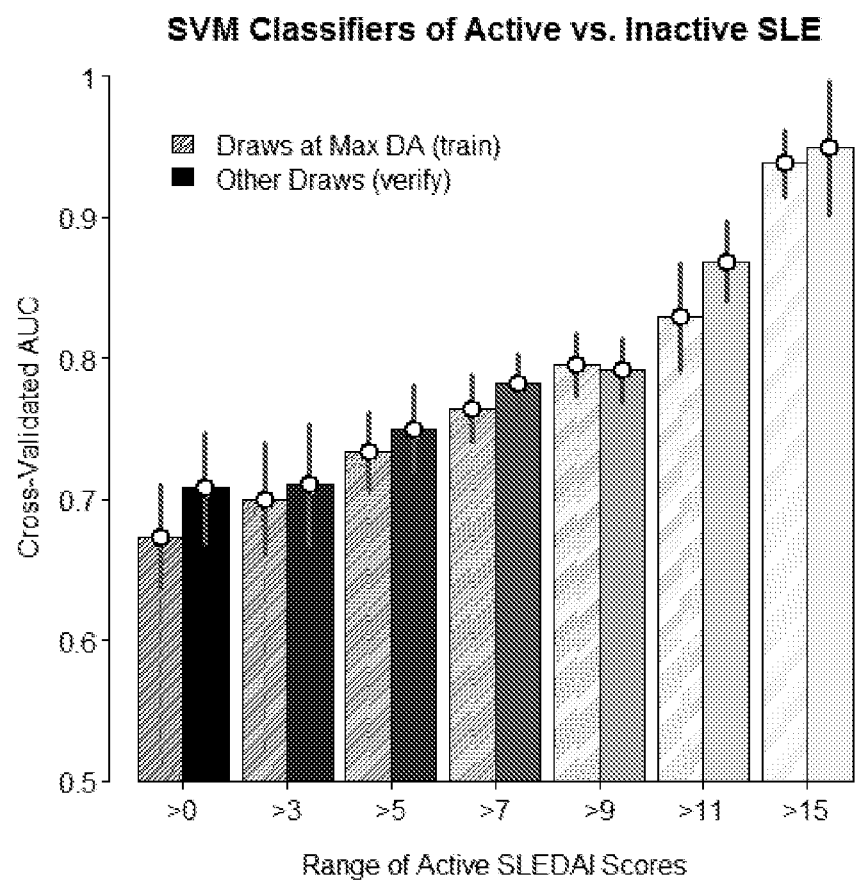
FIG. 12 further demonstrates the difference in immune response that increases with increasing SLEDAI scores, as compared to remission.

FIG. 12 further demonstrates the difference in immune response that increases with increasing SLEDAI scores, as compared to remission. In this study, trained support vector machine (SVM) classifiers were employed to distinguish active from inactive disease. A series of models was trained with "active" defined by increasing SLEDAI threshold. This was in comparison to training only on the $1^{st}$ blood draw from each patient. A five-fold cross validation was used to control for overfit in the training set. The models were verified using other blood draws not used in training.

Conclusions: A simple test that uses specific binding patterns of peripheral-blood antibodies on a peptide array can deliver a single, molecular determination of SLE disease activity.

Example 2—Correlation of SLEDAI Diagnosis and SLE Disease Activity

Immunosignatures for diagnosis and identification of SLE disease activity was determined as above in Example 1 using subjects in a group of subjects having SLE. Immunosignature assays were performed as described in Example 1 and scanned to acquire signal intensity measurements at each feature. Peptide features that showed differential signal between groups were determined by t-test of mean peptide intensities with the Welch adjustment for unequal variances. A binary classifier was developed for each of the contrasts.

Significant Peptides that correlated SLE with SLEDAI score was determined. FIGS. 13A-13G show the motifs and amino acids that were enriched in the discriminating significant peptides in the study. In each of the tables of FIGS. 13A-13G:

"n"=the number of times the motif occurs in the top discriminating peptides;

n. lib=the number of times the motif occurs in the array library

"enrich"=the fold enrichment of a motif in the top discriminating peptides relative to the number of times the motif occurs in the array library.

P=the statistical significance of the occurrence of a motif in the top discriminating peptides Fold enrichment=(no of times a motif (e.g. ABCD) occurs in the list/no of times the motif (ABCD) occurs in the library)/(Total no the motif type (e.g. tetramer) occurs in the list/over total no the motif type (e.g. tetramers) in library). Percent enrichment is "enrichment"×100.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for determining autoimmune disease activity in a subject, said method comprising:
   (a) contacting a sample from the subject to a peptide array comprising a plurality of different peptides on distinct features of the array, wherein the subject is a human and the sample comprises a blood sample;
   (b) detecting the binding of antibodies present in the sample to a subset of the plurality of different peptides on the peptide array to obtain a pattern of binding signals, wherein the subset of peptides comprises at least 20 peptides that are indicative of autoimmune disease activity, wherein the autoimmune disease is systemic lupus erythrematosus (SLE), and wherein the set of peptides indicative of SLE activity on the peptide array comprises one or more sequence motifs selected from the group consisting of SEQ ID NOS 16-47;
   (c) comparing said binding signal to reference binding signals obtained from a plurality of subjects in a reference group having a range of autoimmune disease activities, wherein the range of autoimmune disease activities is determined by the presence of one or more clinical conditions comprising high anti-dsDNA antibodies, low complement protein C3, low complement protein C4, high antinuclear antibody (ANA), high proteinuria, malar rash, CNS manifestation, arthritis, cytopenia, discoid rash, oral ulcers, renal manifestation, immunologic disease, photosensitivity, and serositis and wherein the range of autoimmune disease activities comprises remission, low disease activity, moderate disease activity, and severe disease activity;
   (d) classifying said binding signals as having a presence and/or a severity of autoimmune disease activity in the range of autoimmune disease activity; and (e) determining the presence and/or severity of autoimmune disease activity in said subject, wherein the binding signal of the set of peptides indicative of SLE on the peptide array in the reference samples are lower in subjects from the reference group having a score of at least 12 when using SLEDAI or SLEDAI-SELENA scoring system.

2. The method of claim 1, wherein the peptide array comprises at least 10,000 different peptides.

3. The method of claim 1, wherein the different peptides on the array are synthesized in situ.

4. The method of claim 3, wherein the synthesis of peptides in situ comprises less than 20 different amino acids.

5. The method of claim 4, wherein cysteine, methionine, isoleucine and threonine are excluded during synthesis of the peptide array.

6. The method of claim 5, wherein an average binding signal of the set of peptides indicative of the autoimmune disease in the reference samples is lower in subjects from said reference group having a range of autoimmune disease activities who have high disease activity than the average binding signal of said peptides from subjects in said reference group having a range of autoimmune disease activities who have higher disease activity.

7. The method of claim 1, wherein the set of peptides comprises at least 30 peptides, at least 40 peptides, at least 50 peptides, at least 60 peptides, at least 70 peptides, at least 80 peptides, at least 90 peptides or at least 100 peptides that are indicative of autoimmune disease activity.

8. The method of claim 1, wherein the pattern of binding signals obtained that classifies said autoimmune disease activity is selected from the group consisting of remission, low disease activity, moderate disease activity, and severe disease activity.

9. The method of claim 1, wherein the sample is a blood sample selected from the group consisting of whole blood, plasma, and serum.

10. A method for determining autoimmune disease activity in a subject, said method comprising:
(a) contacting a sample from the subject to a peptide array comprising a plurality of different peptides on distinct features of the array, wherein the subject is a human and the sample comprises a blood sample;
(b) detecting the binding of antibodies present in the sample to a subset of the plurality of different peptides on the peptide array to obtain a pattern of binding signals, wherein the subset of peptides comprises at least 20 peptides that are indicative of autoimmune disease activity, wherein the autoimmune disease is systemic lupus erythrematosus (SLE), and wherein the set of peptides indicative of SLE activity on the peptide array comprises one or more sequence motifs selected from the group consisting of SEQ ID NOS 16-47;
(c) comparing said binding signal to reference binding signals obtained from a plurality of subjects in a reference group having a range of autoimmune disease activities, wherein the range of autoimmune disease activities is determined by the presence of one or more clinical conditions comprising high anti-dsDNA antibodies, low complement protein C3, low complement protein C4, high antinuclear antibody (ANA), high proteinuria, malar rash, CNS manifestation, arthritis, cytopenia, discoid rash, oral ulcers, renal manifestation, immunologic disease, photosensitivity, and serositis and wherein the range of autoimmune disease activities comprises remission, low disease activity, moderate disease activity, and severe disease activity;
(d) classifying said binding signals as having a presence and/or a severity of autoimmune disease activity in the range of autoimmune disease activity; and
(e) determining the presence and/or severity of autoimmune disease activity in said subject, wherein the binding signal of the set of peptides indicative of SLE on the peptide array in the reference samples are lower in subjects from the reference group having a score of less than 2 when using SLEDAI or SLEDAI-SELENA scoring system.

11. The method of claim 10, wherein an average binding signal of the set of peptides indicative of the autoimmune disease in the reference samples is lower in subjects from said reference group having the range of autoimmune disease activities who have high disease activity than the average binding signal of said peptides from subjects in said reference group having a range of autoimmune disease activities who have higher disease activity.

12. The method of claim 10, wherein the set of peptides comprises at least 30 peptides, at least 40 peptides, at least 50 peptides, at least 60 peptides, at least 70 peptides, at least 80 peptides, at least 90 peptides or at least 100 peptides are indicative of autoimmune disease activity.

13. The method of claim 10, wherein the pattern of binding signals obtained that classifies said autoimmune disease activity is selected from the group consisting of remission, low disease activity, moderate disease activity, and severe disease activity.

14. The method of claim 10, wherein the peptide array comprises at least 100,000 different peptides.

15. The method of claim 10, wherein the different peptides on the array are synthesized in situ.

* * * * *

SEQUENCE LISTING

<160> NUMBER OF SEQ ID NOS: 47

<210> SEQ ID NO 1
<211> LENGTH: 78
<212> TYPE: PRT
<213> ORGANISM: Homo sapiens

<400> SEQUENCE: 1

Met Asp Cys Cys Thr Glu Asn Ala Cys Ser Lys Pro Asp Asp Asp Ile
1               5                   10                  15

Leu Asp Ile Pro Leu Asp Asp Pro Gly Ala Asn Ala Ala Ala Ala Lys
            20                  25                  30

Ile Gln Ala Ser Phe Arg Gly His Met Ala Arg Lys Lys Ile Lys Ser
        35                  40                  45

Gly Glu Arg Gly Arg Lys Gly Pro Gly Pro Gly Pro Gly Gly Ala
    50                  55                  60

Gly Val Ala Arg Gly Gly Ala Gly Gly Gly Pro Ser Gly Asp
65                  70                  75

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: Any amino acid

<400> SEQUENCE: 2

Arg Lys Lys Xaa Xaa Ser Gly
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid

<400> SEQUENCE: 3

Lys Xaa Gly Glu Arg
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(8)
<223> OTHER INFORMATION: Any amino acid

<400> SEQUENCE: 4

```
Lys Ser Xaa Glu Arg Xaa Xaa Xaa Gly
1               5
```

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 5

```
Lys Xaa Gly Xaa Arg Gly
1               5
```

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Any amino acid

<400> SEQUENCE: 6

```
Lys Lys Xaa Xaa Ser Gly
1               5
```

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(9)
<223> OTHER INFORMATION: Any amino acid

<400> SEQUENCE: 7

```
His Xaa Ala Arg Lys Xaa Xaa Xaa Xaa Gly
1               5                   10
```

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:

<221> NAME/KEY: MOD_RES
<222> LOCATION: (5)..(7)
<223> OTHER INFORMATION: Any amino acid
<220> FEATURE:
<221> NAME/KEY: MOD_RES
<222> LOCATION: (10)..(10)
<223> OTHER INFORMATION: Any amino acid

<400> SEQUENCE: 8

Lys Xaa Xaa Glu Xaa Xaa Xaa Lys Gly Xaa Gly
1               5                   10

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 9

Arg Gly Arg Xaa Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(6)
<223> OTHER INFORMATION: Any amino acid

<400> SEQUENCE: 10

Ala Ala Lys Xaa Xaa Xaa Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(8)
<223> OTHER INFORMATION: Any amino acid

<400> SEQUENCE: 11

Lys Xaa Xaa Glu Xaa Xaa Arg Xaa Gly
1               5

<210> SEQ ID NO 12
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 12

Arg Xaa Gly Xaa Gly Gly Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 13

Ala Arg Xaa Gly Xaa Xaa Gly Gly
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(6)
<223> OTHER INFORMATION: Any amino acid

<400> SEQUENCE: 14

Val Xaa Arg Gly Xaa Xaa Gly Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (6)..(6)
<223> OTHER INFORMATION: Any amino acid
```

```
<400> SEQUENCE: 15

Gly Xaa Gly Pro Ser Xaa Asp
1               5

<210> SEQ ID NO 16
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 16

Gln Arg Lys Lys
1

<210> SEQ ID NO 17
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 17

Arg Arg Gly Ser
1

<210> SEQ ID NO 18
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 18

His Lys Arg Arg
1

<210> SEQ ID NO 19
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 19

His Arg Leu Asn
1

<210> SEQ ID NO 20
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 20

Lys Val His Arg
1

<210> SEQ ID NO 21
<211> LENGTH: 4
<212> TYPE: PRT
```

```
<213> ORGANISM: Unknown
<220> FEATURE:
<223> OTHER INFORMATION: Description of Unknown:
      SLE motif sequence

<400> SEQUENCE: 21

Lys Lys Trp Arg
1

<210> SEQ ID NO 22
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 22

Arg His Arg Gly
1

<210> SEQ ID NO 23
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 23

Arg Arg His Tyr
1

<210> SEQ ID NO 24
<211> LENGTH: 5
<212> TYPE: PRT
<213> ORGANISM: Unknown
<220> FEATURE:
<223> OTHER INFORMATION: Description of Unknown:
      SLE motif sequence

<400> SEQUENCE: 24

Lys Arg Trp His Phe
1               5

<210> SEQ ID NO 25
<211> LENGTH: 5
<212> TYPE: PRT
<213> ORGANISM: Unknown
<220> FEATURE:
<223> OTHER INFORMATION: Description of Unknown:
      SLE motif sequence

<400> SEQUENCE: 25

Leu Trp Lys His Gly
1               5

<210> SEQ ID NO 26
<211> LENGTH: 5
<212> TYPE: PRT
<213> ORGANISM: Unknown
<220> FEATURE:
<223> OTHER INFORMATION: Description of Unknown:
      SLE motif sequence

<400> SEQUENCE: 26

Trp Lys His Arg Gly
1               5
```

```
<210> SEQ ID NO 27
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 27

Ala Lys Ala Lys
1

<210> SEQ ID NO 28
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 28

Arg His Lys Leu
1

<210> SEQ ID NO 29
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 29

Asn Lys Tyr Lys
1

<210> SEQ ID NO 30
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 30

Lys Phe Ser Gly
1

<210> SEQ ID NO 31
<211> LENGTH: 5
<212> TYPE: PRT
<213> ORGANISM: Unknown
<220> FEATURE:
<223> OTHER INFORMATION: Description of Unknown:
      SLE motif sequence

<400> SEQUENCE: 31

Arg Trp His Phe Asp
1               5

<210> SEQ ID NO 32
<211> LENGTH: 4
<212> TYPE: PRT
<213> ORGANISM: Unknown
<220> FEATURE:
<223> OTHER INFORMATION: Description of Unknown:
      SLE motif sequence
```

```
<400> SEQUENCE: 32

Phe His His Lys
1

<210> SEQ ID NO 33
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 33

Lys Lys Pro His
1

<210> SEQ ID NO 34
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 34

Leu His His Asn
1

<210> SEQ ID NO 35
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 35

Lys Arg Arg His
1

<210> SEQ ID NO 36
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 36

Asn Lys Lys His
1

<210> SEQ ID NO 37
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 37

Ser Pro Asn Leu
1

<210> SEQ ID NO 38
<211> LENGTH: 4
```

```
<212> TYPE: PRT
<213> ORGANISM: Unknown
<220> FEATURE:
<223> OTHER INFORMATION: Description of Unknown:
      SLE motif sequence

<400> SEQUENCE: 38

His Arg Glu Gly
1

<210> SEQ ID NO 39
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 39

Arg His Lys Arg
1

<210> SEQ ID NO 40
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 40

Arg Trp Lys Gly
1

<210> SEQ ID NO 41
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 41

His Phe Arg Asn
1

<210> SEQ ID NO 42
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 42

Lys Ala Ala Tyr
1

<210> SEQ ID NO 43
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 43

Lys Gly Gly Gln
```

```
<210> SEQ ID NO 44
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 44

Lys His Tyr Pro
1

<210> SEQ ID NO 45
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 45

Lys Pro His Pro
1

<210> SEQ ID NO 46
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 46

His Lys Arg Gly
1

<210> SEQ ID NO 47
<211> LENGTH: 4
<212> TYPE: PRT
<213> ORGANISM: Unknown
<220> FEATURE:
<223> OTHER INFORMATION: Description of Unknown:
      SLE motif sequence

<400> SEQUENCE: 47

Arg Trp His Phe
1
```